US010188109B2

(12) United States Patent
Yao et al.

(10) Patent No.: US 10,188,109 B2
(45) Date of Patent: *Jan. 29, 2019

(54) PICOLINAMIDE COMPOUNDS WITH FUNGICIDAL ACTIVITY

(71) Applicant: DOW AGROSCIENCES LLC, Indianapolis, IN (US)

(72) Inventors: Chenglin Yao, Indianapolis, IN (US); Jeremy Wilmot, Indianapolis, IN (US); Jared W. Rigoli, Indianapolis, IN (US); Kevin G. Meyer, Indianapolis, IN (US); Brian A. Loy, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/540,568

(22) PCT Filed: Dec. 21, 2015

(86) PCT No.: PCT/US2015/067201
§ 371 (c)(1),
(2) Date: Jun. 28, 2017

(87) PCT Pub. No.: WO2016/109302
PCT Pub. Date: Jul. 7, 2016

(65) Prior Publication Data
US 2017/0360038 A1    Dec. 21, 2017

Related U.S. Application Data

(60) Provisional application No. 62/098,089, filed on Dec. 30, 2014, provisional application No. 62/098,097, filed on Dec. 30, 2014, provisional application No. 62/255,125, filed on Nov. 13, 2015, provisional application No. 62/255,131, filed on Nov. 13, 2015.

(51) Int. Cl.
| | |
|---|---|
| *C07D 213/81* | (2006.01) |
| *C07C 229/08* | (2006.01) |
| *C07C 271/22* | (2006.01) |
| *A01N 25/00* | (2006.01) |
| *A01N 37/44* | (2006.01) |
| *A01N 43/40* | (2006.01) |
| *A01N 47/12* | (2006.01) |
| *A01N 47/18* | (2006.01) |

(52) U.S. Cl.
CPC ............ *A01N 47/12* (2013.01); *A01N 37/44* (2013.01); *A01N 43/40* (2013.01); *A01N 47/18* (2013.01); *C07C 229/08* (2013.01); *C07C 271/22* (2013.01); *C07D 213/81* (2013.01); *A01N 25/00* (2013.01); *C07C 2601/02* (2017.05); *C07C 2601/04* (2017.05); *C07C 2601/08* (2017.05); *C07C 2601/14* (2017.05)

(58) Field of Classification Search
None
See application file for complete search history.

(56) References Cited

U.S. PATENT DOCUMENTS

| | | | |
|---|---|---|---|
| 4,051,173 | A | 9/1977 | Schact et al. |
| 4,588,735 | A | 5/1986 | Spatz |
| 5,342,835 | A | 8/1994 | Pepin et al. |
| 5,401,871 | A | 3/1995 | Feldmann-Krane et al. |
| 5,475,132 | A | 12/1995 | Pepin et al. |
| 5,563,165 | A | 10/1996 | Talley |
| 5,760,068 | A | 6/1998 | Talley |
| 5,852,042 | A | 12/1998 | Jakobi et al. |
| 6,355,660 | B1 | 3/2002 | Ricks et al. |
| 6,410,572 | B1 | 6/2002 | Schelberger et al. |
| 6,436,421 | B1 | 8/2002 | Schindler et al. |
| 6,521,622 | B1 | 2/2003 | Ricks et al. |
| 6,706,740 | B2 | 3/2004 | Ricks et al. |
| 6,861,390 | B2 | 3/2005 | Meyer et al. |
| 6,903,219 | B2 | 6/2005 | Niyaz et al. |
| 6,916,932 | B2 | 7/2005 | Meyer et al. |
| 6,927,225 | B2 | 8/2005 | Ricks et al. |
| 6,953,807 | B2 | 10/2005 | Hutin et al. |
| 7,034,035 | B2 | 4/2006 | Ricks et al. |
| 7,183,278 | B1 | 2/2007 | Imamura et al. |
| 7,241,804 | B1 | 7/2007 | Hockenberry et al. |
| 7,250,389 | B1 | 7/2007 | Sakanaka et al. |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Guseynov et al, Chemical Abstracts 152:192415, Abstract of Kimya Problemlari, vol. 1, pp. 188-190 (Year: 2009).*

(Continued)

*Primary Examiner* — Zinna Northington Davis
(74) *Attorney, Agent, or Firm* — Faegre Baker Daniels LLP

(57) ABSTRACT

This disclosure relates to picolinamides of Formula I and their use as fungicides.

27 Claims, No Drawings

(56) References Cited

U.S. PATENT DOCUMENTS

| | | |
|---|---|---|
| RE39,991 E | 1/2008 | Ricks et al. |
| 7,442,672 B2 | 12/2008 | Muller et al. |
| 7,459,581 B2 | 12/2008 | Derrer et al. |
| 7,560,565 B2 | 7/2009 | Bacque et al. |
| 7,927,617 B2 | 4/2011 | Koltzenburg |
| 8,008,231 B2 | 8/2011 | Leatherman |
| 8,153,819 B2 | 4/2012 | Dietz |
| 8,236,962 B2 | 8/2012 | Hoekstra et al. |
| 8,349,877 B2 | 1/2013 | Brix et al. |
| 8,415,274 B2 | 4/2013 | Wachendorff-Neumann et al. |
| 8,470,840 B2 | 6/2013 | Klittich et al. |
| 8,476,193 B2 | 7/2013 | Keeney et al. |
| 8,580,959 B2 | 11/2013 | Devasthale et al. |
| 8,586,550 B2 | 11/2013 | Lee et al. |
| 8,604,215 B2 | 12/2013 | Phiasivongsa et al. |
| 8,785,479 B2 | 7/2014 | Meyer et al. |
| 8,835,462 B2 | 9/2014 | Meyer et al. |
| 8,883,811 B2 | 11/2014 | Owen et al. |
| 8,916,579 B2 | 12/2014 | Boebel et al. |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,155,305 B2 | 10/2015 | Gary |
| 9,156,816 B2 | 10/2015 | Ito et al. |
| 9,179,674 B2 | 11/2015 | Martin et al. |
| 9,185,911 B2 | 11/2015 | Inami et al. |
| 9,198,419 B2 | 12/2015 | Owen et al. |
| 9,247,741 B2 | 2/2016 | DeLorbe et al. |
| 9,265,253 B2 | 2/2016 | Li et al. |
| 9,265,255 B2 | 2/2016 | Funke |
| 9,271,496 B2 | 3/2016 | Kemmitt |
| 9,271,497 B2 | 3/2016 | Lorsbach |
| 9,414,596 B2 | 8/2016 | Hoekstra et al. |
| 9,439,422 B2 | 9/2016 | Martin et al. |
| 9,482,661 B2 | 11/2016 | Ross |
| 9,549,555 B2 | 1/2017 | DeLorbe et al. |
| 9,549,556 B2 | 1/2017 | DeKorver et al. |
| 9,629,365 B2 | 4/2017 | Li et al. |
| 9,681,664 B2 | 6/2017 | LaLonde et al. |
| 9,686,984 B2 | 6/2017 | DeKorver et al. |
| 9,700,047 B2 | 7/2017 | Lu |
| 9,750,248 B2 | 9/2017 | Ouimette et al. |
| 9,828,408 B2 | 11/2017 | Kalayanov |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,304 B2 | 5/2018 | DeKorver |
| 2002/0119979 A1 | 8/2002 | Degenhardt et al. |
| 2002/0177578 A1 | 11/2002 | Ricks et al. |
| 2003/0018052 A1 | 1/2003 | Ricks et al. |
| 2003/0022902 A1 | 1/2003 | Ricks et al. |
| 2003/0022903 A1 | 1/2003 | Ricks et al. |
| 2005/0239873 A1 | 10/2005 | Hockenbery et al. |
| 2006/0167281 A1 | 7/2006 | Meijer |
| 2007/0010401 A1 | 1/2007 | Noon |
| 2007/0066629 A1 | 3/2007 | Tormo i Biasco et al. |
| 2009/0203770 A1 | 8/2009 | Hockenberry et al. |
| 2009/0306142 A1 | 12/2009 | Carson et al. |
| 2010/0016163 A1 | 1/2010 | Keiper et al. |
| 2011/0070278 A1 | 3/2011 | Lopez |
| 2011/0082162 A1 | 4/2011 | Lorsbach et al. |
| 2012/0245031 A1 | 9/2012 | Gewehr et al. |
| 2013/0296372 A1 | 11/2013 | Owen et al. |
| 2014/0051678 A1 | 2/2014 | Clement-Schatlo et al. |
| 2014/0128411 A1 | 5/2014 | Ogawa et al. |
| 2014/0187587 A1 | 7/2014 | Ouimette et al. |
| 2014/0357713 A1 | 12/2014 | Damaj et al. |
| 2015/0018374 A1 | 1/2015 | Taggi et al. |
| 2015/0065529 A1 | 3/2015 | Owen et al. |
| 2015/0181868 A1 | 7/2015 | DeKorver et al. |
| 2015/0289508 A1 | 10/2015 | Meyer et al. |
| 2015/0322051 A1 | 11/2015 | Lu et al. |
| 2016/0007601 A1 | 1/2016 | Boebel et al. |
| 2016/0037774 A1 | 2/2016 | Schulz |
| 2016/0183526 A1 | 6/2016 | Hopkins et al. |
| 2016/0183527 A1 | 6/2016 | Hopkins et al. |
| 2016/0183528 A1 | 6/2016 | Hopkins et al. |
| 2017/0183324 A1 | 6/2017 | Li et al. |
| 2017/0273303 A1 | 9/2017 | DeKorver et al. |
| 2017/0273306 A1 | 9/2017 | LaLonde et al. |
| 2017/0290333 A1 | 10/2017 | Bravo-Altamirano et al. |
| 2017/0295792 A1 | 10/2017 | Bravo-Altamirano et al. |
| 2017/0369421 A1 | 12/2017 | Yao |
| 2018/0000075 A1 | 1/2018 | Bravo-Altamirano et al. |
| 2018/0000080 A1 | 1/2018 | Buchan |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |
| 2018/0002320 A1 | 1/2018 | Wilmot |
| 2018/0037541 A1 | 2/2018 | Yao |

FOREIGN PATENT DOCUMENTS

| | | |
|---|---|---|
| EP | 3141118 | 3/2017 |
| FR | 2649699 | 1/1991 |
| JP | 19940026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 1997019908 | 6/1997 |
| WO | 199741103 | 11/1997 |
| WO | 1998018751 | 5/1998 |
| WO | 1999011127 | 11/1999 |
| WO | 2000076979 | 12/2000 |
| WO | 200114339 | 3/2001 |
| WO | 2005121069 | 12/2005 |
| WO | 2008079387 | 7/2008 |
| WO | WO 2011/056240 A2 * | 5/2011 |
| WO | 2012016989 | 2/2012 |
| WO | 2012020777 | 2/2012 |
| WO | 2014105844 | 7/2014 |
| WO | 2016007525 | 1/2016 |
| WO | 2016109288 | 7/2016 |
| WO | 2016109289 | 7/2016 |
| WO | 2016109290 | 7/2016 |
| WO | 2016109291 | 7/2016 |
| WO | 2016109300 | 7/2016 |
| WO | 2016109301 | 7/2016 |
| WO | 2016109303 | 7/2016 |
| WO | 2016109304 | 7/2016 |
| WO | 2016109305 | 7/2016 |
| WO | 2015005355 | 3/2017 |

OTHER PUBLICATIONS

Anonymous, Synergistic Fungicidal Composition of Heterocyclic Aromatic Amides and Triazoles, IP.com Journal, IP.com, Electronic Publication, West Henrietta, NY, US, Jul. 2004, 11 pages.

Backman, P., Fungicide Formulation: Relationship to Biological Activity, Ann. Rev. Phytopathol, 1978, 16, pp. 211-237.

BASF New Fungicide Xemium Got Full Approval in EU, Agronews, Jul. 18, 2012 [retrieved on Feb. 4, 2014]. Retrieved from the Internet: ,URL:http://news.agropages.com/News/NewsDetail---7386.htm, 1 page.

Bolton, M. et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.

Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-855.

FRAC Code List: Fungicides Sorted by Mode of Action (including FRAC Code numbering), Fungicide Resistance Action Committee, Dec. 2008, 10 pages.

(56) References Cited

OTHER PUBLICATIONS

Fungicidal Mixtures, IP.com Prior Art Database Technical Disclosure, (Jul. 5, 2005), XP055073888, DOI: http://ip.com/pdf/ipcompad/IPCOM000126160apdf, 12 pages.
Gisi, U., "Synergistic Interaction of Fungicides in Mixtures," The American Phytopathological Society, vol. 86, No. 11, 1996, pp. 1273-1279.
Hu, Z. et al., "Synthesis of Novel Analogues of Antimycin A3," Tetrahedron Letters 49 (2008), pp. 5192-5195.
Huang, C. et al., "Synergistic Interactions between Chitinase ChiCW and Fungicides Against Plant Fungal Pathogens," J. Microbiol. Biotechnol., 2008, 18(4), pp. 784-787.
Kissling, E., "Crop Protection Pipeline Value Jumps to Euro 2.4 Billion," BASF SE, Mar. 10, 2011 [retrieved on Feb. 4, 2014], Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control;" GCM, Jul. 2008, pp. 84-87.
Ueki, M., et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-643.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.
PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 4 pages.
Tani, K. et al., The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from *Streptomyces* sp. 517-02," Bioorganic & Medicinal Chemistry Letters, vol. 15, No. 8, 2005, pp. 2011-2014.
Usuki, Y. et al., Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Written Opinion and Search Report for PCT Patent Application No. PCT/US2015/067201 dated Mar. 11, 2016, 8 pages.
Cantacuzene, D., "Optimization of the papain catalyzed esterification of amino acids by alcohols and diols," Tetrahedron, vol. 45, Issue 3 (1989), pp. 741-748.
Washburn, W.N., "Identification of a nonbasic melanin hormone receptor 1 antagonist as an antiobesity clinical candidate," Journal of Medicinal Chemistry, 57, 18 (Aug. 28, 2014), pp. 7509-7522.
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012). (Uploaded in 3 parts due to size restrictions).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Fujita T, Ed. "Quantitative structure-activity analysis and database-aided bioisosteric structural transformation procedure as methodologies of agrochemical design"; Classical and Three Dimensional QSAR in Agrochemistry, American Chemical Society Symposium Series, Washington, D.C. vol. 606, pp. 13-34 (1995).
Goellner et al. "Phakopsora pachyrhizi, the causal agent of Asian soybean rust." Molecular Plant Pathology, vol. 11, No. 2, pp. 169-177 (2010).
Kendall, S. et al. "Changes in sensitivity to DMI fungicides in Rhynchosporium secalis". Crop Protection, vol. 12, No. 5, pp. 357-362 (1993).
Lippard, S. "Chemical Synthesis: The Art of Chemistry". Nature, vol. 416, p. 587 (2002).
Patani et al. "Biosterism: A rational approach in drug design". Chemical Reviews, vol. 96, No. 8, pp. 3147-3176 (1996).
Shimano et al. "Total synthesis of the antifungal dilactones UK-2A and UK-3A: the determination of their relative and absolute configurations, analog synthesis and antifungal activities". Tetrahedron, vol. 54, pp. 12745-12774 (1998).
Chitwood, D. "Nematicides". Encyclopedia of Agrochemicals (3), pp. 1104-1115, John Wiley & Sons, New York, NY, http://naldc.nal.usda.gov/download/43874/PDF (2003).
Hanafi et al. "UK2A, B, C, and D, Novel Antifungal Antibiotics from *Streptomyces* sp 517-02 II. Structural Elucidation." The Journal of Antibiotics, vol. 49, Issue 12, pp. 1226-1231 (1996).
Shibata et al. "UK1, a Novel Cytotoxic Metabolite from *Streptomyces* sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Stephenson, G., et al. "Glossary of terms relating to pesticides". Pure and Applied Chemistry, vol. 78, No. 11, pp. 2075-2154, International Union of Pure and Applied Chemistry (2006).
Ueki, M., et al., "UK-1, a Novel Cytotoxic Metabolite from *Streptomyces* sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, a Novel Antifungal Antibiotic from *Streptomyces* sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from *Streptomyces* sp. 517-02". The Journal of Antibiotics, vol. 50, Issue 12, pp. 1052-1057 (1997).
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report for PCT/US14/058070, dated Dec. 15, 2014, 4 pages.
International Searching Authority, Written Opinion for PCT/US14/058070, dated Dec. 15, 2014, 5 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.
International Searching Authority, International Search Report and Written Opinion for PCT/US1567111 dated Mar. 11, 2016, 11 pages.

(56) References Cited

OTHER PUBLICATIONS

International Searching Authority, International Search Report and Written Opinion for PCT/US1567113 dated Mar. 11, 2016, 10 pages.
International Searching Authority, International Search Report and Written Opinion for PCT/US1567116 dated Mar. 7, 2016, 8 pages.
International Searching Authority, International Search Report and Written Opinion for PCT/US1567199 dated Mar. 11, 2016, 9 pages.
International Searching Authority, International Search Report and Written Opinion for PCT/US1567200 dated Mar. 10, 2016, 10 pages.
International Searching Authority, International Search Report and Written Opinion for PCT/US1567204 dated Mar. 7, 2016, 10 pages.
International Searching Authority, International Search Report PCT/US2000/021523 dated Jul. 7, 2001, 7 pages.
International Searching Authority, International Search Report and Written Opinion for PCT/US1567207 dated Mar. 11, 2016, 12 pages.
International Searching Authority, International Search Report and Written Opinion for PCT/US2013039726 dated Sep. 17, 2013, 9 pages.
International Searching Authority, International Search Report and Written Opinion for PCT/US2013039735 dated Oct. 18, 2013, 8 pages.
International Searching Authority, International Search Report and Written Opinion for PCT/US2013077472 dated Apr. 16, 2014, 9 pages.
International Searching Authority, International Search Report and Written Opinion for PCT/US2013077537 dated Apr. 16, 2014, 11 pages.
International Searching Authority, International Search Report and Written Opinion for PCT/US2014071692 dated Apr. 20, 2015, 6 pages.
International Searching Authority, International Search Report and Written Opinion for PCT/US2014071695 dated Apr. 17, 2015, 6 pages.
International Searching Authority, International Search Report and Written Opinion for PCT/US2014071699 dated Apr. 20, 2015, 6 pages.
International Searching Authority, International Search Report and Written Opinion for PCT/US2014071700 dated Apr. 17, 2015, 9 pages.
International Searching Authority, International Search Report and Written Opinion for PCT/US2015066760 dated Apr. 14, 2016, 11 pages.
International Searching Authority, International Search Report and Written Opinion for PCT/US2015066764 dated Apr. 28, 2016, 11 pages.
International Searching Authority, International Search Report and Written Opinion for PCT/US20150051598 dated Dec. 6, 2010, 5 pages.
International Searching Authority, International Search Report for PCT/US14/058067, dated Dec. 22, 2014, 4 pages.
International Searching Authority, Written Opinion for PCT/US14/058067, dated Dec. 22, 2014, 5 pages.
International Searching Authority, International Search Report and Written Opinion for PCT/US2015/067115, dated Mar. 11, 2016, 6 pages.
International Searching Authority, International Search Report and Written Opinion for PCT/US1567206 dated Mar. 1, 2016, 8 pages.
Database Chemabs Online, Chemical Abstracts Service, Columbus Ohio, US: accession No. CA63:16300d XP002164206 (Cited in International Search Report for PCT/US2000/021523).
Guseynov et al: "Study of the reaction of aminoacetic acid with dihydric alcohols and production of epoxy esters" Chemical Problems, 2009 (1), pp. 188-190. English Machine Translation attached.

* cited by examiner

PICOLINAMIDE COMPOUNDS WITH FUNGICIDAL ACTIVITY

CROSS REFERENCE TO RELATED APPLICATIONS

This application is a U.S. National Phase filing of International Application No. PCT/US2015/067201, filed Dec. 21, 2015, which claims the benefit of U.S. Provisional Patent Application Ser. Nos. 62/098,089 filed Dec. 30, 2014, 62/098,097 filed Dec. 30, 2014, 62/255,125 filed Nov. 13, 2015 and 62/255,131 filed Nov. 13, 2015, the disclosures of which are hereby expressly incorporated by reference herein in their entirety.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to picolinamides and their use as fungicides. The compounds of the present disclosure may offer protection against ascomycetes, basidiomycetes, deuteromycetes and oomycetes.

One embodiment of the present disclosure may include compounds of Formula I:

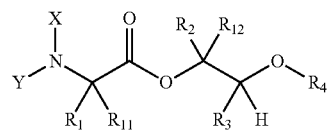

I

X is hydrogen or $C(O)R_5$;
Y is hydrogen, $C(O)R_5$, or Q;
Q is

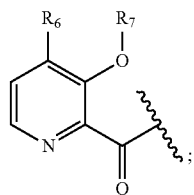

$R_1$ and $R_{11}$ are independently chosen from hydrogen or alkyl, optionally substituted with 0, 1 or multiple $R_8$; alternatively, $R_1$ and $R_{11}$ may be taken together to form a 3-6 membered saturated or partially saturated carbocyclic or heterocyclic ring, optionally substituted with 0, 1 or multiple $R_8$;
$R_2$ and $R_{12}$ are independently chosen from hydrogen, alkyl, aryl, or alkenyl, each optionally substituted with 0, 1 or multiple $R_8$;
$R_3$ is methyl;
$R_4$ is chosen from alkyl, aryl, or acyl, each optionally substituted with 0, 1 or multiple $R_8$;
$R_5$ is chosen from alkoxy or benzyloxy, each optionally substituted with 0, 1, or multiple $R_8$;
$R_6$ is chosen from hydrogen, alkoxy, or halo, each optionally substituted with 0, 1, or multiple $R_8$;
$R_7$ is chosen from hydrogen, —$C(O)R_9$, or —$CH_2OC(O)R_9$;
$R_8$ is chosen from hydrogen, alkyl, aryl, acyl, halo, alkenyl, alkoxy, or heterocyclyl, each optionally substituted with 0, 1, or multiple $R_{10}$,
$R_9$ is chosen from alkyl, alkoxy, or aryl, each optionally substituted with 0, 1, or multiple $R_8$;
$R_{10}$ is chosen from hydrogen, alkyl, aryl, acyl, halo, alkenyl, alkoxy, or heterocyclyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms.

The term "alkoxy" refers to an —OR substituent.
The term "acyloxy" refers to an —OC(O)R substituent.
The term "cyano" refers to a —C≡N substituent.
The term "hydroxyl" refers to an —OH substituent.
The term "amino" refers to a —$N(R)_2$ substituent.
The term "arylalkoxy" refers to —$O(CH_2)_n$Ar where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —$NO_2$ substituent.
The term thioalkyl refers to an —SR substituent.

Throughout the disclosure, reference to the compounds of Formula I is read as also including all stereoisomers, for example diastereomers, enantiomers, and mixtures thereof. In another embodiment, Formula I is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), coumoxystrobin, cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dipymetitrone, dithianon, dodemorph, dodemorph acetate, dodine, dodine free base, edifenphos, enestrobin, enestroburin, enoxastrobin, epoxiconazole, ethaboxam, ethoxyquin, etridiazole, famoxadone, fenamidone, fenaminostrobin, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flufenoxystrobin, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isofetamid, isoprothiolane, isopyrazam, isotianil, kasugamycin, kasugamycin hydrochloride hydrate, kresoxim-methyl, laminarin, mancopper, mancozeb, mandestrobin, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picarbutrazox, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyraziflumid, pyrazophos, pyribencarb, pyributicarb, pyrifenox, pyrimethanil, pyrofenone, pyrisoxazole, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolprocarb, tolylfluanid, triadimefon, triadimenol, triazoxide, triclopyricarb, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateame, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb, prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, afidopyropen, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, broflanilide, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, clacyfos, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallé-thrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, fluhexafon, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptafluthrin, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, momfluorothrin, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyflubumide, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyriminostrobin, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, tetraniliprole, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tioxazafen, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenquinotrione, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiafenacil, tiocarbazil, tioclorim, tolpyralate, topramezone, tralkoxydim, triafamone, tri-allate, triasulfuron, triaziflam, tribenuron, tricamba, triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Pyricularia oryzae*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Colletotrichum lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula I. The following descriptions and examples are provided for illustrative purposes and should not be construed as limiting in terms of substituents or substitution patterns.

Compounds of Formula 1.2, wherein $R_8$ is as originally defined, can be prepared by the method shown in Scheme 1, step a. The compound of Formula 1.1 can be treated with a base, such as N-Cyclohexyl-N-methylcyclohexanamine, in the presence of triphenylbismuth(V) acetate and copper(II) acetate in a solvent, such as toluene at a temperature of about 23° C. to 40° C. to afford compounds of Formula 1.2, wherein $R_8$ is as previously defined, as shown in a. Alternatively, compounds of Formula 1.2, wherein $R_8$ is as originally defined, can be prepared by the method shown in Scheme 1, step b. The compound of Formula 1.1 can be treated with a triarylbismuth(III) reagent (prepared according to the method presented in *Synthetic Commun.* 1996, 26 (24), 4569-4575), such as tris(4-fluoro-2-methylphenyl)bismuthane, in the presence of an oxidant, such as peracetic acid, and a catalyst, such as copper(II) acetate, in a solvent, such as dichloromethane at a temperature of about 23° C. to 40° C. to afford compounds of Formula 1.2, wherein $R_8$ is as previously defined, as shown in b. Compounds of Formula 1.3, wherein $R_8$ is as originally defined, can be prepared by the method shown in Scheme 1, step c. The compound of Formula 1.1 can be treated with a catalyst, such as Tris (dibenzylideneacetone)dipalladium(0) ($Pd_2(dba)_3$), and a ligand, such as diphenylphosphino ferrocine (dppf), in the presence of an allylic carbonate, such as (E)-tert-butyl (4,4,4-trifluorobut-2-en-1-yl) carbonate, in a solvent such as THF at a temperature of about 23° C. to 80° C. to afford compounds of Formula 1.3, wherein $R_8$ is as previously defined, as shown in c. Compounds of Formula 1.4, wherein $R_8$ is as originally defined, can be prepared by the method shown in Scheme 1, step d. The compound of Formula 1.1 can be treated with (bromomethyl)benzene in the presence of silver(I) oxide and potassium iodide in a solvent, such as dichloromethane (DCM), at a temperature of about 23° C. to reflux to afford compounds of Formula 1.4, as shown in d.

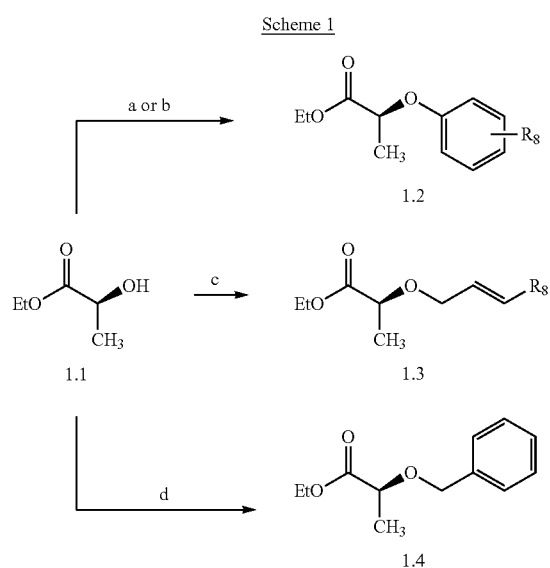

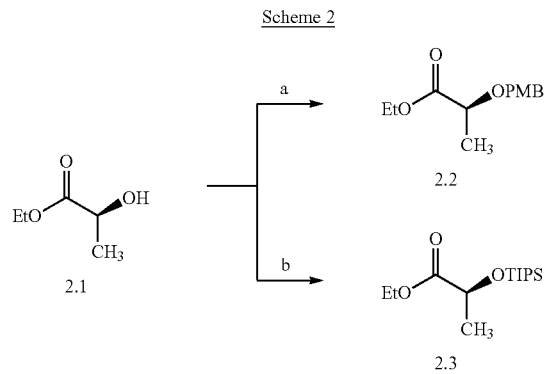

Compounds of Formula 2.2, can be prepared by the method shown in Scheme 2, step a. The compound of Formula 2.1 can be treated with 4-methoxybenzyl 2,2,2-trichloroacetimidate, in the presence of camphorsulfonic acid (CSA) in a solvent, such as DCM at a temperature of about 23° C. to afford compounds of Formula 2.2, as shown in a. The compound of Formula 2.3, can be prepared by the method shown in Scheme 2, step b. The compound of Formula 2.3 can be treated with triisopropylsilyl chloride, in the presence of a base such as imidazole, in a solvent such as dichloromethane (DCM) at a temperature of about 0° C. to afford compounds of Formula 2.3, as shown in b.

The compound of Formula 3.2, wherein $R_2$ is a previously defined, can be prepared by the method shown in Scheme 3, step a. The compound of Formula 3.1 can be treated with tert-butyldimethylsilyl chloride, in the presence of a base such as imidazole, in a solvent such as dimethylformamide (DMF) at a temperature of about 23° C. to afford compounds of Formula 3.2, wherein $R_2$ is as previously defined, as shown in a.

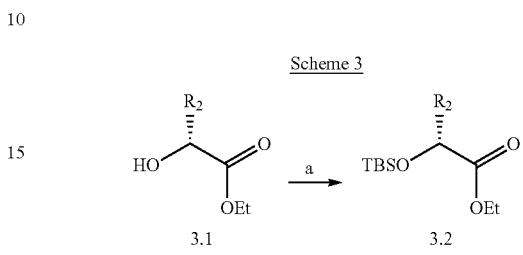

Compounds of Formula 4.1 can be prepared by the method shown in Scheme 4, step a. The compound of Formula 2.3 can be treated with a reducing agent, such as diisobutylaluminum hydride (DIBAL) in a solvent, such as DCM at a temperature of about −78° C. to afford compounds of Formula 4.1, as shown in a.

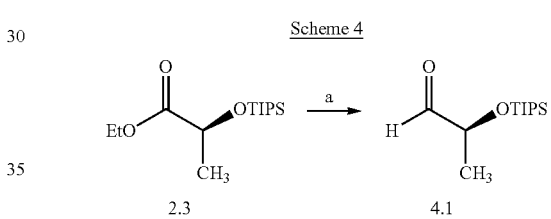

Compounds of Formula 5.1, wherein $R_2$ is as previously defined, can be prepared by the method shown in Scheme 5, step a. The compound of Formula 3.2 can be treated with a reducing agent, such as diisobutylaluminum hydride (DIBAL) in a solvent, such as DCM at a temperature of about −78° C. to afford compounds of Formula 5.1, wherein $R_2$ is as previously defined, as shown in a.

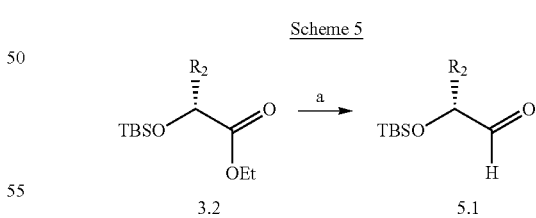

Compounds of Formula 6.2, wherein $R_2$ and $R_4$ are as previously defined, can be prepared by the method shown in Scheme 4, step a. The compound of Formula 6.1, wherein $R_4$ is as previously defined, can be treated with a metallic nucleophile, such as $R_2$—MgBr, and a reducing agent, such as lithium borohydride, in a solvent such as THF at a temperature of about 0° C. to ambient temperature to afford compounds of Formula 6.2, wherein $R_2$ and $R_4$ are as previously defined, as shown in a.

Scheme 6

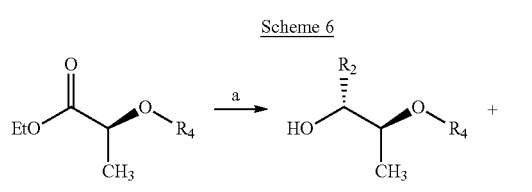

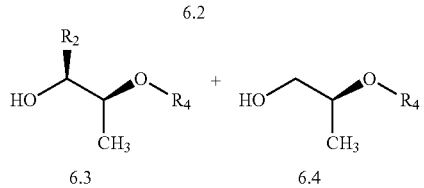

Compounds of Formula 7.1, wherein $R_2$ and $R_3$ are as previously defined, can be prepared by the method shown in Scheme 7, step a. The compound of Formula 4.1, wherein $R_3$ is as previously defined, can be treated with a metallic nucleophile, such as $R_2$—MgBr, in a solvent such as diethyl ether at a temperature of about −78° C. to ambient temperature to afford compounds of Formula 7.1, wherein $R_2$ and $R_3$ are as previously defined, as shown in a.

Scheme 7

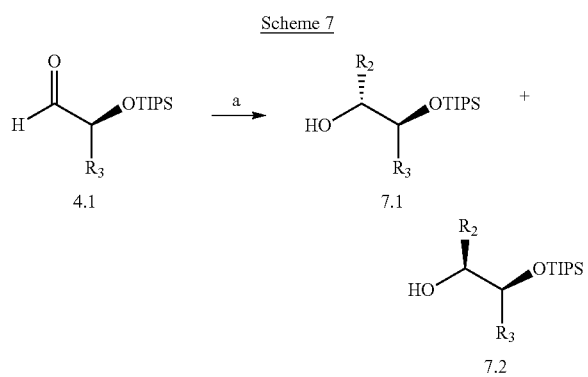

Compounds of Formula 8.1, wherein $R_2$ and $R_3$ are as previously defined, can be prepared by the method shown in Scheme 5, step a. The compound of Formula 5.1, wherein $R_2$ is as previously defined, can be treated with a metallic nucleophile, such as $R_3$—MgBr, in a solvent such as diethyl ether at a temperature of about −78° C. to ambient temperature to afford compounds of Formula 8.1, wherein $R_2$ and $R_3$ are as previously defined, as shown in a.

Scheme 8

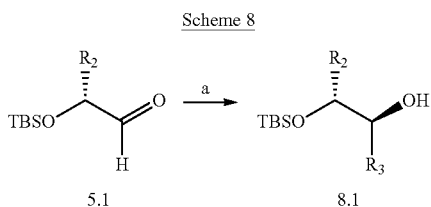

Compounds of Formula 9.3, wherein $R_2$ is as previously defined, can be prepared by the method shown in Scheme 9, steps a-b. The compound of Formula 9.1 can be treated with a base, such as sodium hydride, and (bromomethyl)benzene in a solvent, such as DMF, at a temperature of about 0° C. to ambient temperature to afford compounds of Formula 9.2, as shown in a. The compound of Formula 9.2, wherein $R_2$ is as previously defined, can be treated with ceric ammonium nitrate in a solvent such as acetonitrile at a temperature of about 0° C. to afford compounds of Formula 9.3, wherein $R_2$ is as previously defined, as shown in b.

Scheme 9

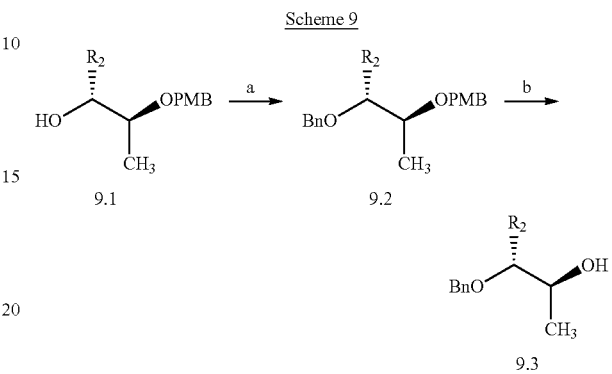

Compounds of Formula 10.4, wherein $R_8$ is as previously defined, can be prepared by the method shown in Scheme 10, steps a-c. The compound of Formula 10.1 can be treated with a base, such as sodium hydride, and 4-methoxybenzyl bromide in a solvent, such as DMF, at a temperature of about 0° C. to ambient temperature to afford compounds of Formula 10.2, as shown in a. The compound of Formula 10.2, can be treated with tetrabutylammonium fluoride in a solvent such as THF at a temperature of about 0° C. to ambient temperature to afford compounds of Formula 10.3, as shown in b. The compound of Formula 10.3 can be treated with a base, such as N-cyclohexyl-N-methylcyclohexanamine, in the presence of triphenylbismuth(V) acetate and copper(II) acetate in a solvent, such as toluene at a temperature of about 23° C. to 40° C. to afford compounds of Formula 10.4, wherein $R_8$ is as previously defined, as shown in c.

Scheme 10

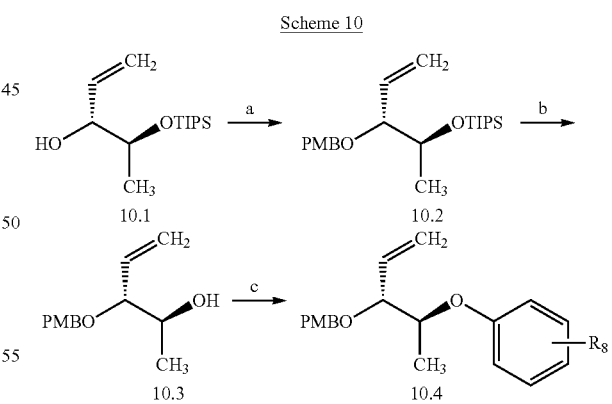

Compounds of Formula 11.3, wherein $R_8$ is as previously defined, can be prepared by the method shown in Scheme 11, steps a-b. The compound of Formula 11.1 can be treated with a base, such as potassium tert-butoxide, in the presence of 1,2,4-trifluorobenzene in a solvent, such as DMF at a temperature of about 23° C. to 60° C. to afford compounds of Formula 11.2, wherein $R_8$ is as previously defined, as shown in a. The compound of Formula 11.2 can be treated with tetrabutylammonium fluoride in a solvent such as THF at a temperature of about 0° C. to ambient temperature to afford compounds of Formula 11.3, wherein $R_8$ is as previously defined, as shown in b.

Scheme 11

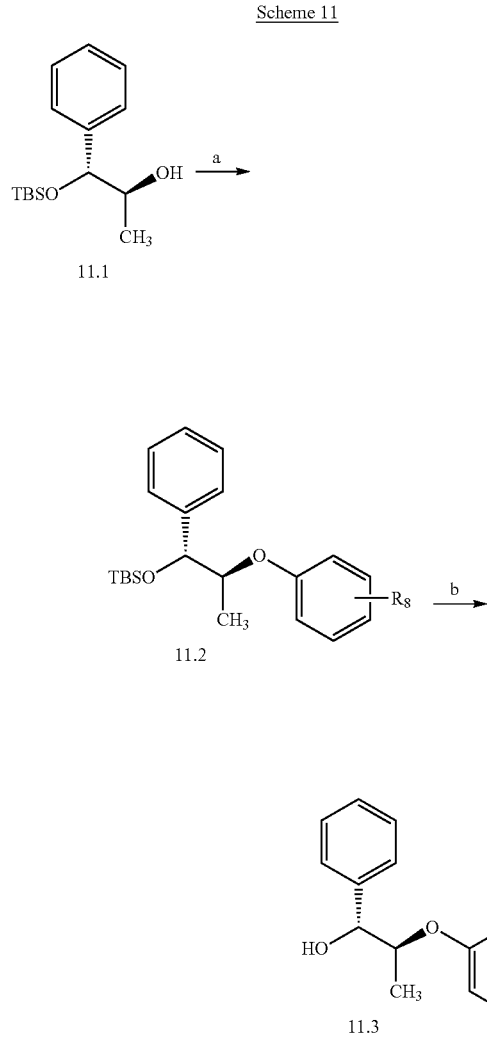

Compounds of Formula 12.4, wherein $R_4$ is as previously defined, can be prepared by the method shown in Scheme 12, steps a-c. The compound of Formula 12.1 can be treated with a base, such as lithium borohydride, and a methylating reagent, such as methyllithium, in a solvent such as diethyl ether at a temperature of about −78° C. to ambient temperature to afford compounds of Formula 12.2, as shown in a. The compound of Formula 12.2 can be treated with a base, such as sodium hydride, a catalyst, such as tetrabutylammonium iodide (TBAI), and an alkyl bromide, such as $R_4$—Br wherein $R_4$ is as previously defined, in a solvent such as THF at a temperature of about 23° C. to refluxing temperature to afford compounds of Formula 12.3, as shown in b. The compound of Formula 12.3 can be treated with an oxidant, such as 2,3-dichloro-5,6-dicyano-1,4-benzoquinone (DDQ), in a solvent such as DCM at a temperature of about 0° C. to ambient temperature to afford compounds of Formula 12.4, as shown in c.

Scheme 12

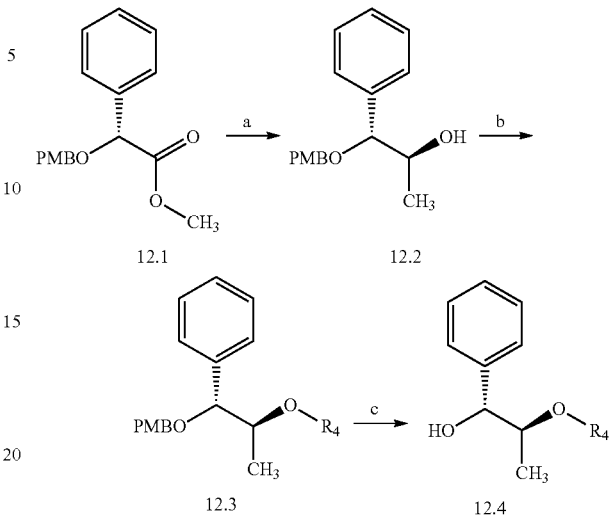

Compounds of Formula 13.2, wherein $R_8$ is as previously defined, can be prepared by the method shown in Scheme 13, steps a-b. The compound of Formula 9.3, wherein $R_2$ is as previously defined, can be treated with a base, such as potassium tert-butoxide, in the presence of 1,2,4-trifluorobenzene in a solvent, such as DMF at a temperature of about 23° C. to 60° C. to afford compounds of Formula 13.1, wherein $R_2$ and $R_8$ are as previously defined, as shown in a. The compound of Formula 13.1, wherein $R_2$ and $R_8$ are as previously defined, can be treated with a hydrogenation catalyst, such as palladium on carbon, in a solvent mixture such as 1:2 cyclohexene:ethanol at a temperature of about ambient temperature to about 70° C. to afford compounds of Formula 13.2, wherein $R_2$ and $R_8$ are as previously defined, as shown in b.

Scheme 13

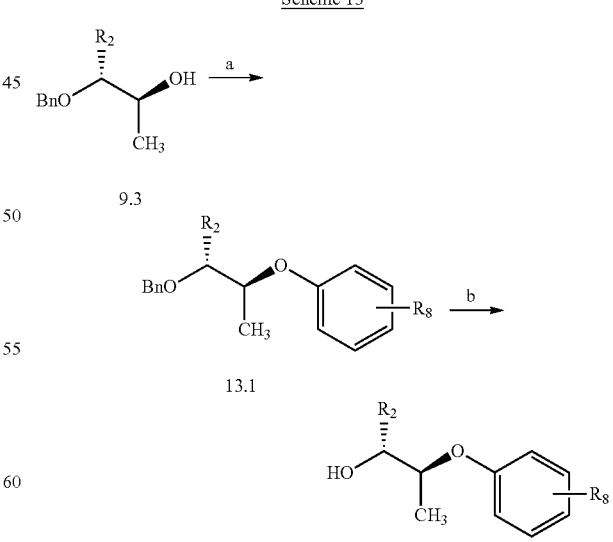

Compounds of Formula 14.7. wherein $R_4$ and $R_8$ are as previously defined, can be prepared by the method shown in Scheme 14, steps a-f. The compound of Formula 14.1, wherein $R_4$ is as previously defined, can be treated with an oxidant, such as ozone gas, in the presence of a base, such as sodium bicarbonate, followed by a hydride source, such as sodium hydride, in a solvent mixture of about 1:32 methanol:dichloromethane to 1:3 methanol:dichloromethane, at a temperature of about −78° C. to ambient temperature, to afford compounds of Formula 14.2, wherein $R_4$ is as previously defined, as shown in a. The compound of Formula 14.2, wherein $R_4$ is as previously defined, can be treated with a methylating agent, such as trimethyloxonium tetrafluoroborate, and a proton scavenger, such as $N_1,N_1,N_8,N_8$-tetramethylnaphthalene-1,8-diamine, in a solvent such as dichloromethane, at a temperature of about 23° C., to afford compounds of Formula 14.3, wherein $R_4$ is as previously defined, as shown in b. Alternatively, the compound of Formula 14.2, wherein $R_4$ is as previously defined, can be treated with an allylating reagent, such as allyl bromide, in the presence of a base, such as sodium hydride, and a catalyst, such as tetrabutylammonium iodide, in a solvent, such as dimethylformamide, at a temperature of about 0° C. to ambient temperature, to afford compounds of Formula 14.4, wherein $R_4$ and $R_{10}$ are as previously defined, as shown in c. Alternatively, the compound of Formula 14.2, wherein $R_4$ is as previously defined, can be treated with an alkylating reagent, such as benzyl bromide, in the presence of a base, such as sodium hydride, and a catalyst, such as tetrabutylammonium iodide, in a solvent, such as dimethylformamide, at a temperature of about 0° C. to ambient temperature, to afford compounds of Formula 14.5, wherein $R_4$ and $R_{10}$ are as previously defined, as shown in d. Alternatively, the compound of Formula 14.2 can be treated with a base, such as N-cyclohexyl-N-methylcyclohexanamine, in the presence of triphenylbismuth(V) acetate and copper(II) acetate in a solvent, such as toluene at a temperature of about 23° C. to 40° C. to afford compounds of Formula 14.6, wherein $R_4$ and $R_{10}$ is as previously defined, as shown in e. The compounds of Formula 14.3, 14.4, 14.5 and 14.6, wherein $R_4$ and $R_{10}$ are as previously defined, can be treated with an oxidant, such as 2,3-dichloro-5,6-dicyano-1,4-benzoquinone (DDQ), in a solvent such as DCM at a temperature of about 0° C. to ambient temperature to afford compounds of Formula 14.7, wherein $R_4$ and $R_8$ are as previously defined, as shown in f.

Scheme 14

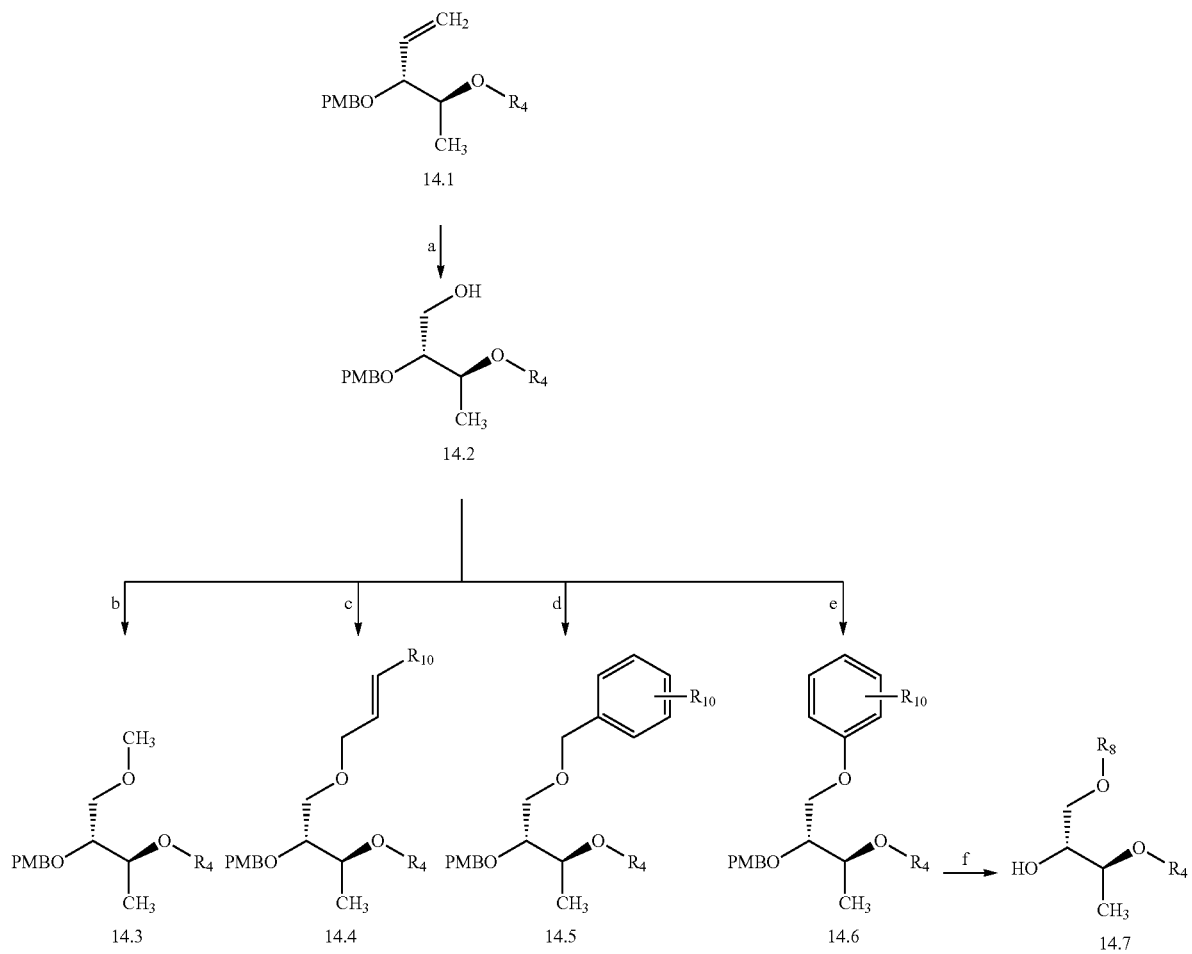

Compounds of Formula 15.3, wherein $R_4$ is as previously defined, can be prepared by the method shown in Scheme 15, steps a-c. The compound of Formula 14.1, wherein $R_4$ is as previously defined, can be treated with an oxidant, such as ozone gas, in the presence of a base, such as sodium bicarbonate, followed by a reductant, such a dimethylsulfide, in a solvent mixture such as 1:10 methanol:dichloromethane, at a temperature of about −78° C., to afford compounds of Formula 15.1, wherein $R_4$ is as previously defined, as shown in a. The compound of Formula 15.1, wherein $R_4$ is as previously defined, can be treated with a fluorinating agent, such as Deoxofluor®, in the presence of a catalyst such as methanol, in a solvent such as dichloromethane, at a temperature of about 0° C. to ambient temperature, to afford compounds of Formula 15.2, wherein $R_4$ is as previously defined, as shown in b. The compound of Formula 15.2, wherein $R_4$ is as previously defined, can be treated with an oxidant, such as 2,3-dichloro-5,6-dicyano-1,4-benzoquinone (DDQ), in a solvent such as DCM at a temperature of about 0° C. to ambient temperature to afford compounds of Formula 15.3, wherein $R_4$ is as previously defined, as shown in c.

Scheme 15

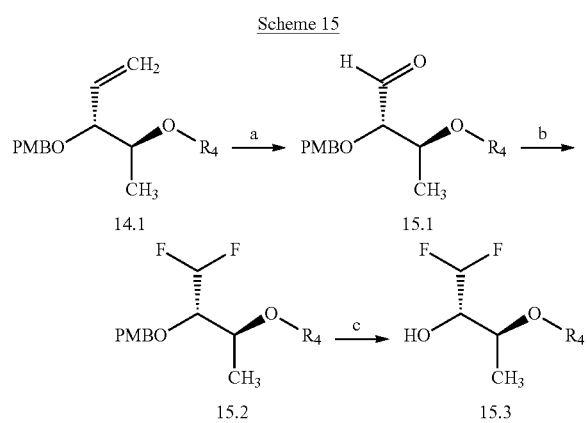

Compounds of Formula 16.2, wherein $R_2$ and $R_4$ are as previously defined, can be prepared by the method shown in Scheme 16, step a. The compound of Formula 16.1, wherein $R_2$ and $R_4$ are as previously defined, can be treated with (tert-butoxycarbonyl)-L-alanine in the presence of a peptide coupling regent, such as 1-ethyl-3-(3-dimethylaminopropyl) carbodiimide (EDCI), and a catalyst, such as dimethylamino pyridine (DMAP), in a solvent, such as DCM at a temperature of about 0° C. to ambient temperature to afford compounds of Formula 16.2, wherein $R_2$ and $R_4$ are as previously defined, as shown in a.

Scheme 16

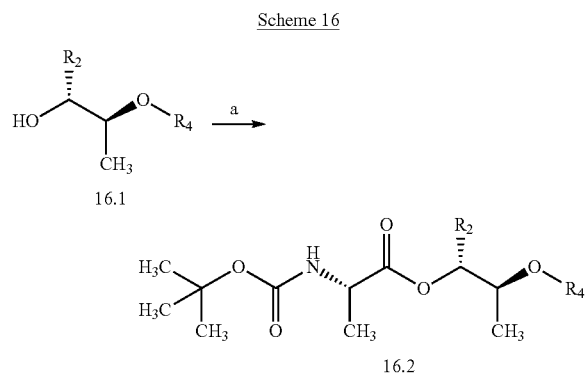

Compounds of Formula 17.2, wherein $R_2$ and $R_8$ are as previously defined, can be prepared by the method shown in Scheme 17, step a. The compound of Formula 17.1, wherein $R_2$ and $R_8$ are as previously defined, can be treated with a hydrogenation catalyst, such as palladium on carbon, under an atmosphere of hydrogen in a solvent such as ethyl acetate at a temperature of about ambient temperature to afford compounds of Formula 17.2, wherein $R_2$ and $R_8$ are as previously defined, as shown in a.

Scheme 17

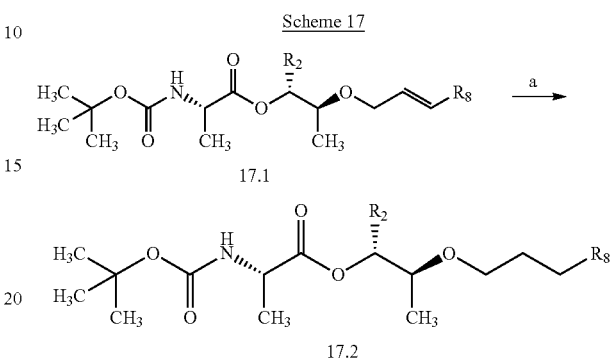

Compounds of Formula 18.2, wherein $R_2$ and $R_4$ are as previously defined, can be prepared by the method shown in Scheme 18, step a. The compound of Formula 18.1, wherein $R_2$ and $R_4$ are as previously defined, can be treated with an acid, such as 4M HCl in dioxane or trifluoroacetic acid (TFA), in a solvent such as DCM at a temperature of about ambient temperature to afford compounds of Formula 18.2, wherein $R_2$ and $R_4$ are as previously defined, as shown in a.

Scheme 18

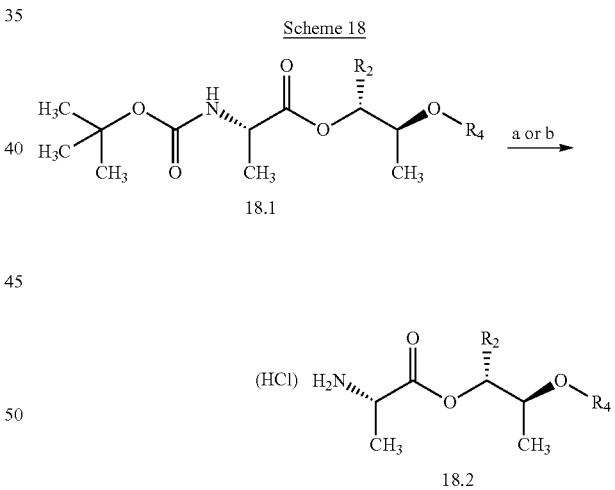

Compounds of Formula 19.2, wherein $R_2$, $R_4$ and $R_6$ are as previously defined, can be prepared by the method shown in Scheme 19, step a. The compound of Formula 18.2, wherein $R_2$ and $R_4$ are as previously defined, can be treated with compounds of Formula 19.1, wherein $R_6$ is as previously defined, in the presence of a base, such as diisopropylethylamine (DIPEA), and a peptide coupling reagent, such as benzotriazol-1-yl-oxytripyrrolidinophosphonium hexafluorophosphate (PyBOP), in an halogenated solvent like DCM at a temperature of about ambient temperature to afford compounds of Formula 19.2, wherein $R_2$, $R_4$ and $R_6$ are as previously defined, as shown in a.

Scheme 19

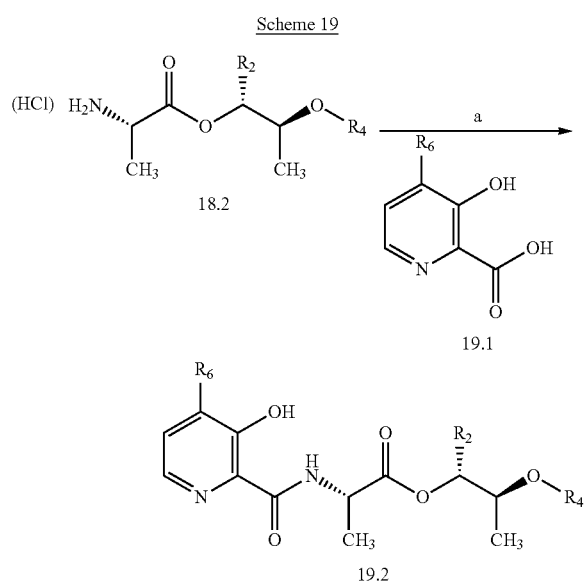

Compounds of Formula 20.1, wherein $R_2$, $R_4$, $R_6$ and $R_7$ are as previously defined, can be prepared by the method shown in Scheme 20, step a. The compound of Formula 19.2, wherein $R_2$, $R_4$, and $R_6$ are as previously defined can be treated with an appropriate alkyl halide with or without a reagent such as sodium iodide (NaI) and an alkali carbonate base, such as sodium carbonate ($Na_2CO_3$) or potassium carbonate ($K_2CO_3$), in a solvent like acetone at a temperature of about 50° C., or by treatment with an acyl halide in the presence of an amine base, such as pyridine, triethylamine ($Et_3N$), DMAP, or mixtures thereof, in an aprotic solvent such as DCM, at a temperature of about 23° C., to afford compounds of Formula 20.1, wherein $R_2$, $R_4$, $R_6$ and $R_7$ are as previously defined, as shown in a.

Scheme 20

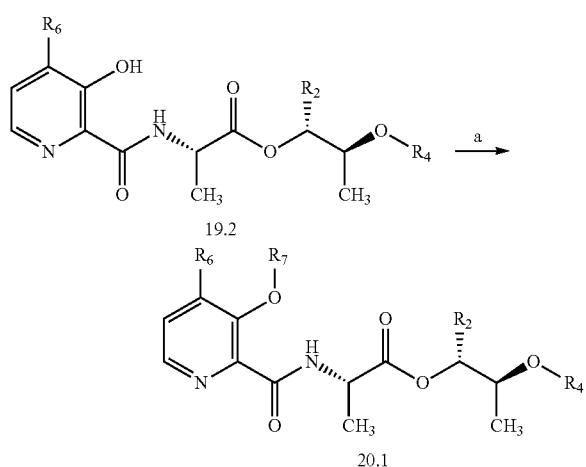

EXAMPLES

The chemistry in the following examples may be conducted using either enantiomer of 2-((tert-butoxycarbonyl)amino)propanoic acid (Boc-Ala-OH) or either protected (PMB or Bn) enantiomer of ethyl lactate.

Example 1A: Preparation of ethyl (S)-2-phenoxypropanoate

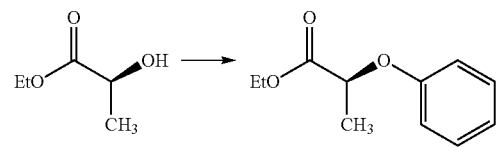

A 250 mL round-bottom flask was charged with triphenylbismuth(V) acetate (9.22 g, 16.51 mmol) and copper(II) acetate (0.231 g, 1.270 mmol) and purged with $N_2$ gas. Anhydrous toluene (85 mL) was then added, followed by (S)-ethyl 2-hydroxypropanoate (1.456 mL, 12.70 mmol) and N-cyclohexyl-N-methylcyclohexanamine (3.13 mL, 14.60 mmol). The resulting blue/green reaction was then heated to 40° C. and stirred for 96 hours (h). The reaction was cooled to room temperature (rt) and filtered through a plug of Celite®. The filter cake was washed with DCM, and then concentrated to afford a dark yellow oil. The oil was purified by flash column chromatography (silica gel ($SiO_2$), 0→10% ethyl acetate in hexanes) to afford the title compound (2.43 g, 98%) as a clear, colorless oil: $^1$H NMR (400 MHz, $CDCl_3$) δ 7.31-7.23 (m, 2H), 6.96 (tt, J=7.3, 1.1 Hz, 1H), 6.92-6.83 (m, 2H), 4.74 (q, J=6.8 Hz, 1H), 4.21 (q, J=7.1 Hz, 2H), 1.61 (d, J=6.8 Hz, 3H), 1.24 (t, J=7.1 Hz, 3H); $^{13}$C NMR (101 MHz, $CDCl_3$) δ 172.24, 157.64, 129.51, 121.55, 115.16, 72.66, 61.23, 18.57, 14.12; IR (thin film) 2986, 1753, 1733, 1494, 1239, 1134, 752 $cm^{-1}$.

Example 1B: Preparation of (S)-ethyl 2-((triisopropylsilyl)oxy)propanoate

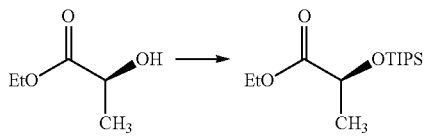

In a 500 mL round-bottom flask, (9-ethyl 2-hydroxypropanoate (9.71 mL, 85 mmol) and imidazole (13.83 g, 203 mmol) were dissolved in DCM (220 mL) under $N_2$ and cooled to 0° C. in an ice/water bath. Chlorotriisopropylsilane (21.74 mL, 102 mmol) was then added via syringe over 30 minutes (min). The reaction mixture was allowed to warm to rt and was stirred overnight. After 18 h, TLC indicated consumption of starting material. The reaction mixture was poured into a separatory funnel and washed with $H_2O$ (100 mL), saturated aqueous $NaHCO_3$ (100 mL), brine (100 mL), 1M HCl (100 mL), and then finally brine (100 mL). The organic layer was passed through a phase separator and concentrated to afford a clear, colorless oil. The oil was purified by flash column chromatography (silica gel ($SiO_2$), 0→10% ethyl acetate in hexanes) to afford the title compound (21.68 g, 93%) as a clear, colorless oil: $^1$H NMR (400 MHz, $CDCl_3$) δ 4.41 (q, J=6.7 Hz, 1H), 4.18 (qd, J=7.1, 2.7 Hz, 2H), 1.43 (d, J=6.7 Hz, 3H), 1.28 (t, J=7.1 Hz, 3H), 1.17-0.97 (m, 21H); $^{13}$C NMR (101 MHz, CDCl$_3$) δ 174.23, 68.55, 60.66, 21.80, 17.85, 14.22, 12.16.

Example 1C: Preparation of ethyl (S,E)-2-((4,4,4-trifluorobut-2-en-1-yl)oxy)propanoate

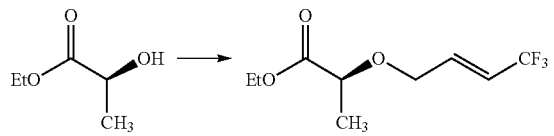

Ethyl (S)-2-hydroxypropanoate (0.971 mL, 8.47 mmol) was dissolved in dry THF (42.3 mL). Pd$_2$(dba)$_3$ (0.194 g, 0.212 mmol) and dppf (0.235 g, 0.423 mmol) were added and the mixture was heated to reflux. (E)-tert-butyl (4,4,4-trifluorobut-2-en-1-yl) carbonate (2.87 g, 12.70 mmol) was then added and the reaction was monitored until complete by TLC. The reaction was cooled to rt and carefully concentrated to afford an oil. The oil was purified by flash column chromatography (silica gel (SiO$_2$), 0→10% MTBE in hexanes) to afford the title compound (1.59 g, 79%) as a clear, colorless oil: $^1$H NMR (400 MHz, CDCl$_3$) δ 6.47-6.37 (m, 1H), 6.03-5.91 (m, 1H), 4.34-4.16 (m, 3H), 4.11-3.97 (m, 2H), 1.45 (d, J=6.8 Hz, 3H), 1.29 (t, J=7.1 Hz, 3H); $^{13}$C NMR (126 MHz, CDCl$_3$) δ 172.67, 135.95 (q, J=6.4 Hz), 123.01 (q, J=269.2 Hz), 118.98 (q, J=34.1 Hz), 75.01, 67.71, 61.08, 18.53, 14.20; IR (thin film) 2988, 1742, 1686, 1302, 1264, 1202, 1112, 1087, 1018, 959 cm$^{-1}$.

Example 1D: Preparation of methyl ethyl (S)-2-((4-methoxybenzyl)oxy)propanoate

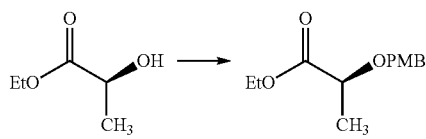

In a 500 mL round-bottom flask, a solution of (S)-ethyl 2-hydroxypropanoate (10.15 mL, 89 mmol) was prepared in DCM (89 mL). To this solution was added 4-methoxybenzyl 2,2,2-trichloroacetimidate (28.9 g, 102 mmol) followed by camphorsulfonic acid (2.065 g, 8.89 mmol), and the resulting orange/brown colored reaction was stirred at rt for 72 h. Hexanes (100 mL) was added, and the reaction mixture was stirred for 30 min. The precipitated solids were filtered, and the filtrate was concentrated to afford an oil. The oil was again diluted with 200 mL DCM/Hexanes (1:1). The mixture was stirred at rt for 30 min. The solids were filtered, and the filtrate was washed with saturated aqueous NaHCO$_3$ (100 mL), followed by brine (100 mL). The organic layer was dried over Na$_2$SO$_4$, filtered and concentrated to afford a brown oil. The oil was purified by flash column chromatography (silica gel (SiO$_2$), 0→10% ethyl acetate in hexanes) to afford the title compound (11.96 g, 56%) as a pale yellow oil: $^1$H NMR (400 MHz, CDCl$_3$) δ 7.34-7.24 (m, 2H), 6.91-6.84 (m, 2H), 4.62 (d, J=11.3 Hz, 1H), 4.39 (d, J=11.2 Hz, 1H), 4.21 (qd, J=7.1, 2.4 Hz, 2H), 4.03 (q, J=6.8 Hz, 1H), 3.80 (s, 3H), 1.41 (d, J=6.9 Hz, 3H), 1.29 (t, J=7.1 Hz, 3H); $^{13}$C NMR (101 MHz, CDCl$_3$) δ 173.41, 159.37, 129.68, 113.83, 73.74, 71.66, 60.84, 55.31, 18.76, 14.28; IR (thin film) 2984, 1730, 1513, 1247, 1198, 1031, 822 cm$^{-1}$.

Example 1E: Preparation of ethyl (S)-2-(benzyloxy)propanoate

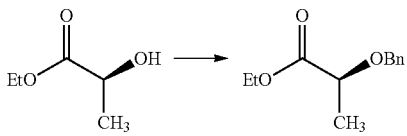

In a 500 mL round-bottom flask, a solution of (S)-ethyl 2-hydroxypropanoate (11.65 mL, 102 mmol) was prepared in anhydrous DCM (203 mL). To this solution was added (bromomethyl)benzene (18.12 mL, 152 mmol) followed by silver(I) oxide (24.72 g, 107 mmol) and potassium iodide (1.686 g, 10.16 mmol). The resultant black reaction mixture was heated to reflux and stirred overnight. After 24 h, TLC indicated nearly complete consumption of starting material. The reaction mixture was filtered through a pad of Celite®, flushed with DCM, and concentrated to an oil. The oil was purified by flash column chromatography (silica gel (SiO$_2$), 0→5% ethyl acetate in hexanes) to afford the title compound (11.93 g, 56%) as a clear, colorless oil: $^1$H NMR (400 MHz, CDCl$_3$) δ 7.48-7.14 (m, 5H), 4.69 (d, J=11.6 Hz, 1H), 4.45 (d, J=11.6 Hz, 1H), 4.21 (qd, J=7.1, 2.6 Hz, 2H), 4.05 (q, J=6.9 Hz, 1H), 1.43 (d, J=6.9 Hz, 3H), 1.29 (t, J=7.1 Hz, 3H); $^{13}$C NMR (101 MHz, CDCl$_3$) δ 173.27, 137.63, 128.43, 127.98, 127.84, 74.09, 72.00, 60.85, 18.74, 14.27; IR (thin film) 2984, 1743, 1454, 1196, 1140, 1064, 1024, 736, 697 cm$^{-1}$.

Example 1F, Step 1: Preparation of tris(4-fluoro-2-methylphenyl)bismuthane

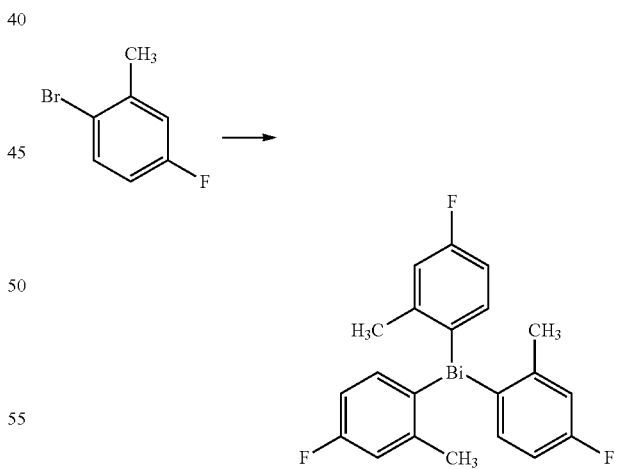

In a 250 mL round-bottom flask, a solution of 1-bromo-4-fluoro-2-methylbenzene (5.24 mL, 42.3 mmol) was prepared in THF (171 mL) and cooled to −78° C. in a dry ice/acetone bath. After ~10 min, butyllithium (2.5 M in hexanes, 17.8 mL, 44.4 mmol) was added dropwise via syringe, and the resulting clear, colorless reaction was stirred for 1 hr. After 1 hr, trichlorobismuthane (4.30 g, 13.63 mmol) was added as a solution in THF (71 mL) via syringe, and the reaction was stirred at −78° C. for 1 hr, and then warmed to rt and stirred overnight. After 18 h, the reaction was concentrated and the remaining residue was extracted with toluene (200 mL) and a yellowish-white solid was removed via filtration. The filtrate was then concentrated to dryness to afford the title compound (7.25 g, 99%) as an off white solid which was used directly in the next step without further purification: ¹H NMR (400 MHz, CDCl₃) δ 7.40 (dd, J=8.2, 6.7 Hz, 3H), 7.04 (dd, J=10.3, 2.7 Hz, 3H), 6.78 (td, J=8.6, 2.7 Hz, 3H), 2.41 (s, 9H); ¹⁹F NMR (376 MHz, CDCl₃) δ −113.91.

Example 1F, Step 2: Preparation of ethyl (S)-2-(4-fluoro-2-methylphenoxy)propanoate

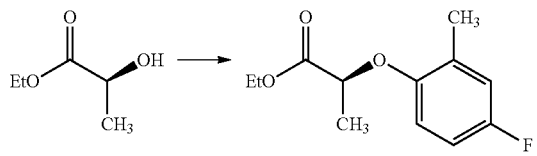

A solution of tris(4-fluoro-2-methylphenyl)bismuthane (3.41 g, 6.35 mmol) was prepared in DCM (21.16 mL) at room temperature, and peracetic acid (1.225 mL, 7.20 mmol) was then added via syringe slowly over 5 min. Bubbling was observed, and reaction became a light orange color. The resulting reaction was allowed to stir at rt for 30 min. After 30 min, ethyl (S)-2-hydroxypropanoate (0.485 mL, 4.23 mmol) and copper(II) acetate (0.154 g, 0.847 mmol) were added, the flask was fitted with a reflux condenser, and the opaque blue/green reaction mixture was heated to 45° C. and stirred overnight. After 20 h, TLC indicated ~75% consumption of starting material and conversion to several higher R_f spots. The reaction was cooled to room temperature and then filtered through a plug of celite, filtering with DCM (2×10 mL), and then concentrated to afford an oil. The oil was purified by flash column chromatography (silica gel (SiO₂), 0→20% ethyl acetate in hexanes) to afford the title compound (318.8 mg, 33%) as a pale yellow oil: ¹H NMR (400 MHz, CDCl₃) δ 6.85 (dd, J=9.0, 3.1 Hz, 1H), 6.76 (td, J=8.5, 3.1 Hz, 1H), 6.63 (dd, J=8.9, 4.6 Hz, 1H), 4.66 (q, J=6.8 Hz, 1H), 4.20 (qd, J=7.1, 1.4 Hz, 2H), 2.26 (s, 3H), 1.61 (d, J=6.8 Hz, 3H), 1.24 (t, J=7.1 Hz, 3H); ¹⁹F NMR (376 MHz, CDCl₃) δ −123.28; ¹³C NMR (101 MHz, CDCl₃) δ 172.18, 157.40 (d, J=239.0 Hz), 152.11 (d, J=2.3 Hz), 129.75 (d, J=7.7 Hz), 117.58 (d, J=22.8 Hz), 113.42 (d, J=8.5 Hz), 112.37 (d, J=22.8 Hz), 73.81, 61.19, 18.64, 16.40 (d, J=1.3 Hz), 14.12; IR (thin film) 3350, 2987, 1750, 1496, 1191, 1134, 718 cm⁻¹; HRMS-ESI (m/z) calc'd for [C₁₂H₁₆FO₃]⁺, 227.1078; found, 227.1089.

Example 2: Preparation of (S)-2-((triisopropylsilyl)oxy)propanal

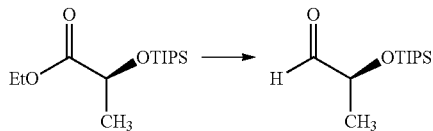

In a 1 L round-bottom flask, (9-ethyl 2-((triisopropylsilyl)oxy)propanoate (21.68 g, 79 mmol) was dissolved in DCM (395 mL) under N₂ and cooled to −78° C. in an dry ice/acetone bath. Diisobutylaluminum hydride (1 M in hexanes, 158 mL, 158 mmol) was added via syringe over 4 h. The reaction was stirred at −78° C. for an additional 30 min. After 30 min, ethyl acetate (75 mL) was added to quench the reaction, and the reaction mixture was warmed to 0° C. in an ice/water bath. A solution of saturated aqueous potassium sodium tartrate (~200 mL) was added, and the reaction was vigorously stirred overnight, slowly warming to rt as the ice bath melted. After 18 h, the biphasic mixture was poured into a separatory funnel and the layers were separated. The aqueous layer was extracted with DCM (3×150 mL). The combined organic layers were passed through a phase separator and concentrated to afford a clear, colorless oil. The oil was purified by flash column chromatography (silica gel (SiO₂), 0→20% ethyl acetate in hexanes) to afford the title compound (15.85 g, 87%) as a clear, colorless oil: ¹H NMR (400 MHz, CDCl₃) δ 9.66 (d, J=1.7 Hz, 1H), 4.18 (qd, J=6.8, 1.7 Hz, 1H), 1.31 (d, J=6.8 Hz, 3H), 1.11-1.01 (m, 21H); ¹³C NMR (101 MHz, CDCl₃) δ 204.54, 73.83, 18.95, 17.89, 12.14.

Example 3A: Preparation of (3R,4S)-2-methyl-4-phenoxypentan-3-ol

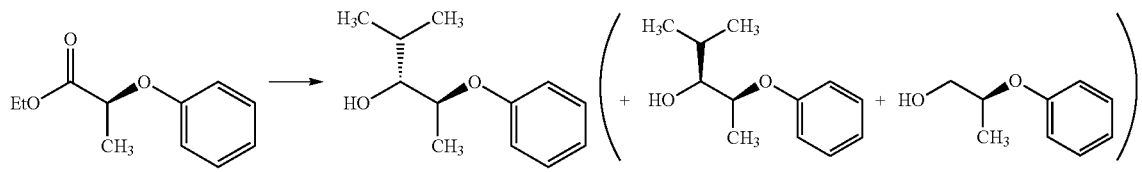

In a 250 mL flask, a solution of isopropylmagnesium bromide (2M in Et₂O, 9.01 mL, 18.02 mmol) and lithium borohydride (2M in THF, 5.86 mL, 11.71 mmol) was prepared in THF (33 mL). The reaction was cooled to 0° C. in an ice bath. After ~10 min, ethyl (S)-2-phenoxypropanoate (1.75 g, 9.01 mmol) was added dropwise via syringe as a solution in THF (9 mL w/ 2×1.5 mL washes) over 3 h via syringe pump. The resultant pale yellow clear reaction mixture was stirred overnight, slowly warming to rt as the ice bath melted. The reaction was quenched with water (100 mL, caution GAS EVOLUTION) and diluted with Et₂O (100 mL). The layers were separated and the aqueous layer was extracted with Et₂O (3×100 mL). The combined organic layers were dried over MgSO₄, filtered and concentrated to afford an oil. The oil was purified by flash column chromatography (SiO₂, 0→30% ethyl acetate in hexanes) to afford the title compound (849 mg, 49%) as a clear, colorless oil: ¹H NMR (400 MHz, CDCl₃) δ 7.34-7.26 (m, 2H), 6.95 (tt, J=7.4, 1.1 Hz, 1H), 6.93-6.87 (m, 2H), 4.48 (qd, J=6.2, 3.8

Hz, 1H), 3.54 (dt, J=7.9, 3.4 Hz, 1H), 2.09 (d, J=3.1 Hz, 1H), 1.79 (dp, J=7.9, 6.7 Hz, 1H), 1.30 (d, J=6.3 Hz, 3H), 1.03 (d, J=6.6 Hz, 3H), 0.95 (d, J=6.8 Hz, 3H); $^{13}$C NMR (101 MHz, CDCl$_3$) δ 157.39, 129.58, 121.08, 116.04, 78.00, 74.79, 29.87, 18.89, 18.71, 13.11; IR (thin film) 3425, 2955, 1598, 1493, 1240, 1055, 752 cm$^{-1}$. Also isolated (3S,4S)-2-methyl-4-phenoxypentan-3-ol (216 mg, 1.11 mmol, 12% yield) as a clear, colorless oil: $^1$H NMR (300 MHz, CDCl$_3$) δ 7.34-7.21 (m, 2H), 7.00 6.86 (m, 3H), 4.38 (p, J=6.1 Hz, 1H), 3.36 (q, J=5.1 Hz, 1H), 2.35 (d, J=5.1 Hz, 1H), 1.87 (pd, J=6.8, 5.0 Hz, 1H), 1.28 (d, J=6.2 Hz, 3H), 1.04-0.95 (m, 6H); $^{13}$C NMR (101 MHz, CDCl$_3$) δ 157.73, 129.58, 121.18, 116.15, 79.40, 75.37, 30.07, 20.00, 16.60, 16.04; IR (thin film) 3434, 2955, 1598, 1494, 1240, 1051, 752 cm$^{-1}$. Also isolated (S)-2-phenoxypropan-1-ol (44.4 mg, 0.292 mmol, 3.2% yield) as a clear, colorless oil: $^1$H NMR (400 MHz, CDCl$_3$) δ 7.33-7.25 (m, 2H), 7.00-6.90 (m, 3H), 4.50 (pd, J=6.3, 3.8 Hz, 1H), 3.81-3.66 (m, 2H), 2.12 (s, 1H), 1.27 (d, J=6.3 Hz, 3H); $^{13}$C NMR (101 MHz, CDCl$_3$) δ 157.73, 129.58, 121.22, 116.18, 74.77, 66.27, 15.84; IR (thin film) 3381, 2932, 1598, 1493, 1240, 1051, 752 cm$^{-1}$.

Example 3B: Preparation of (3R,4S)-4-((triisopropylsilyl)oxy)pent-1-en-3-ol

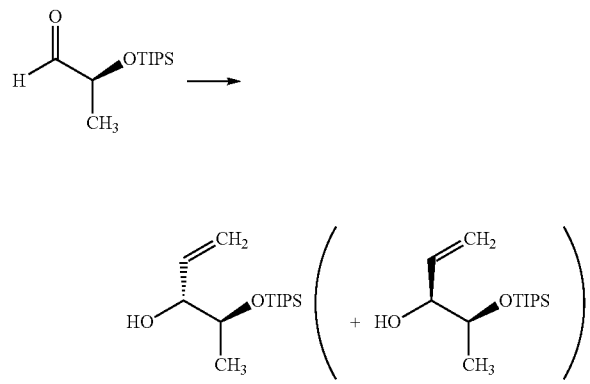

A solution of (S)-2-((triisopropylsilyl)oxy)propanal (5.0 g, 21.70 mmol) in Et$_2$O (108 mL) was prepared in a 250 mL round bottom flask and cooled to −78° C. in a dry ice/acetone bath under an atmosphere of N$_2$. Vinylmagnesium bromide (1.0 M in THF, 23.87 mL, 23.87 mmol) was then added via syringe over 30 min. The reaction mixture was stirred at −78° C. for 30 min, and then was allowed to slowly warm to rt over 2 h. The reaction was poured over saturated aqueous NH$_4$Cl (200 mL) and extracted with Et$_2$O (3×100 mL). The combined organic layers were dried over MgSO$_4$, filtered, and concentrated to afford a pale yellow oil. The oil was purified by flash column chromatography (SiO$_2$, 0→20% ethyl acetate in hexanes) to afford the title compound (4.30 g, 77%, d.r.~6:1) as a clear, colorless oil: $^1$H NMR (300 MHz, CDCl$_3$) δ 5.80 (ddd, J=17.0, 10.6, 6.0 Hz, 1H), 5.31 (dt, J=17.3, 1.7 Hz, 1H), 5.20 (dt, J=10.6, 1.6 Hz, 1H), 4.16 (dddt, J=6.4, 4.8, 3.2, 1.8 Hz, 1H), 4.00 (qd, J=6.4, 3.5 Hz, 1H), 2.45 (d, J=3.3 Hz, 1H), 1.12 (d, J=6.4 Hz, 3H), 1.08 (s, 21H); $^{13}$C NMR (101 MHz, CDCl$_3$) δ 136.42, 116.31, 71.40, 60.35, 21.00, 18.02, 14.17, 12.38; IR (neat) 3483, 2943, 2866, 1463, 676 cm$^{-1}$; HRMS-ESI (m/z) calc'd for [C$_{14}$H$_{30}$NaO$_2$Si]$^+$, 281.1907; found, 281.1920.

Example 3C: Preparation of (2S,3R)-2-((triisopropylsilyl)oxy)hex-5-en-3-ol

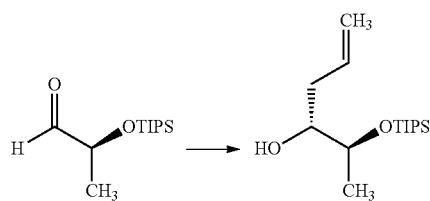

A 500 mL round bottom flask was charged with (+)-Ipc$_2$-allylborane (1M in pentane, 25.0 mL, 25.00 mmol) under N$_2$ and diluted with Et$_2$O (100 mL). The resultant clear, colorless solution was cooled to −78° C. in an acetone/dry ice bath. (S)-2-((triisopropylsilyl)oxy)propanal (4.61 g, 20.01 mmol) was added as a solution in anhydrous Et$_2$O (60 mL) via syringe over 1.5 h. The clear, colorless reaction was cooled for an additional 1.5 h at −78° C., after which TLC indicated consumption of starting material. MeOH (50 mL) was then added, and the reaction was stirred for 5 min at −78° C. pH 7 buffer (70 mL) was added, and the reaction was warmed to 0° C. in an ice/water bath. H$_2$O$_2$ (30%, 60 mL) was then added, and the resulting biphasic reaction mixture was vigorously stirred at 0° C. for 2.5 h, and then warmed to room temperature as the ice melted and stirred for 30 h. The layers were separated, and the aqueous phase was extracted with Et$_2$O (3×100 mL). The aqueous layer was carefully quenched with saturated aqueous Na$_2$S$_2$O$_3$ on ice until KI-starch test paper indicated the disappearance of residual H$_2$O$_2$. The combined organic layers were dried over MgSO$_4$, filtered, and concentrated to a clear oil. The oil was purified by flash column chromatography (SiO$_2$, 0→15% ethyl acetate in hexanes) to afford the title compound (5.00 g, 92%) as a clear, light rose colored oil: $^1$H NMR (400 MHz, CDCl$_3$) δ 5.85 (ddt, J=17.2, 10.2, 7.0 Hz, 1H), 5.22-4.97 (m, 2H), 3.93 (qd, J=6.2, 3.3 Hz, 1H), 3.70 (ddt, J=8.3, 5.7, 2.9 Hz, 1H), 2.34 (d, J=2.6 Hz, 1H), 2.30-2.09 (m, 2H), 1.14 (d, J=6.3 Hz, 3H), 1.12-1.03 (m, 21H); $^{13}$C NMR (101 MHz, CDCl$_3$) δ 134.91, 117.07, 74.48, 70.77, 36.72, 18.06, 16.59, 12.37; IR (neat) 3480, 2943, 2866, 1463, 1067, 881 cm$^{-1}$; HRMS-ESI (m/z) calc'd for [C$_{15}$H$_{33}$O$_2$Si]$^+$, 274.2270; found, 274.2274.

Example 4A: Preparation of 1-((((2S,3R)-3-(benzyloxy)-4-methylpentan-2-yl)oxy)methyl)-4-methoxybenzene

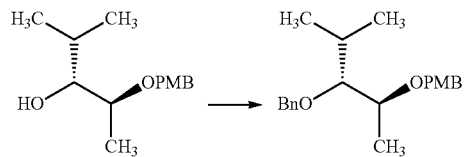

In a 250 mL round bottom flask, a suspension of sodium hydride (0.329 g, 13.72 mmol) was prepared in DMF (42.7 mL) under an atmosphere of N$_2$ and cooled to 0° C. in an ice/water bath. After 5 min, (2S,3R)-2-((4-methoxybenzyl)oxy)-4-methylpentan-3-ol (1.868 g, 7.84 mmol) was added via syringe as a solution in DMF (10 mL with 2×5 mL washes). The resultant bright yellow reaction mixture was brought to rt and was stirred for 3 h. The reaction was cooled to 0° C. and (bromomethyl)benzene (1.617 mL, 14.89 mmol) was added in one portion, followed by tetrabutylammonium iodide (0.290 g, 0.784 mmol). The reaction mixture was warmed to 40° C. and stirred overnight. The reaction was cooled to 0° C. and diethylamine (2.433 mL, 23.51 mmol) was added via syringe over 15 seconds. The pale yellow reaction was warmed to rt and was stirred for 1 h, at which point the reaction became a clear, yellow solution. After 1 h, the reaction was quenched with saturated aqueous NH$_4$Cl (200 mL) and extracted with Et$_2$O (3×200 mL). The combined organic layers were washed with brine (200 mL), dried over MgSO$_4$, filtered, and concentrated to afford a yellow oil. The oil was purified by flash column chromatography (SiO$_2$, 0→20% ethyl acetate in hexanes) to afford the title compound (1.73 g, 67%) as a clear, colorless oil: $^1$H NMR (400 MHz, CDCl$_3$) δ 7.39-7.29 (m, 4H), 7.29-7.22 (m, 3H), 6.90-6.84 (m, 2H), 4.80 (d, J=11.3 Hz, 1H), 4.58 (d, J=11.3 Hz, 1H), 4.54 (d, J=11.4 Hz, 1H), 4.43 (d, J=11.4 Hz, 1H), 3.80 (s, 3H), 3.65 (qd, J=6.3, 4.5 Hz, 1H), 3.24 (dd, J=6.2, 4.4 Hz, 1H), 1.88 (dq, J=13.4, 6.7 Hz, 1H), 1.26 (d, J=6.2 Hz, 3H), 0.96 (d, J=6.7 Hz, 3H), 0.92 (d, J=6.9 Hz, 3H); $^{13}$C NMR (101 MHz, CDCl$_3$) δ 159.08, 139.27, 131.04, 129.09, 128.21, 127.81, 127.31, 113.77, 86.75, 76.06, 74.59, 70.33, 55.29, 30.11, 20.03, 18.44, 15.04; IR (thin film) 2959, 2871, 1513, 1247, 1099, 1066, 1036 cm$^{-1}$.

Example 4B: Preparation of triisopropyl(((2S,3R)-3-((4-methoxybenzyl)oxy)pent-4-en-2-yl)oxy)silane

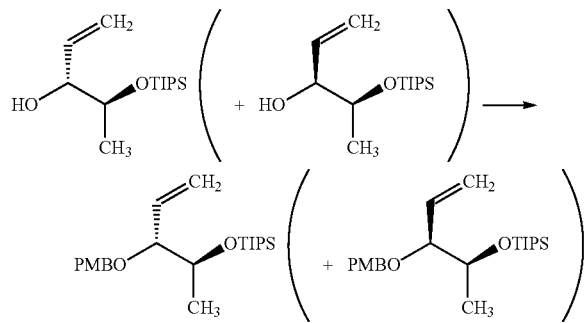

In a 250 mL round bottom flask, a suspension of sodium hydride (1.165 g, 29.1 mmol) was prepared in DMF (93 mL) under an atmosphere of N$_2$ and cooled to 0° C. in an ice/water bath. After 5 min, (3R,4S)-4-((triisopropylsilyl)oxy)pent-1-en-3-ol (4.301 g, 16.64 mmol, d.r. ~6:1) was added via syringe as a solution in DMF (20 mL with 2×10 mL washes). The resultant bright yellow reaction mixture was brought to rt and was stirred for 3 h. The reaction was cooled to 0° C. and 4-methoxybenzyl bromide (4.61 mL, 31.6 mmol) was added in one portion, followed by tetrabutylammonium iodide (0.615 g, 1.664 mmol), after which the reaction underwent a distinct color change to light orange. The reaction mixture was warmed to rt and was stirred overnight. After 20 h, TLC indicated consumption of starting material. The reaction was cooled to 0° C. and diethylamine (5.16 mL, 49.9 mmol) was added via syringe over 15 seconds. The pale yellow reaction was warmed to rt and was stirred for 1 h, at which point the reaction became a clear, yellow solution. After 1 h, the reaction was quenched with saturated aqueous NH$_4$Cl (150 mL) and extracted with Et$_2$O (3×150 mL). The combined organic layers were washed with brine (100 mL), dried over MgSO$_4$, filtered, and concentrated to afford a yellow oil. The oil was purified by flash column chromatography (SiO$_2$, 0→15% MTBE in petroleum ether) to afford the title compound (4.063 g, 65%, d.r.~6:1) as a clear, colorless oil: $^1$H NMR (400 MHz, CDCl$_3$) δ 7.34-7.19 (m, 2H), 6.92-6.79 (m, 2H), 5.84 (ddd, J=17.1, 10.5, 7.4 Hz, 1H), 5.43-5.08 (m, 2H), 4.55 (d, J=11.5 Hz, 1H), 4.38 (d, J=11.5 Hz, 1H), 3.98 (qd, J=6.3, 4.5 Hz, 1H), 3.80 (s, 3H), 3.63 (ddt, J=7.5, 4.4, 1.0 Hz, 1H), 1.19 (d, J=6.2 Hz, 3H), 1.10-0.98 (m, 21H); $^{13}$C NMR (101 MHz, CDCl$_3$) δ 158.96, 136.47, 131.02, 129.29, 118.19, 113.62, 85.07, 71.35, 70.35, 55.26, 19.87, 18.15, 12.55; IR (neat) 2942, 2865, 1513, 1246, 1039, 677 cm$^{-1}$; HRMS-ESI (m/z) calc'd for [C$_{22}$H$_{38}$NaO$_3$Si]$^+$, 401.24824; found, 401.24711.

Example 4C: Preparation of methyl (R)-2-((tert-butyldimethylsilyl)oxy)-2-phenylacetate

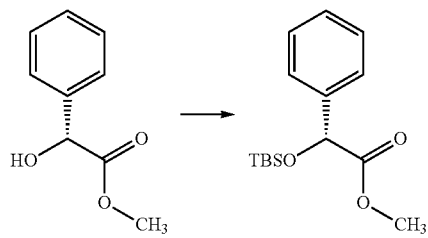 [SMILES: COC(=O)[C@H](O)c1ccccc1 ; COC(=O)[C@H](O[Si](C)(C)C(C)(C)C)c1ccccc1]

A solution of ethyl (R)-2-hydroxy-2-phenylacetate (5.00 g, 30.1 mmol), TBSCl (6.80 g, 45.1 mmol), and imidazole (4.10 g, 60.2 mmol) was prepared in DMF (31.7 mL) and stirred overnight at rt. After 20 h, the solution was diluted with Et$_2$O and water. The organic phase was washed with brine, dried over Na$_2$SO$_4$, and concentrated to an oil. The oil was purified by flash column chromatography (SiO$_2$, 0→5% ethyl acetate in hexanes) to afford the title compound (7.53 g, 85%) as a clear, colorless oil: $^1$H NMR (300 MHz, CDCl$_3$) δ 7.42-7.31 (m, 2H), 7.28-7.17 (m, 3H), 5.13 (s, 1H), 3.57 (s, 3H), 0.81 (s, 9H), 0.00 (s, 3H), −0.07 (s, 3H); $^{13}$C NMR (126 MHz, CDCl$_3$) δ 172.61, 139.11, 128.33, 128.09, 126.33, 74.39, 52.18, 25.71, 18.35, −5.09, −5.16; IR (thin film) 2952, 2929, 2886, 2857, 1758, 1737, 1472, 1253, 1207, 1191, 1170, 1125, 861, 836, 778, 725, 696 cm$^{-1}$; HRMS-ESI (m/z) calc'd for [C$_{15}$H$_{25}$O$_3$Si]$^+$, 281.1567; found, 281.1578.

Example 5A: Preparation of (2S,3R)-3-(benzyloxy)-4-methylpentan-2-ol

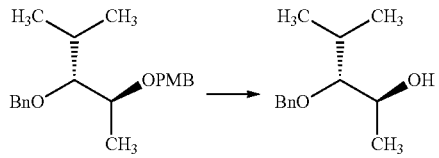

In a 250 mL flask, 1-((((2S,3R)-3-(benzyloxy)-4-methylpentan-2-yl)oxy)methyl)-4-methoxybenzene (1.7255 g, 5.25 mmol) was dissolved in acetonitrile (96 mL) and H$_2$O (9.55 mL) and was cooled to 0° C. in an ice bath. After ~5 min, ceric ammonium nitrate (14.40 g, 26.3 mmol) was added, and the orange reaction mixture was stirred at 0° C.

for 3 h. After 3 h, the mixture was quenched with saturated aqueous NaHCO$_3$ (100 mL), and then extracted with DCM (3×100 mL). The combined organic layers were poured through a phase separator and concentrated to afford a clear, colorless oil. The oil was purified by flash column chromatography (SiO$_2$, 0→50% ethyl acetate in hexanes) to afford the title compound (401 mg, 37%) as a clear, colorless oil: $^1$H NMR (400 MHz, CDCl$_3$) δ 7.39-7.22 (m, 5H), 4.66 (d, J=0.9 Hz, 2H), 3.93 (qd, J=6.4, 4.2 Hz, 1H), 3.13 (dd, J=6.4, 4.2 Hz, 1H), 1.92 (s, 1H), 1.86 (dq, J=13.5, 6.8 Hz, 1H), 1.20 (d, J=6.5 Hz, 3H), 1.03 (d, J=6.7 Hz, 3H), 0.94 (d, J=6.9 Hz, 3H); $^{13}$C NMR (101 MHz, CDCl$_3$) δ 138.91, 128.40, 127.60, 127.58, 88.50, 74.84, 68.43, 30.07, 19.94, 18.66, 18.08; IR (thin film) 3406, 2962, 1454, 1093, 1063, 734, 697 cm$^{-1}$.

Example 5B: Preparation of (2S,3R)-3-((4-methoxybenzyl)oxy)pent-4-en-2-ol

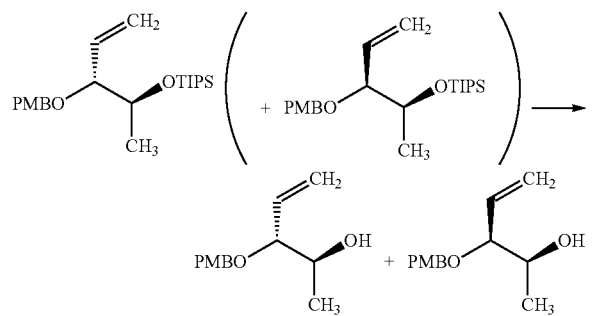

A solution of triisopropyl(((2S,3R)-3-((4-methoxybenzyl)oxy)pent-4-en-2-yl)oxy)silane (4.06 g, 10.7 mmol, d.r.~6:1) was prepared in a 250 mL round bottom flask in THF (53.7 mL) under N$_2$ and cooled to 0° C. After 5 min, TBAF (12.88 mL, 12.88 mmol) was added dropwise via syringe over 2 min. The reaction mixture was allowed to warm to rt and stirred for 4 h. The reaction was quenched with saturated aqueous NH$_4$Cl (100 mL) and extracted with Et$_2$O (3×100 mL). The combined organic layers were dried over MgSO$_4$, filtered, and concentrated to afford a clear, colorless oil. The oil was purified by flash column chromatography (SiO$_2$, 0→30% ethyl acetate in hexanes) to afford the title compound (1.272 g, 53%) as a clear, colorless oil: $^1$H NMR (400 MHz, CDCl$_3$) δ 7.25 (d, J=8.4 Hz, 2H), 6.88 (d, J=8.6 Hz, 2H), 5.82 (ddd, J=17.4, 10.4, 8.1 Hz, 1H), 5.40 (ddd, J=10.4, 1.9, 0.8 Hz, 1H), 5.30 (ddd, J=17.3, 1.9, 0.9 Hz, 1H), 4.57 (d, J=11.5 Hz, 1H), 4.31 (d, J=11.4 Hz, 1H), 3.92-3.78 (m, 4H), 3.71-3.62 (m, 1H), 2.21 (d, J=3.9 Hz, 1H), 1.13 (d, J=6.4 Hz, 3H); $^{13}$C NMR (101 MHz, CDCl$_3$) δ 159.19, 134.66, 130.34, 129.39, 120.20, 113.80, 83.96, 69.95, 69.27, 55.27, 17.94; IR (thin film) 3447, 2976, 2868, 1612, 1513, 1545, 1033, 819 cm$^{-1}$; HRMS-ESI (m/z) calc'd for [C$_{13}$H$_{18}$NaO$_3$]$^+$, 245.11482; found, 245.1134. Also isolated (2S,3S)-3-((4-methoxybenzyl)oxy)pent-4-en-2-ol (325 mg, 1.46 mmol, 14% yield) as a clear, colorless oil: $^1$H NMR (300 MHz, CDCl$_3$) δ 7.31-7.21 (m, 2H), 6.94-6.85 (m, 2H), 5.79-5.62 (m, 1H), 5.45-5.15 (m, 1H), 4.57 (d, J=11.2 Hz, 1H), 4.28 (d, J=11.1 Hz, 1H), 3.81 (s, 3H), 3.74-3.64 (m, 1H), 3.50 (t, J=7.9 Hz, 1H), 2.83-2.69 (m, 1H), 1.18 (d, J=6.2 Hz, 1H), 1.12 (d, J=6.2 Hz, 3H); IR (thin film) 3455, 2869, 1513, 1247, 1069, 1034, 820 cm$^{-1}$.

Example 5C: Preparation of (1R,2S)-1-((4-methoxybenzyl)oxy)-1-phenylpropan-2-ol

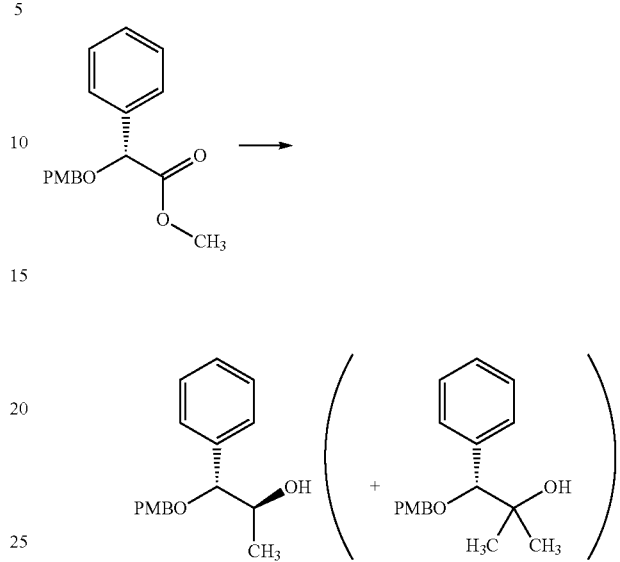

A solution of lithium borohydride (2M in THF, 3.93 mL, 7.86 mmol) and methyllithium (1.6M in THF, 3.93 mL, 6.29 mmol) was prepared in Et$_2$O (29.1 mL) and cooled to −78° C. in a dry ice/acetone bath. After ~5 min, a solution of methyl (R)-2-((4-methoxybenzyl)oxy)-2-phenylacetate (1.5 g, 5.24 mmol) dissolved in Et$_2$O (9 mL) was added slowly via addition funnel. The reaction was allowed to warm to rt slowly overnight. After 20 h, the reaction was carefully quenched with saturated aqueous NH$_4$Cl and extracted with Et$_2$O. The combined organic layers were dried over Na$_2$SO$_4$, filtered, and concentrated. The crude material was purified by flash column chromatography (SiO$_2$, 0→15% ethyl acetate in hexanes) to afford the title compound (744 mg, 50%) as a thick oil: $^1$H NMR (400 MHz, CDCl$_3$) δ 7.43-7.29 (m, 5H), 7.25-7.18 (m, 2H), 6.90-6.85 (m, 2H), 4.48 (d, J=11.3 Hz, 1H), 4.26 (d, J=5.0 Hz, 1H), 4.23 (d, J=11.3 Hz, 1H), 4.01-3.91 (m, 1H), 3.81 (s, 3H), 1.93 (s, 1H), 1.11 (d, J=6.4 Hz, 3H); $^{13}$C NMR (126 MHz, CDCl$_3$) δ 159.24, 138.27, 130.20, 129.45, 128.42, 128.02, 127.84, 113.82, 84.63, 70.82, 70.46, 55.28, 18.15; IR (thin film) 3440, 2867, 2835, 1611, 1512, 1492, 1452, 1301, 1244, 1172, 1134, 1060, 1030, 952, 818, 755, 701 cm$^{-1}$; HRMS-ESI (m/z) calc'd for [C$_{17}$H$_{20}$O$_3$Na]$^+$, 295.1305; found, 295.1300. Also isolated (R)-1-((4-methoxybenzyl)oxy)-2-methyl-1-phenylpropan-2-ol (353 mg, 1.17 mmol, 22% yield) as a thick oil: $^1$H NMR (400 MHz, CDCl$_3$) δ 7.40-7.29 (m, 5H), 7.25-7.19 (m, 2H), 6.93-6.85 (m, 2H), 4.45 (d, J=11.2 Hz, 1H), 4.23-4.15 (m, 2H), 3.81 (s, 3H), 2.53 (s, 1H), 1.16 (s, 3H), 1.09 (s, 3H); $^{13}$C NMR (126 MHz, CDCl$_3$) δ 159.23, 138.13, 130.19, 129.47, 128.36, 128.03, 127.86, 113.79, 87.70, 72.85, 70.65, 55.28, 26.17, 24.38; IR (thin film) 3418, 2973, 2933, 2866, 2835, 1611, 1512, 1452, 1370, 1351, 1244, 1170, 1085, 1062, 1028, 819, 742, 702 cm$^{-1}$; HRMS-ESI (m/z) calc'd for [C$_{18}$H$_{22}$O$_3$Na]$^+$, 309.1461; found, 309.1462.

Example 6A: Preparation of 1-methoxy-4-((((3R, 4S)-4-phenoxypent-1-en-3-yl)oxy)methyl)benzene

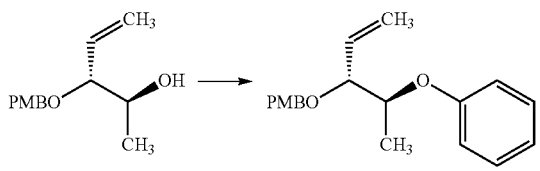

A solution of (2S,3R)-3-((4-methoxybenzyl)oxy)pent-4-en-2-ol (1.272 g, 5.72 mmol), triphenylbismuth(V) acetate (4.15 g, 7.44 mmol) and copper(II) acetate (0.104 g, 0.572 mmol) was prepared in anhydrous toluene (38.1 mL) in a 100 mL flask under an atmosphere of $N_2$. N-cyclohexyl-N-methylcyclohexanamine (1.410 mL, 6.58 mmol) was then added via syringe in one portion. The resulting blue/green reaction was heated to 40° C. yielding a pale blue/green reaction mixture. The mixture was stirred at temperature for 96 h. The reaction was cooled to rt and was filtered through a plug of Celite®, washing with DCM, and then concentrated to afford a dark yellow oil. The oil was purified by flash column chromatography ($SiO_2$, 0→20% ethyl acetate in hexanes) to afford the title compound (1.43 g, 84%) as a clear, colorless oil: $^1$H NMR (400 MHz, $CDCl_3$) δ 7.31-7.20 (m, 4H), 6.96-6.81 (m, 5H), 5.87 (ddd, J=17.5, 10.0, 7.4 Hz, 1H), 5.35 (dt, J=2.6, 1.7 Hz, 1H), 5.33-5.30 (m, 1H), 4.60 (d, J=11.6 Hz, 1H), 4.44-4.35 (m, 2H), 3.91 (ddt, J=7.4, 4.7, 1.0 Hz, 1H), 3.79 (s, 3H), 1.32 (d, J=6.3 Hz, 3H); $^{13}$C NMR (126 MHz, $CDCl_3$) δ 159.07, 157.93, 135.53, 130.48, 129.40, 129.32, 120.78, 118.99, 116.15, 113.69, 81.88, 76.17, 70.34, 55.25, 15.69; IR (thin film) 2934, 1598, 1512, 1493, 1242, 1068, 753 $cm^{-1}$.

Example 6B: Preparation of 1-(((2S,3R)-3-(benzyloxy)-4-methylpentan-2-yl)oxy)-2,4-difluorobenzene

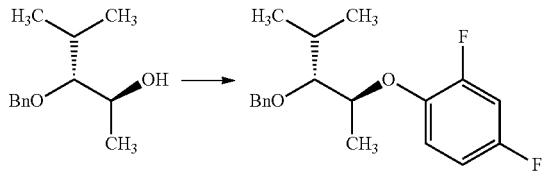 [SMILES: CC(C)[C@@H](OCc1ccccc1)[C@H](C)O ; CC(C)[C@@H](OCc1ccccc1)[C@H](C)Oc1ccc(F)cc1F]

A solution of (2S,3R)-3-(benzyloxy)-4-methylpentan-2-ol (91.5 mg, 0.439 mmol) was prepared in DMF (1.76 mL) at rt in a small vial. To this solution was added potassium tert-butoxide (71.5 mg, 0.637 mmol) followed by 1,2,4-trifluorobenzene (138 µL, 1.318 mmol). The mixture was stirred at 60° C. for 72 h. The reaction was quenched with AcOH (72 µL) and then diluted with hexanes (1.76 mL). The mixture was purified by flash column chromatography ($SiO_2$, 0→20% ethyl acetate in hexanes) to afford the title compound (122.6 mg, 87%) as a clear, colorless oil: $^1$H NMR (400 MHz, $CDCl_3$) δ 7.43-7.37 (m, 2H), 7.37-7.31 (m, 2H), 7.31-7.25 (m, 1H), 7.01 (ddd, J=10.7, 8.9, 5.4 Hz, 1H), 6.68 (ddd, J=9.8, 6.7, 3.0 Hz, 1H), 6.58 (ddt, J=8.9, 7.7, 3.1 Hz, 1H), 4.88 (d, J=11.1 Hz, 1H), 4.61 (d, J=11.1 Hz, 1H), 4.51 (qd, J=6.2, 3.8 Hz, 1H), 3.42 (dd, J=6.9, 3.8 Hz, 1H), 1.89 (h, J=6.8 Hz, 1H), 1.38 (d, J=6.3 Hz, 3H), 1.01 (d, J=6.7 Hz, 3H), 0.99 (d, J=6.8 Hz, 3H); $^{13}$C NMR (101 MHz, $CDCl_3$) δ 158.73 (dd, J=242.0, 2.5 Hz), 149.83 (dd, J=241.2, 3.2 Hz), 146.37 (dd, J=12.5, 10.4 Hz), 138.86, 128.29, 127.99, 127.52, 116.51 (dd, J=21.2, 10.3 Hz), 106.87 (dd, J=23.9, 7.0 Hz), 104.17 (dd, J=27.0, 2.1 Hz), 86.00, 77.45, 74.87, 30.42, 19.66, 18.78, 14.46; $^{19}$F NMR (376 MHz, $CDCl_3$) δ −116.80 (d, J=15.0 Hz), −138.81 (d, J=15.0 Hz); IR (thin film) 2963, 1624, 1510, 1205, 1150, 1099, 698 $cm^{-1}$; HRMS-ESI (m/z) calc'd for $[C_{19}H_{26}F_2NO_2]^+$, 338.1926; found, 338.192.

Example 6C: Preparation of 1-methoxy-4-((((2R, 3S)-3-((2-methylallyl)oxy)-1-phenylbutan-2-yl)oxy)methyl)benzene

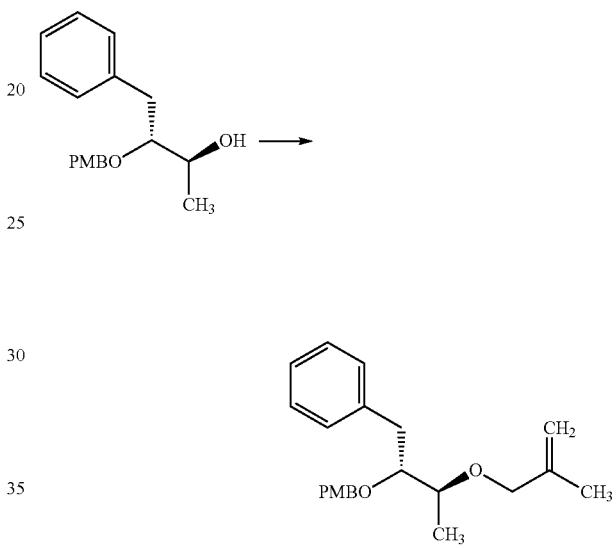

A solution of (2S,3R)-3-((4-methoxybenzyl)oxy)-4-phenylbutan-2-ol (0.145 g, 0.506 mmol) was prepared in THF (1.688 mL). Sodium hydride (0.030 g, 0.760 mmol) and TBAI (0.019 g, 0.051 mmol) were then added. 3-bromo-2-methylprop-1-ene (0.153 mL, 1.519 mmol) was added in one portion and the reaction was allowed to reflux. The reaction was then quenched with water and extracted with $Et_2O$ (2×), dried over $Na_2SO_4$, filtered, and concentrated to an oil. The crude material was purified by flash column chromatography ($SiO_2$, 0→10% ethyl acetate in hexanes) to afford the title compound (144.1 mg, 79%) as a clear, colorless oil: $^1$H NMR (400 MHz, $CDCl_3$) δ 7.33-7.18 (m, 5H), 7.12-7.01 (m, 2H), 6.83-6.77 (m, 2H), 5.01-4.92 (m, 1H), 4.89-4.80 (m, 1H), 4.47 (d, J=11.0 Hz, 1H), 4.26 (d, J=11.0 Hz, 1H), 3.94 (d, J=12.5 Hz, 1H), 3.89 3.80 (m, 1H), 3.78 (s, 3H), 3.63 (dt, J=8.5, 4.4 Hz, 1H), 3.46 (qd, J=6.3, 4.3 Hz, 1H), 2.89 (dd, J=13.9, 4.4 Hz, 1H), 2.79 (dd, J=13.9, 8.1 Hz, 1H), 1.74 (t, J=1.1 Hz, 3H), 1.24 (d, J=6.3 Hz, 3H); $^{13}$C NMR (126 MHz, $CDCl_3$) δ 159.00, 142.65, 139.42, 130.77, 129.57, 129.49, 128.19, 126.01, 113.59, 111.73, 82.70, 76.66, 72.84, 72.64, 55.26, 37.96, 19.68, 15.29; IR (thin film) 3027, 2932, 1612, 1512, 1495, 1453, 1301, 1246, 1172, 1081, 1035, 898, 820, 743, 699 $cm^{-1}$; HRMS-ESI (m/z) calc'd for $[C_{22}H_{29}O_3]^+$, 341.2111; found, 341.2095.

Example 7: Preparation of (2R,3S)-2-((4-methoxybenzyl)oxy)-3-phenoxybutan-1-ol

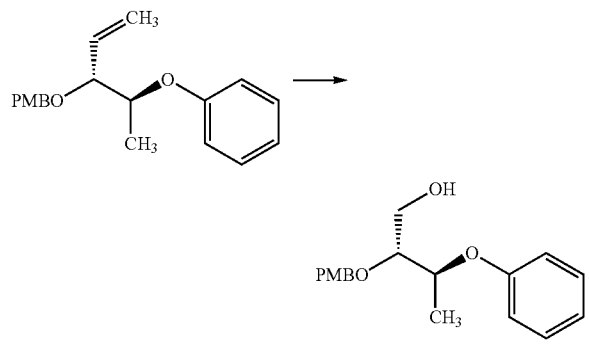

In a 100 mL flask, 1-methoxy-4-((((3R,4S)-4-phenoxypent-1-en-3-yl)oxy)methyl)benzene (0.908 g, 3.04 mmol) and sodium bicarbonate (0.026 g, 0.304 mmol) were dissolved in anhydrous DCM (29.5 mL) and anhydrous MeOH (0.928 mL). To this solution was added 5 drops of a 1% DCM solution of sudan III indicator, producing a light pink solution. The reaction was cooled to −78° C. in a dry ice/acetone bath. After ~5 min, $O_3$ was bubbled through the reaction until the pink color disappeared. The reaction was then purged with $N_2$ gas, and additional MeOH (9.28 mL) was added followed by solid sodium borohydride (0.345 g, 9.13 mmol) in one portion. The solution was allowed to warm to rt via removal of the dry ice/acetone bath, and the reaction was stirred overnight. After 18 h, TLC indicated conversion to a single lower $R_f$ spot. The reaction was quenched with $H_2O$ (50 mL) and extracted with DCM (3×50 mL). The combined organic layers were passed through a phase separator and concentrated to afford a colorless oil. The crude oil was purified by flash column chromatography ($SiO_2$, 0→100% ethyl acetate in hexanes) to afford the title compound (893.7 mg, 97%) as a clear, colorless oil: $^1$H NMR (300 MHz, $CDCl_3$) δ 7.32-7.22 (m, 5H), 6.99-6.84 (m, 5H), 4.70 (d, J=11.2 Hz, 1H), 4.60 (d, J=11.2 Hz, 1H), 4.56-4.46 (m, 1H), 3.80 (s, 3H), 3.76 (dt, J=6.0, 4.6 Hz, 2H), 3.65 (td, J=5.0, 4.4 Hz, 1H), 1.36 (d, J=6.3 Hz, 3H); $^{13}$C NMR (75 MHz, $CDCl_3$) δ 159.41, 157.49, 130.15, 129.67, 129.59, 121.14, 115.99, 113.93, 81.20, 73.81, 72.66, 61.49, 55.29, 16.09; IR (thin film) 3427, 2934, 1612, 1585, 1512, 1493, 1240, 1067, 1031, 752, 692 cm$^{-1}$; HRMS-ESI (m/z) calc'd for $[C_{18}H_{22}NaO_4]^+$, 325.1410; found, 325.1396.

Example 8A: Preparation of (((2R,3S)-2-((4-methoxybenzyl)oxy)butane-1,3-diyl)bis(oxy))dibenzene

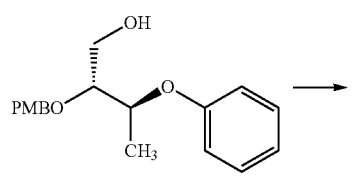

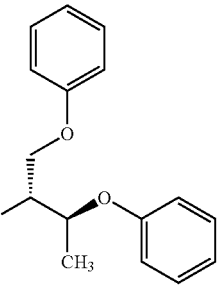

A solution of (2R,3S)-2-((4-methoxybenzyl)oxy)-3-phenoxybutan-1-ol (180 mg, 0.595 mmol), triphenylbismuth(V) acetate (499 mg, 0.893 mmol) and copper(II) acetate (16.22 mg, 0.089 mmol) was prepared in anhydrous toluene (3.97 mL) in a 20 mL vial under an atmosphere of $N_2$. N-cyclohexyl-N-methylcyclohexanamine (166 μL, 0.774 mmol) was then added via syringe in one portion. The resulting blue/green reaction was heated to 40° C. yielding a pale blue/green reaction mixture and stirred for 48 h. After 48 h, TLC indicated consumption of starting material and conversion to a single higher $R_f$ spot. The reaction was cooled to room temperature and filtered through a plug of Celite® with DCM, and the organics were concentrated to afford a dark yellow oil. The crude oil was purified by flash column chromatography ($SiO_2$, 0→20% ethyl acetate in hexanes) to afford the title compound (208.5 mg, 93%) as a clear, colorless oil: $^1$H NMR (400 MHz, $CDCl_3$) δ 7.33-7.20 (m, 6H), 6.98-6.82 (m, 8H), 4.71 (s, 2H), 4.68-4.60 (m, 1H), 4.17 (dd, J=10.0, 4.8 Hz, 1H), 4.10 (dd, J=10.0, 5.5 Hz, 1H), 3.98 (q, J=5.1 Hz, 1H), 3.78 (s, 3H), 1.40 (d, J=6.2 Hz, 3H); $^{13}$C NMR (101 MHz, $CDCl_3$) δ 159.31, 158.67, 157.61, 130.42, 129.66, 129.53, 129.45, 120.95, 120.92, 115.92, 114.62, 113.80, 78.80, 73.70, 73.03, 67.81, 55.26, 15.52; IR (thin film) 2933, 1598, 1492, 1237, 1081, 1032, 751, 691 cm$^{-1}$; HRMS-ESI (m/z) calcd for $[C_{24}H_{26}NaO_4]^+$, 401.1723; found, 401.1725.

Example 8B: Preparation of 1-methoxy-4-((((2R,3S)-1-methoxy-3-phenoxybutan-2-yl)oxy)methyl)benzene

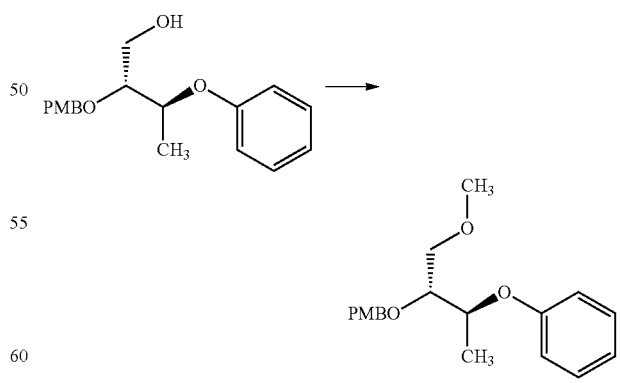

In a small vial, (2R,3S)-2-((4-methoxybenzyl)oxy)-3-phenoxybutan-1-ol (150 mg, 0.496 mmol) was dissolved in DCM (2.48 mL) under an atmosphere of $N_2$. $N_1,N_1,N_8,N_8$-tetramethylnaphthalene-1,8-diamine (319 mg, 1.488 mmol) was added in one portion, followed by trimethyloxonium tetrafluoroborate (110 mg, 0.744 mmol). The resulting clear, colorless solution was stirred at rt overnight. After 20 h, TLC indicated complete consumption of starting material. The reaction was carefully quenched with sat. aq. NaHCO$_3$ (20 mL) and extracted with DCM (3×20 mL). The combined organic layers were washed with 1N HCl (2×20 mL) followed by brine (20 mL). The organic layers were filtered through a phase separator and concentrated to afford a pale yellow oil. The crude oil was purified by flash column chromatography (SiO$_2$, 0→30% ethyl acetate in hexanes) to afford the title compound (117.5 mg, 75%) as a pale yellow oil: $^1$H NMR (400 MHz, CDCl$_3$) δ 7.31-7.22 (m, 4H), 6.97-6.81 (m, 5H), 4.65 (s, 2H), 4.54 (qd, J=6.2, 4.9 Hz, 1H), 3.79 (s, 3H), 3.74 (q, J=5.0 Hz, 1H), 3.56 (dd, J=10.3, 4.6 Hz, 1H), 3.51 (dd, J=10.2, 5.3 Hz, 1H), 3.33 (s, 3H), 1.34 (d, J=6.3 Hz, 3H); $^{13}$C NMR (101 MHz, CDCl$_3$) δ 159.20, 157.78, 130.71, 129.50, 129.48, 120.79, 115.91, 113.73, 79.30, 73.71, 72.64, 72.32, 59.22, 55.26, 15.44; IR (thin film) 2894, 1598, 1513, 1493, 1240, 1083, 1034, 752, 692 cm$^{-1}$; HRMS-ESI (m/z) calcd for [C$_{19}$H$_{24}$NaO$_4$]$^+$, 339.1567; found, 339.1569.

Example 8C: Preparation of 1-((((2R,3S)-1-(benzyloxy)-3-phenoxybutan-2-yl)oxy)methyl)-4-methoxybenzene

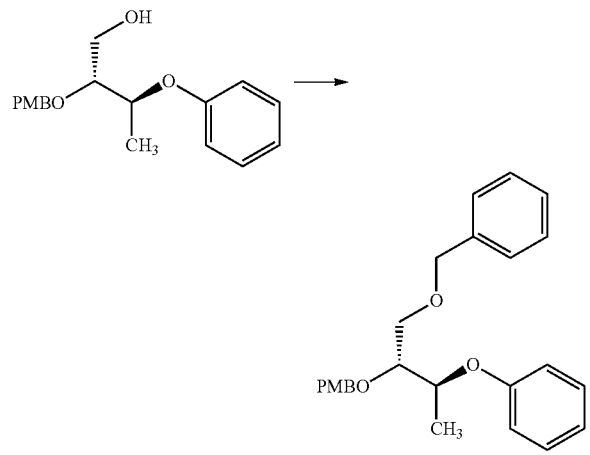

In a 20 mL vial, a solution of (2R,3S)-2-((4-methoxybenzyl)oxy)-3-phenoxybutan-1-ol (145 mg, 0.480 mmol) was prepared in DMF (3.84 mL) and cooled to 0° C. in an ice water bath. After ~5 min, sodium hydride (33.6 mg, 0.839 mmol) was added, and the resulting reaction mixture was stirred for 2 h, slowly warming to rt. After 2 h, the reaction was cooled to 0° C., and (bromomethyl)benzene (99 μL, 0.911 mmol) was added in one portion via syringe, followed by tetrabutylammonium iodide (17.71 mg, 0.048 mmol). The reaction was allowed to stir overnight, slowly warming to rt as the ice bath melted. After 18 h, TLC indicated complete consumption of starting material. The reaction was quenched with sat. aq. NH$_4$Cl (20 mL) and extracted with Et$_2$O (3×20 mL). The combined organic layers were washed with brine (20 mL), dried over MgSO$_4$, filtered, and concentrated to afford a yellow oil. The crude oil was purified by flash column chromatography (SiO$_2$, 0→20% ethyl acetate in hexanes) to afford the title compound (148.4 mg, 79%) as a clear, colorless oil: $^1$H NMR (400 MHz, CDCl$_3$) δ 7.34-7.20 (m, 9H), 6.96-6.87 (m, 3H), 6.87-6.82 (m, 2H), 4.65 (s, 2H), 4.63-4.55 (m, 1H), 4.51 (d, J=2.0 Hz, 2H), 3.82-3.74 (m, 4H), 3.68-3.57 (m, 2H), 1.34 (d, J=6.3 Hz, 3H); $^{13}$C NMR (101 MHz, CDCl$_3$) δ 159.19, 157.76, 138.25, 130.69, 129.51, 129.48, 128.32, 127.58, 127.54, 120.75, 115.86, 113.72, 79.41, 73.65, 73.37, 72.67, 69.77, 55.25, 15.40; IR (thin film) 3029, 2862, 1597, 1512, 1493, 1240, 1086, 1033, 751, 693 cm$^{-1}$; HRMS-ESI (m/z) calc'd for [C$_{25}$H$_{28}$NaO$_4$]$^+$, 415.1880; found, 415.1876.

Example 8D: Preparation of 1-((((2R,3S)-1-(allyloxy)-3-phenoxybutan-2-yl)oxy)methyl)-4-methoxybenzene

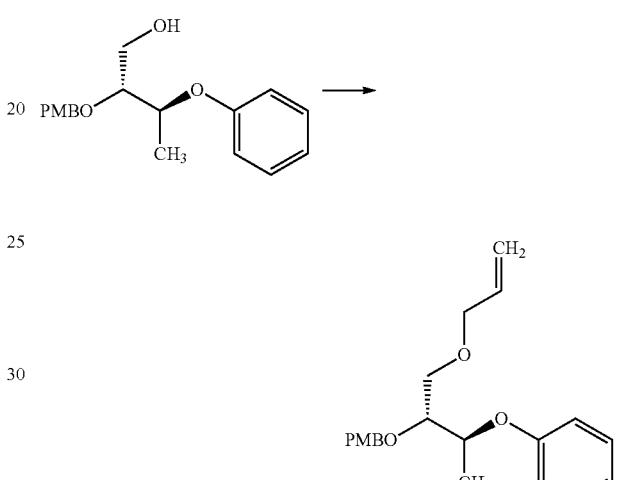

In a 20 mL vial, a solution of (2R,3S)-2-((4-methoxybenzyl)oxy)-3-phenoxybutan-1-ol (145.4 mg, 0.481 mmol) was prepared in DMF (3.85 mL) and cooled to 0° C. in an ice water bath. After ~5 min, sodium hydride (33.7 mg, 0.842 mmol) was added, and the resulting reaction mixture was stirred for 2 h while slowly warming to rt. After 2 h, the reaction was cooled to 0° C., and allyl bromide (79 μL, 0.914 mmol) was added in one portion via syringe, followed by tetrabutylammonium iodide (17.76 mg, 0.048 mmol). The reaction was allowed to stir overnight, slowly warming to rt as the ice bath melted. After 20 h, TLC indicated consumption of starting material. The reaction was quenched with sat. aq. NH$_4$Cl (20 mL) and extracted with Et$_2$O (3×20 mL). The combined organic layers were washed with brine (20 mL), dried over MgSO$_4$, filtered, and concentrated to afford a yellow oil. The crude oil was purified by flash column chromatography (SiO$_2$, 0→20% ethyl acetate in hexanes) to afford the title compound (145.4 mg, 88%) as a clear, colorless oil: $^1$H NMR (400 MHz, CDCl$_3$) δ 7.31-7.20 (m, 4H), 6.96-6.82 (m, 5H), 5.87 (ddt, J=17.1, 10.8, 5.5 Hz, 1H), 5.25 (dq, J=17.2, 1.7 Hz, 1H), 5.16 (dq, J=10.4, 1.4 Hz, 1H), 4.66 (s, 2H), 4.56 (qd, J=6.2, 4.8 Hz, 1H), 3.97 (dt, J=5.5, 1.5 Hz, 2H), 3.85-3.73 (m, 4H), 3.62 (dd, J=10.2, 4.8 Hz, 1H), 3.56 (dd, J=10.2, 5.5 Hz, 1H), 1.35 (d, J=6.3 Hz, 3H); $^{13}$C NMR (101 MHz, CDCl$_3$) δ 159.20, 157.78, 134.75, 130.74, 129.52, 129.47, 120.76, 116.81, 115.91, 113.73, 79.35, 73.77, 72.72, 72.30, 69.84, 55.26, 15.37; IR (thin film) 2865, 1598, 1513, 1493, 1240, 1084, 1034, 752 cm$^{-1}$; HRMS-ESI (m/z) calcd for [C$_{21}$H$_{26}$NaO$_4$]$^+$, 365.1723; found, 365.1731.

Example 9, Step 1: Preparation of (2S,3S)-2-((4-methoxybenzyl)oxy)-3-phenoxybutanal

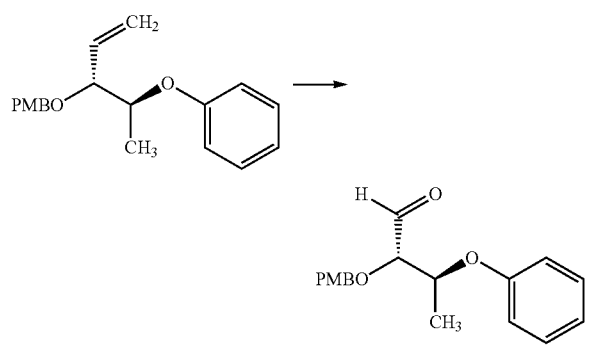

In a 100 mL flask, 1-methoxy-4-((((3R,4S)-4-phenoxypent-1-en-3-yl)oxy)methyl)benzene (0.500 g, 1.676 mmol) and sodium bicarbonate (0.014 g, 0.168 mmol) were dissolved in anhydrous DCM (15.23 mL) and anhydrous MeOH (1.523 mL). To this solution was added 5 drops of a 1% DCM solution of sudan III indicator, producing a light pink solution. The reaction was cooled to −78° C. in a dry ice/acetone bath. After ~5 min, O₃ was bubbled through the reaction until the pink color disappeared. The reaction was then purged with nitrogen gas for ~5 min, and then dimethylsulfide (1.231 mL, 16.76 mmol) was added in one portion via syringe. The resulting solution was allowed to warm to rt via removal of the dry ice/acetone bath, and the reaction was stirred overnight. After 18 h, TLC indicated consumption of starting material and conversion to a major lower $R_f$ product. The reaction was quenched with H₂O (50 mL) and extracted with DCM (3×50 mL). The combined organic layers were passed through a phase separator and concentrated to afford a colorless oil. The crude oil was purified by flash column chromatography (SiO₂, 0→30% ethyl acetate in hexanes) to afford the title compound (385.2 mg, 77%) as a clear, colorless oil: ¹H NMR (400 MHz, CDCl₃) δ 9.69 (d, J=1.6 Hz, 1H), 7.34-7.21 (m, 4H), 7.00-6.81 (m, 5H), 4.81-4.55 (m, 3H), 4.00 (dd, J=3.9, 1.7 Hz, 1H), 3.80 (s, 3H), 1.36 (d, J=6.3 Hz, 3H); ¹³C NMR (101 MHz, CDCl₃) δ 202.57, 159.62, 157.03, 129.86, 129.63, 129.20, 121.50, 116.02, 113.97, 84.11, 74.29, 73.09, 55.29, 15.70; IR (thin film) 2934, 2836, 1731, 1513, 1491, 1232, 1087, 1031, 752 cm⁻¹; HRMS-ESI (m/z) calc'd for [C₁₈H₂₄NO₄]⁺, 318.1700; found, 318.1703.

Example 9, Step 2: Preparation of 1-((((2S,3S)-1,1-difluoro-3-phenoxybutan-2-yl)oxy)methyl)-4-methoxybenzene

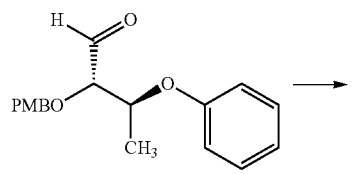

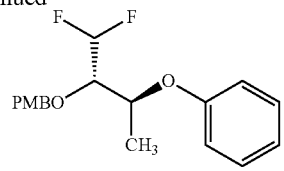

A solution of (2S,3S)-2-((4-methoxybenzyl)oxy)-3-phenoxybutanal (0.361 g, 1.202 mmol) was prepared in DCM (12.02 mL) and cooled to 0° C. in an ice/water bath. After ~5 min, Deoxofluor (~50% in toluene, 2.66 g, 6.01 mmol) was added in one portion followed by 1 drop of MeOH. The solution was stirred overnight, slowly warming to rt as the ice melted. After 18 h, TLC indicated consumption of starting material, and the mixture was concentrated to afford an orange oil. The crude oil was purified by flash column chromatography (SiO₂, 0→100% ethyl acetate in hexanes) to afford the title compound (342.1 mg, 88%) as a clear, colorless oil: ¹H NMR (400 MHz, CDCl₃) δ 7.32-7.23 (m, 4H), 7.01-6.94 (m, 1H), 6.92-6.83 (m, 4H), 5.91 (td, J=55.0, 3.4 Hz, 1H), 4.77 (d, J=11.1 Hz, 1H), 4.69 (d, J=11.1 Hz, 1H), 4.56 (p, J=6.2 Hz, 1H), 3.85-3.74 (m, 4H), 1.37 (d, J=6.3 Hz, 3H); ¹⁹F NMR (376 MHz, CDCl₃) δ −127.71 (dd, J=290.8, 2.1 Hz), −130.30 (dd, J=290.8, 4.0 Hz); IR (thin film) 2937, 1598, 1514, 1494, 1241, 1074, 1035, 754 cm⁻¹.

Example 10A: Preparation of (2R,3S)-1-phenyl-3-propoxybutan-2-ol

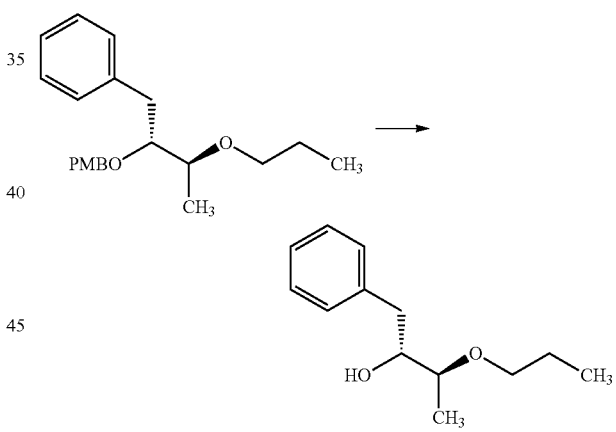

To a magnetically stirred mixture of 1-methoxy-4-((((2R,3S)-1-phenyl-3-propoxybutan-2-yl)oxy)methyl)benzene (90 mg, 0.274 mmol) in DCM (2466 μL) and water (274 μL) was added DDQ (65.3 mg, 0.288 mmol), and the reaction was stirred at 0° C. in an ice bath. The reaction was allowed to gradually warm to rt and was stirred overnight. The reaction was quenched with NaOH (1N) extracted with DCM (3×). The combined organic layers were passed through a phase separator and then concentrated. The crude material was purified by flash column chromatography (SiO₂, 0→10% ethyl acetate in hexanes). The product coeluted with undesired p-anisaldehyde byproduct. The material was diluted with DCM (2 mL), and PS-TsNHNH₂ (300 mg, solid support) was added and the mixture was stirred at rt for 1 h. The reaction was filtered, and the filtrate was concentrated to provide the title compound (51.2 mg, 85%) as a yellow oil: ¹H NMR (400 MHz, CDCl₃) δ 7.36-7.28 (m, 2H), 7.27-7.19 (m, 3H), 3.92 (dq, J=8.3, 4.0 Hz, 1H), 3.48 (dt, J=9.1, 6.6 Hz, 1H), 3.42-3.32 (m, 2H), 2.80 (dd, J=13.9, 4.6 Hz, 1H), 2.72 (dd, J=13.9, 8.7 Hz, 1H), 2.01 (d, J=3.5 Hz, 1H), 1.64-1.52 (m, 3H), 1.20 (d, J=6.3 Hz, 3H), 0.92 (t, J=7.4 Hz, 3H); $^{13}$C NMR (126 MHz, CDCl$_3$) δ 138.74, 129.24, 128.49, 126.32, 77.44, 74.26, 70.62, 38.86, 23.30, 13.98, 10.67; IR (thin film) 3441, 2962, 2933, 2875, 1604, 1495, 1453, 1381, 1330, 1253, 1133, 1091, 1031, 984, 745, 699 cm$^{-1}$.

Example 10B: Preparation of (1R,2S)-2-phenoxy-1-phenylpropan-1-ol

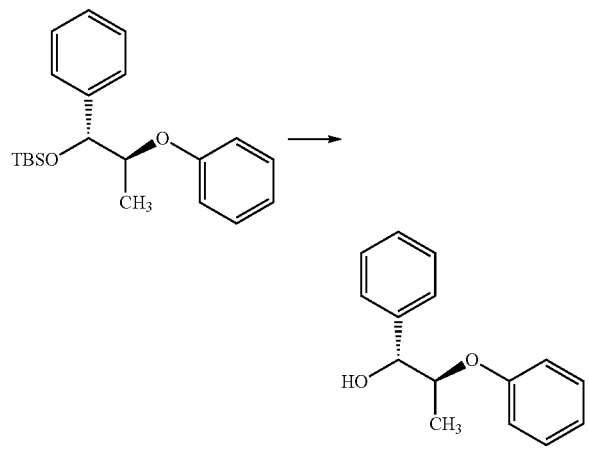

A solution of tert-butyldimethyl((1R,2S)-2-phenoxy-1-phenylpropoxy)silane (359.8 mg, 1.050 mmol) was prepared in a 20 mL vial in THF (5.25 mL) under N$_2$ and was cooled to 0° C. After 5 min, TBAF (1.05 mL, 1.050 mmol) was added dropwise via syringe over 2 min. The reaction mixture was allowed to warm to rt and was stirred for 4 h. The reaction was quenched with saturated aqueous NH$_4$Cl (25 mL) and extracted with Et$_2$O (3×25 mL). The combined organic layers were dried over MgSO$_4$, filtered, and concentrated to afford a clear colorless oil. The oil was purified by flash column chromatography (SiO$_2$, 0→30% ethyl acetate in hexanes) to afford the title compound (96.0 mg, 40%) as a clear, colorless oil: $^1$H NMR (400 MHz, CDCl$_3$) δ 7.40 (d, J=7.2 Hz, 2H), 7.34 (t, J=7.5 Hz, 2H), 7.27 (td, J=7.1, 2.0 Hz, 3H), 7.00-6.88 (m, 3H), 5.02 (t, J=3.3 Hz, 1H), 4.55 (qd, J=6.3, 3.5 Hz, 1H), 2.63 (d, J=3.0 Hz, 1H), 1.17 (d, J=6.3 Hz, 3H); $^{13}$C NMR (101 MHz, CDCl$_3$) δ 157.44, 140.15, 129.65, 128.34, 127.64, 126.39, 121.37, 116.31, 77.93, 75.12, 13.01; IR (thin film) 3443, 2985, 1598, 1493, 1239, 1063, 752, 701 cm$^{-1}$.

Example 10C: Preparation of 1-(((2S,3R)-3-(benzyloxy)-4-methylpentan-2-yl)oxy)-3-chloro-5-fluorobenzene

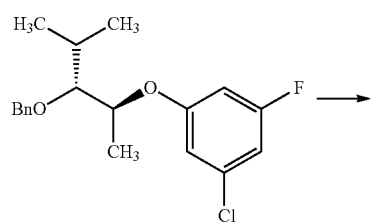

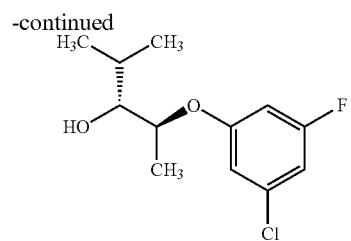

In a small vial, 1-(((2S,3R)-3-(benzyloxy)-4-methylpentan-2-yl)oxy)-3-chloro-5-fluorobenzene (160.0 mg, 0.475 mmol) was dissolved in ethanol (1.58 mL) and cyclohexene (0.79 mL). To this solution was added palladium on carbon (5 wt %, 50.6 mg, 0.024 mmol) in one portion, and the resulting reaction mixture was heated to 70° C. and stirred overnight. The reaction was cooled to rt, filtered through a plug of Celite® eluting with ethyl acetate, and concentrated to an oil. The oil was purified by flash column chromatography (SiO$_2$, 0→50% acetone in hexanes) to afford the title compound (114.0 mg, 97%) as a yellow oil: $^1$H NMR (400 MHz, CDCl$_3$) δ 6.69 (dp, J=4.2, 2.0 Hz, 2H), 6.51 (dt, J=10.5, 2.3 Hz, 1H), 4.40 (qd, J=6.2, 4.0 Hz, 1H), 3.52 (dd, J=7.5, 4.0 Hz, 1H), 2.02 (s, 1H), 1.80 (dq, J=13.7, 6.9 Hz, 1H), 1.30 (d, J=6.2 Hz, 3H), 1.01 (d, J=6.6 Hz, 3H), 0.96 (d, J=6.9 Hz, 3H); $^{13}$C NMR (101 MHz, CDCl$_3$) δ 163.45 (d, J=248.0 Hz), 159.06 (d, J=12.1 Hz), 135.54 (d, J=13.5 Hz), 112.29 (d, J=3.3 Hz), 108.95 (d, J=25.2 Hz), 102.10 (d, J=24.8 Hz), 77.96, 75.72, 29.85, 18.95, 18.38, 13.13; $^{19}$F NMR (376 MHz, CDCl$_3$) δ -109.95; IR (thin film) 3464, 2963, 1606, 1452, 1140, 1044, 917, 833 cm$^{-1}$.

Example 11: Preparation of (2S,3R)-2-(3-chloro-5-fluorophenoxy)-4-methylpentan-3-yl (tert-butoxycarbonyl)-L-alaninate

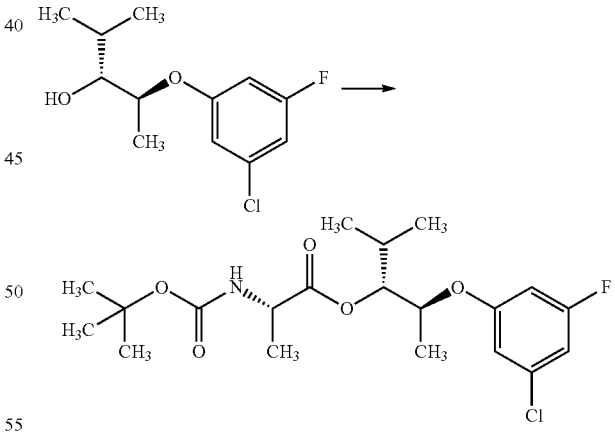

In a small vial, (2S,3R)-2-(3-chloro-5-fluorophenoxy)-4-methylpentan-3-ol (114 mg, 0.462 mmol), (tert-butoxycarbonyl)-L-alanine (109 mg, 0.578 mmol) and DMAP (5.65 mg, 0.046 mmol) were dissolved in DCM (2.31 mL) under N$_2$ and cooled to 0° C. in an ice/water bath. After ~5 min, EDCI (143 mg, 0.924 mmol) was added in one portion, and the resulting pale yellow reaction was stirred overnight, slowly warming to rt as the ice melted. The reaction was concentrated to afford an oil. The oil was purified by flash column chromatography (SiO$_2$, 0→30% ethyl acetate in hexanes) to afford the title compound (171.0 mg, 89%) as a clear, colorless oil: $^1$H NMR (400 MHz, CDCl$_3$) δ 6.72-6.63 (m, 2H), 6.49 (dt, J=10.5, 2.3 Hz, 1H), 5.04 (d, J=8.1 Hz, 1H), 5.00 (t, J=5.8 Hz, 1H), 4.45 (p, J=6.1 Hz, 1H), 4.35 (p, J=7.5 Hz, 1H), 2.05 (dq, J=13.5, 6.7 Hz, 1H), 1.46 (s, 9H), 1.43 (d, J=7.2 Hz, 3H), 1.30 (d, J=6.2 Hz, 3H), 0.97 (d, J=6.9 Hz, 3H), 0.91 (d, J=6.7 Hz, 3H); $^{13}$C NMR (101 MHz, CDCl$_3$) δ 172.97, 163.41 (d, J=248.0 Hz), 159.01 (d, J=12.3 Hz), 155.12, 135.49 (d, J=13.4 Hz), 112.14 (d, J=3.2 Hz), 109.04 (d, J=25.3 Hz), 102.09 (d, J=24.8 Hz), 79.89, 79.28, 73.49, 49.56, 28.78, 28.35, 19.22, 18.65, 17.34, 15.01; $^{19}$F NMR (376 MHz, CDCl$_3$) δ −110.00; IR (thin film) 3373, 2974, 1713, 1605, 1140, 1063 cm$^{-1}$; HRMS-ESI (m/z) calc'd for [C$_{20}$H$_{29}$ClFNNaO$_5$]$^+$, 440.1611; found, 440.1611.

Example 12A: Preparation of (3R,4S)-2-methyl-4-propoxypentan-3-yl (tert-butoxycarbonyl)-L-alaninate

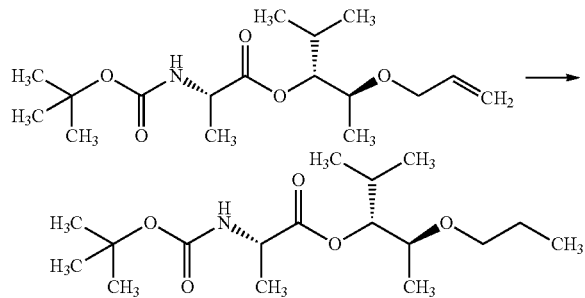

In a vial containing (2S,3R)-2-(allyloxy)-4-methylpentan-3-yl (tert-butoxycarbonyl)-L-alaninate (0.1 g, 0.304 mmol) and 5% palladium on carbon (0.097 g, 0.046 mmol) was added EtOAc (1.52 mL) under a N$_2$. The atmosphere was then replaced with hydrogen via balloon, and the reaction was left to stir overnight. After 20 h, the reaction was then filtered through Celite® and was washed with EtOAc. The filtrate was then concentrated and the crude was analyzed via NMR to confirm complete conversion. The crude material was purified by flash column chromatography (SiO$_2$, 0→20% ethyl acetate in hexanes) to afford the title compound (92.2 mg, 87%) as a clear, colorless oil: $^1$H NMR (400 MHz, CDCl$_3$) δ 5.09 (d, J=7.8 Hz, 1H), 4.85 (t, J=5.9 Hz, 1H), 4.39-4.22 (m, 1H), 3.49 (p, J=6.2 Hz, 1H), 3.46-3.27 (m, 2H), 2.03 (h, J=6.7 Hz, 1H), 1.59-1.48 (m, 2H), 1.44 (s, 9H), 1.41 (d, J=7.2 Hz, 3H), 1.11 (d, J=6.2 Hz, 3H), 0.94-0.86 (m, 9H); $^{13}$C NMR (126 MHz, CDCl$_3$) δ 172.97, 155.07, 79.86, 79.65, 74.27, 70.63, 49.53, 28.57, 28.33, 23.22, 19.34, 18.98, 17.32, 15.34, 10.66; IR (thin film) 3359, 2967, 2936, 2877, 1716, 1502, 1455, 1366, 1340, 1248, 1167, 1107, 1066, 1021 cm$^{-1}$; HRMS-ESI (m/z) calc'd for [C$_{17}$H$_{33}$NO$_5$Na]$^+$, 354.2251; found, 354.2251.

Example 12B: Preparation of (2S,3R)-2-phenoxyhexan-3-yl (tert-butoxycarbonyl)-L-alaninate

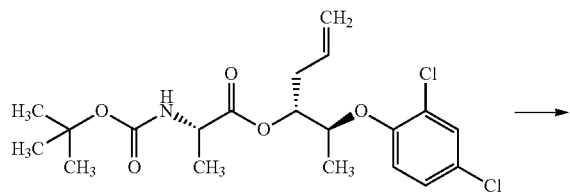

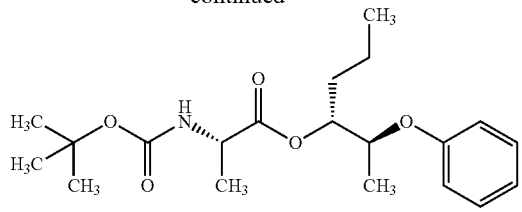

To a 20 mL vial containing (S)-(2S,3R)-2-(2,4-dichlorophenoxy)hex-5-en-3-yl 2-((tert-butoxycarbonyl)amino)propanoate (166.7 mg, 0.386 mmol) and palladium (5% wt on carbon, dry basis, 82 mg, 0.039 mmol) was added ethyl acetate (3.86 mL). The black reaction mixture was flushed with H$_2$ gas via balloon. The resulting reaction was stirred at room temperature overnight. After 18 h, TLC and UPLC indicated consumption of starting material. The reaction was filtered through a plug of celite, eluting with EtOAc (2×10 mL). The resulting solution was concentrated to afford a yellow oil. The crude material was purified by flash column chromatography (SiO$_2$, 0→40% ethyl acetate in hexanes) to afford the title compound (108.7 mg, 77%) as a clear, colorless oil: $^1$H NMR (400 MHz, CDCl$_3$) δ 7.33-7.19 (m, 2H), 7.00-6.91 (m, 1H), 6.91-6.81 (m, 2H), 5.09 (dt, J=8.7, 4.2 Hz, 1H), 5.05-4.91 (m, 1H), 4.45 (qd, J=6.3, 4.3 Hz, 1H), 4.29 (t, J=7.6 Hz, 1H), 1.79-1.57 (m, 2H), 1.53-1.16 (m, 2H), 1.45 (s, 9H), 1.36 (d, J=7.2 Hz, 3H), 1.30 (d, J=6.3 Hz, 3H), 0.92 (t, J=7.4 Hz, 3H); $^{13}$C NMR (101 MHz, CDCl$_3$) δ 172.96, 157.80, 155.05, 129.51, 121.19, 116.26, 115.59, 79.71, 76.45, 74.82, 49.49, 31.85, 28.32, 18.66, 15.64, 13.91; IR (thin film) 3368, 2963, 1712, 1493, 1239, 1163, 1057, 752 cm$^{-1}$; HRMS-ESI (m/z) calc'd for [C$_{20}$H$_{31}$NNaO$_5$]$^+$, 388.2097; found, 388.2077.

Example 13A, Step 1: Preparation of (2S,3R)-2-(3-chloro-5-fluorophenoxy)-4-methylpentan-3-yl L-alaninate hydrochloride

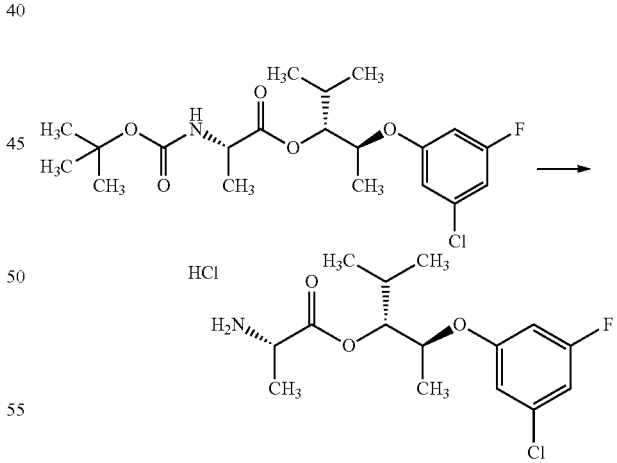

In a small vial, (2S,3R)-2-(3-chloro-5-fluorophenoxy)-4-methylpentan-3-yl (tert-butoxycarbonyl)-L-alaninate (171.0 mg, 0.409 mmol) was dissolved in DCM (2 mL). Hydrogen chloride (4M in dioxane, 1.534 mL, 6.14 mmol) was added in one portion via syringe. The resulting clear, colorless reaction was stirred at room temperature for 3 h. After 3 h, TLC indicated complete consumption of starting material and conversion to a baseline product. The reaction was concentrated under a stream of N$_2$ and dried in a vacuum oven to provide the title compound (145 mg, quant. yield) as a clear, colorless oil that was used directly in the next step: ESIMS m/z 318.2 [(M+H)+].

Example 13A, Step 2: Preparation of (2S,3R)-2-(3-chloro-5-fluorophenoxy)-4-methylpentan-3-yl (3-hydroxy-4-methoxypicolinoyl)-L-alaninate

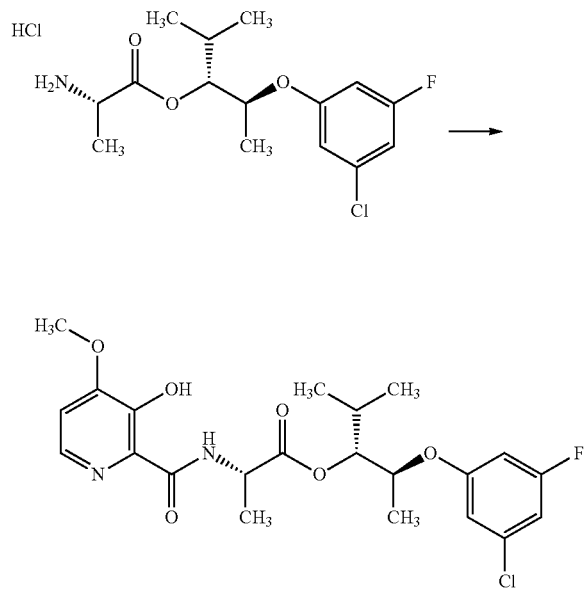

To a vial containing (2S,3R)-2-(3-chloro-5-fluorophenoxy)-4-methylpentan-3-ylL-alaninate hydrochloride (145 mg, 0.409 mmol) was added 3-hydroxy-4-methoxypicolinic acid (90 mg, 0.532 mmol) and ((1H-benzo[d][1,2,3]triazol-1-yl)oxy)tri(pyrrolidin-1-yl)phosphonium hexafluorophosphate(V) (277 mg, 0.532 mmol). DCM (8.18 mL) was added followed by N-ethyl-N-isopropylpropan-2-amine (428 μL, 2.454 mmol) dropwise over 45 seconds. After 10 min, most of the solids solubilized and the resultant pale pink colored reaction was stirred at rt overnight. The reaction was then concentrated under reduced pressure to yield an orange oil. The oil was purified by flash column chromatography (SiO$_2$, 0→50% acetone in hexanes) to afford the title compound (174.9 mg, 91% over two steps) as a clear, colorless oil: $^1$H NMR (400 MHz, CDCl$_3$) δ 12.11 (s, 1H), 8.49 (d, J=7.9 Hz, 1H), 7.99 (d, J=5.2 Hz, 1H), 6.88 (d, J=5.2 Hz, 1H), 6.74-6.59 (m, 2H), 6.48 (dt, J=10.5, 2.3 Hz, 1H), 5.04 (t, J=5.8 Hz, 1H), 4.77 (p, J=7.3 Hz, 1H), 4.47 (p, J=6.1 Hz, 1H), 3.95 (s, 3H), 2.07 (dq, J=13.4, 6.7 Hz, 1H), 1.61 (d, J=7.2 Hz, 3H), 1.30 (d, J=6.2 Hz, 3H), 0.98 (d, J=6.9 Hz, 3H), 0.92 (d, J=6.7 Hz, 3H); $^{13}$C NMR (101 MHz, CDCl$_3$) δ 171.71, 168.87, 163.40 (d, J=248.1 Hz), 158.95 (d, J=12.2 Hz), 155.44, 148.84, 140.54, 135.51 (d, J=13.5 Hz), 130.46, 112.15 (d, J=3.2 Hz), 109.55, 109.10 (d, J=25.2 Hz), 102.06 (d, J=24.7 Hz), 79.77, 73.50, 56.09, 48.11, 28.76, 19.26, 18.31, 17.30, 15.05; $^{19}$F NMR (376 MHz, CDCl$_3$) δ −109.89; IR (thin film) 3370, 2968, 1743, 1605, 1527, 1438, 1139, 730 cm$^{-1}$; HRMS-ESI (m/z) calc'd for [C$_{22}$H$_{27}$ClFN$_2$O$_6$]$^+$, 469.1536; found, 469.1531.

Example 13B, Step 1: Preparation of (3R,4S)-2-methyl-4-((2-methylallyl)oxy)pentan-3-yl L-alaninate

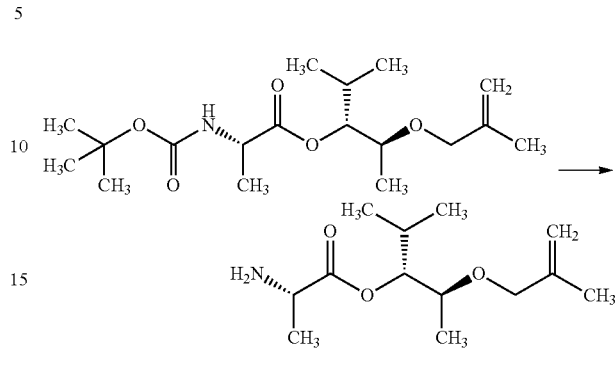

(3R,4S)-2-methyl-4-((2-methylallyl)oxy)pentan-3-yl (tert-butoxycarbonyl)-L-alaninate (0.155 g, 0.451 mmol) was dissolved in DCM (2.26 mL) and cooled to 0° C. in an ice bath. After ~5 min, TFA (0.522 mL, 6.77 mmol) was added dropwise via syringe over 30 seconds. The reaction was brought to rt via removal of the ice water bath and allowed to stir at rt for 2 h. After 2 h, TLC indicated consumption of starting material. The reaction was diluted with DCM and washed with saturated aqueous NaHCO$_3$. The aqueous layer was extracted with DCM (3×). The combined organic layers were passed through a phase separator and concentrated to afford the crude title compound as a thick oil that was used directly in the next step without further purification: IR (thin film) 3361, 2969, 1735, 1677, 1456, 1374, 1179, 1126, 1101, 907, 721 cm$^{-1}$; HRMS-ESI (m/z) calc'd for [C$_{13}$H$_{26}$NO$_3$]$^+$, 244.1907; found, 244.1910.

Example 13B, Step 2: Preparation of (3R,4S)-2-methyl-4-((2-methylallyl)oxy)pentan-3-yl (3-hydroxy-4-methoxypicolinoyl)-L-alaninate

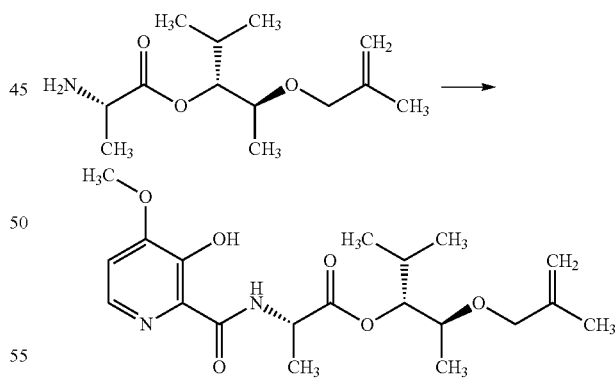

Crude (3R,4S)-2-methyl-4-((2-methylallyl)oxy)pentan-3-yl L-alaninate was dissolved in anhydrous DCM (4.4 mL). 3-hydroxy-4-methoxypicolinic acid (0.084 g, 0.496 mmol), PyBOP (0.258 g, 0.496 mmol), and ethyl-N-isopropylpropan-2-amine (0.260 mL, 1.489 mmol) were added. The reaction was then stirred at rt for 2 h. After 2 h, the material was concentrated to an oil. The oil was purified by flash column chromatography (SiO$_2$, 0→30% acetone in hexanes) to afford the title compound (74.4 mg, 42% over 2 steps) as a thick colorless oil: $^1$H NMR (500 MHz, CDCl$_3$) δ 12.18 (s, 1H), 8.54 (d, J=7.8 Hz, 1H), 7.99 (d, J=5.2 Hz, 1H), 6.87 (d, J=5.2 Hz, 1H), 4.96-4.91 (m, 2H), 4.88-0.83 (m, 1H), 4.80-4.71 (m, 1H), 3.95 (s, 3H), 3.92 (d, J=12.4 Hz, 1H), 3.85 (d, J=12.3 Hz, 1H), 3.62-3.56 (m, 1H), 2.04 (dq, J=13.4, 6.8 Hz, 1H), 1.72 (t, J=1.1 Hz, 3H), 1.60-1.57 (m, 3H), 1.14 (d, J=6.3 Hz, 3H), 0.92 (d, J=3.5 Hz, 3H), 0.91 (d, J=3.7 Hz, 3H); $^{13}$C NMR (126 MHz, CDCl$_3$) δ 171.83, 168.69, 155.34, 148.73, 142.32, 140.46, 130.54, 112.11, 109.40, 80.21, 73.54, 72.68, 56.07, 48.13, 28.62, 19.59, 19.34, 18.53, 17.56, 15.09; IR (thin film) 3370, 2968, 2939, 1739, 1649, 1576, 1527, 1481, 1438, 1366, 1330, 1280, 1263, 1212, 1182, 1150, 1101, 1060, 943, 849, 800 cm$^{-1}$; ESIMS m/z 395.3 [(M+H)$^+$].

Example 14A: Preparation of (3R,4S)-2-methyl-4-phenoxypentan-3-yl (3-acetoxy-4-methoxypicolinoyl)-L-alaninate

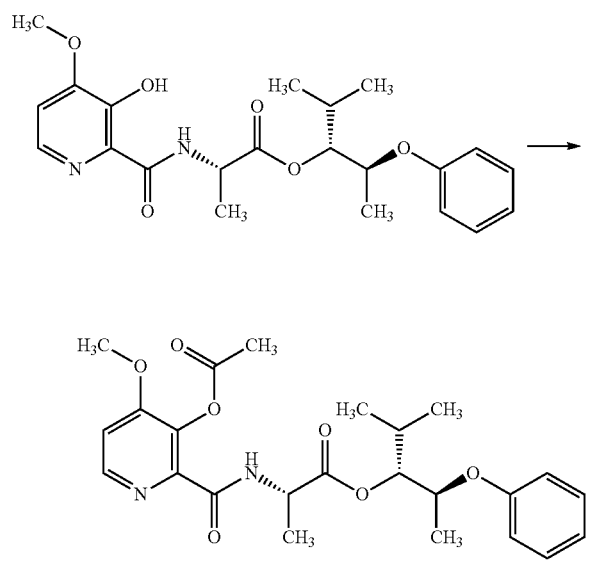

To a small vial containing (3R,4S)-2-methyl-4-phenoxypentan-3-yl (3-hydroxy-4-methoxypicolinoyl)-L-alaninate (83.8 mg, 0.201 mmol) was added pyridine (0.976 mL, 12.1 mmol) followed by acetic anhydride (0.951 mL, 10.1 mmol) via syringe. The resultant clear and colorless reaction mixture was stirred at rt for 1 h. The reaction was concentrated, diluted with 5 mL toluene, and reconcentrated to afford an oil. The oil was purified by flash column chromatography (SiO$_2$, 0→50% acetone in hexanes) to afford the title compound (78.1 mg, 85%) as a clear, colorless oil: $^1$H NMR (400 MHz, CDCl$_3$) δ 8.57 (d, J=6.9 Hz, 1H), 8.32 (d, J=5.4 Hz, 1H), 7.30-7.21 (m, 2H), 7.00 (d, J=5.5 Hz, 1H), 6.93 (tt, J=7.3, 1.0 Hz, 1H), 6.90-6.80 (m, 2H), 5.06 (dd, J=6.3, 5.3 Hz, 1H), 4.76 (p, J=7.3 Hz, 1H), 4.50 (p, J=6.2 Hz, 1H), 3.90 (s, 3H), 2.40 (s, 3H), 2.16-2.09 (m, 1H), 1.56 (d, J=7.1 Hz, 3H), 1.28 (d, J=6.2 Hz, 3H), 0.96 (d, J=6.9 Hz, 3H), 0.91 (d, J=6.8 Hz, 3H); $^{13}$C NMR (101 MHz, CDCl$_3$) δ 172.24, 168.88, 162.49, 159.50, 157.43, 146.68, 141.58, 137.55, 129.53, 121.09, 115.92, 109.79, 80.11, 72.60, 56.29, 48.28, 28.71, 20.73, 19.37, 18.72, 17.01, 15.52; IR (thin film) 3383, 2967, 1771, 1677, 1507, 1198, 1174 cm$^{-1}$; HRMS-ESI (m/z) calc'd for [C$_{24}$H$_{31}$N$_2$O$_7$]$^+$, 459.2126; found, 459.2096.

Example 14B: Preparation of (3R,4S)-2-methyl-4-phenoxypentan-3-yl (3-(acetoxymethoxy)-4-methoxypicolinoyl)-L-alaninate

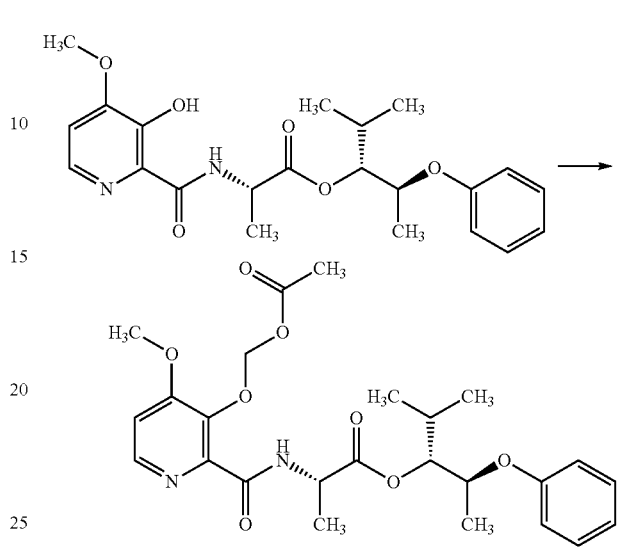

In a small vial, (S)-(3R,4S)-2-methyl-4-phenoxypentan-3-yl 2-(3-hydroxy-4-methoxypicolinamido)propanoate (81.9 mg, 0.197 mmol) was dissolved in acetone (1.5 mL). To this solution was added potassium carbonate (54.4 mg, 0.393 mmol) in one portion, followed by bromomethyl acetate (0.039 mL, 0.393 mmol) in one portion via syringe. The resulting cloudy white solution was stirred at 50° C. for 2 h. After 2 h, TLC indicated complete consumption of starting material. The reaction was then concentrated to a white oil under a stream of N$_2$. The oil was purified by flash column chromatography (SiO$_2$, 0→50% acetone in hexanes) to afford the title compound (77.4 mg, 81%) as a clear, colorless oil: $^1$H NMR (400 MHz, CDCl$_3$) δ 8.40 (d, J=7.7 Hz, 1H), 8.28 (d, J=5.3 Hz, 1H), 7.31-7.20 (m, 2H), 6.99-6.84 (m, 4H), 5.80-5.71 (m, 2H), 5.07 (dd, J=6.4, 5.1 Hz, 1H), 4.80 (p, J=7.2 Hz, 1H), 4.50 (p, J=6.2 Hz, 1H), 3.91 (s, 3H), 2.21-2.09 (m, 1H), 2.07 (s, 3H), 1.58 (d, J=7.1 Hz, 3H), 1.30 (d, J=6.2 Hz, 3H), 0.97 (d, J=6.9 Hz, 3H), 0.92 (d, J=6.8 Hz, 3H); $^{13}$C NMR (101 MHz, CDCl$_3$) δ 172.39, 170.27, 163.07, 160.32, 157.45, 145.73, 144.05, 142.58, 129.56, 121.11, 115.93, 109.61, 89.62, 80.12, 72.63, 56.20, 48.43, 28.72, 20.88, 19.42, 18.69, 16.98, 15.63; IR (thin film) 3389, 2968, 1753, 1678, 1496, 1239, 1203, 1004 cm$^{-1}$; HRMS-ESI (m/z) calc'd for [C$_{25}$H$_{33}$N$_2$O$_8$]$^+$, 489.2231; found, 489.2212.

Example A: Evaluation of Fungicidal Activity: Leaf Blotch of Wheat (*Zymoseptoria tritici*; Bayer Code SEPTTR)

Technical grades of materials were dissolved in acetone, which were then mixed with nine volumes of water (H$_2$O) containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia triticina*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 h after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D: Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 h after fungicide treatment and kept in a 22° C. dew chamber with 100% relative humidity for 48 h, and then moved to a greenhouse set at 20° C. for disease to develop. Fungicide formulation, application and disease assessment on the sprayed leaves followed the procedures as described in the Example A.

Example E: Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 h after fungicide treatments. Inoculated plants were kept in a dew chamber at 22° C. for 48 h then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example F: Evaluation of Fungicidal Activity: Asian Soybean Rust (*Phakopsora pachyrhizi*; Bayer Code PHAKPA)

Technical grades of materials were dissolved in acetone, which were then mixed with nine volumes of $H_2O$ containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example G: Evaluation of Fungicidal Activity: Barley Scald (*Rhyncosporium secalis*, Bayer Code RHYNSE)

Barley seedlings (variety Harrington) were propagated in soil-less Metro mix, with each pot having 8 to 12 plants, and used in the test when the first leaf was fully emerged. Test plants were inoculated by an aqueous spore suspension of *Rhyncosporium secalis* 24 h after fungicide treatments. After inoculation the plants were kept in a dew room at 22° C. with 100% relative humidity for 48 h. The plants were then transferred to a greenhouse set at 20° C. for disease to develop. Fungicide formulation, application and disease assessment on the sprayed leaves followed the procedures as described in the Example A.

Example H: Evaluation of Fungicidal Activity: Rice Blast (*Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 h after fungicide treatments. After inoculation the plants were kept in a dew room at 22° C. with 100% relative humidity for 48 h to permit spores to germinate and infect the leaf. The plants were then transferred to a greenhouse set at 24° C. for disease to develop. Fungicide formulation, application and disease assessment on the sprayed leaves followed the procedures as described in the Example A.

Example I: Evaluation of Fungicidal Activity: Tomato Early Blight (*Alternaria solani*; Bayer Code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 h after fungicide treatments. After inoculation the plants were kept at 22° C. in 100% relative humidity for 48 h to permit spores to germinate and infect the leaf. The plants were then transferred to a growth room at 22° C. for disease to develop. Fungicide formulation, application and disease assessment on the sprayed leaves followed the procedures as described in the Example A.

Example J: Evaluation of Fungicidal Activity: Cucumber Anthracnose (*Colletotrichum lagenarium*; Bayer code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure, Preparation Method, and Appearance

| *Cmpd. No. | Structure | As Prepared According To | Appearance |
|---|---|---|---|
| 1 | [structure] | Example 1B; Example 2, Example 3C; Example 4B; Example 5B; Example 6B; Example 10A; Example 11. | Clear, Colorless Oil |
| 2 | [structure] | Example 1B; Example 2, Example 3C; Example 4B; Example 5B; Example 6B; Example 10A; Example 11; Example 12B. | Clear, Colorless Oil |
| 3 | [structure] | Example 1A; Example 3A; Example 11. | Clear, Colorless Oil |
| 4 | [structure] | Example 1A; Example 3A; Example 11. | Clear, Colorless Oil |
| 5 | [structure] | Example 1A; Example 3A; Example 11. | Clear, Colorless Oil |

TABLE 1-continued

Compound Structure, Preparation Method, and Appearance

| *Cmpd. No. | Structure | As Prepared According To | Appearance |
|---|---|---|---|
| 6 | 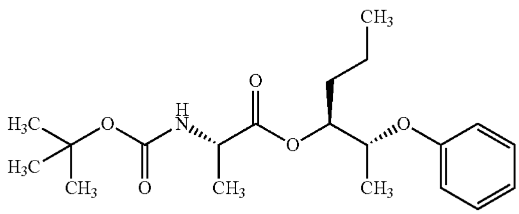 [SMILES: CCC[C@H](OC(=O)[C@H](C)NC(=O)OC(C)(C)C)[C@@H](C)Oc1ccccc1] | Example 1A; Example 3A; Example 11. | Clear, Colorless Oil |
| 7 | 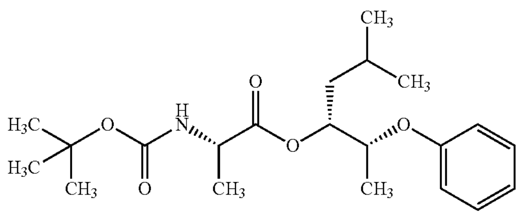 [SMILES: CC(C)C[C@@H](OC(=O)[C@H](C)NC(=O)OC(C)(C)C)[C@@H](C)Oc1ccccc1] | Example 1A; Example 3A; Example 11. | Clear, Colorless Oil |
| 8 | 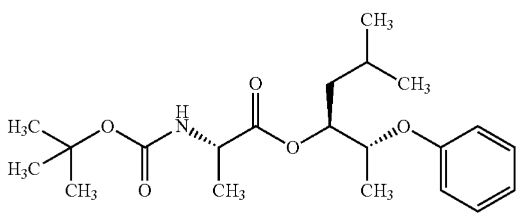 [SMILES: CC(C)C[C@H](OC(=O)[C@H](C)NC(=O)OC(C)(C)C)[C@@H](C)Oc1ccccc1] | Example 1A; Example 3A; Example 11. | Clear, Colorless Oil |
| 9 | 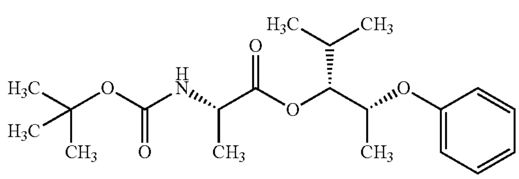 [SMILES: CC(C)[C@@H](OC(=O)[C@H](C)NC(=O)OC(C)(C)C)[C@@H](C)Oc1ccccc1] | Example 1A; Example 3A; Example 11. | Clear, Colorless Oil |
| 10 | 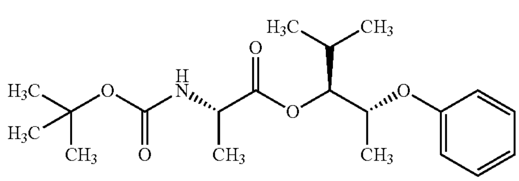 [SMILES: CC(C)[C@H](OC(=O)[C@H](C)NC(=O)OC(C)(C)C)[C@@H](C)Oc1ccccc1] | Example 1A; Example 3A; Example 11. | Clear, Colorless Oil |
| 11 | 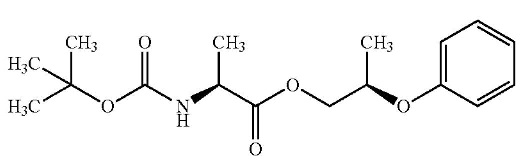 [SMILES: C[C@H](COC(=O)[C@H](C)NC(=O)OC(C)(C)C)Oc1ccccc1] | Example 1A; Example 3A; Example 11. | Clear, Colorless Oil |
| 12 | 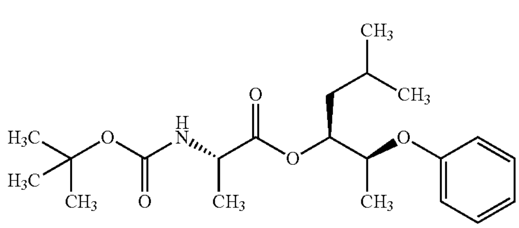 [SMILES: CC(C)C[C@H](OC(=O)[C@H](C)NC(=O)OC(C)(C)C)[C@H](C)Oc1ccccc1] | Example 1A; Example 3A; Example 11. | Clear, Colorless Oil |

TABLE 1-continued

Compound Structure, Preparation Method, and Appearance

| *Cmpd. No. | Structure | As Prepared According To | Appearance |
|---|---|---|---|
| 13 | 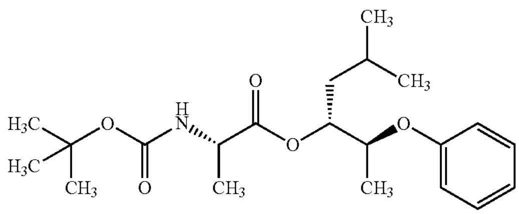 [SMILES: CC(C)C[C@@H](OC(=O)[C@H](C)NC(=O)OC(C)(C)C)[C@H](C)Oc1ccccc1] | Example 1A; Example 3A; Example 11. | Clear, Colorless Oil |
| 14 | 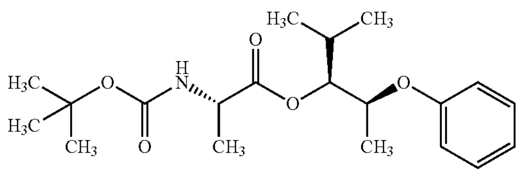 [SMILES: CC(C)[C@H](OC(=O)[C@H](C)NC(=O)OC(C)(C)C)[C@H](C)Oc1ccccc1] | Example 1A; Example 3A; Example 11. | Clear, Colorless Oil |
| 15 | 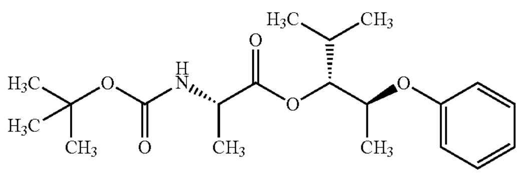 [SMILES: CC(C)[C@@H](OC(=O)[C@H](C)NC(=O)OC(C)(C)C)[C@H](C)Oc1ccccc1] | Example 1A; Example 3A; Example 11. | Clear, Colorless Oil |
| 16 | 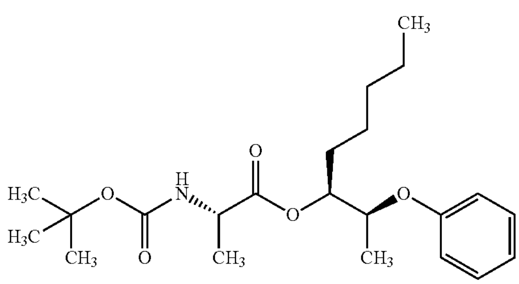 [SMILES: CCCCC[C@H](OC(=O)[C@H](C)NC(=O)OC(C)(C)C)[C@H](C)Oc1ccccc1] | Example 1A; Example 3A; Example 11. | Clear, Colorless Oil |
| 17 | 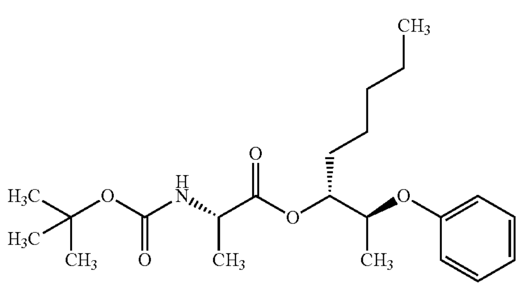 [SMILES: CCCCC[C@@H](OC(=O)[C@H](C)NC(=O)OC(C)(C)C)[C@H](C)Oc1ccccc1] | Example 1A; Example 3A; Example 11. | Clear, Colorless Oil |
| 18 | 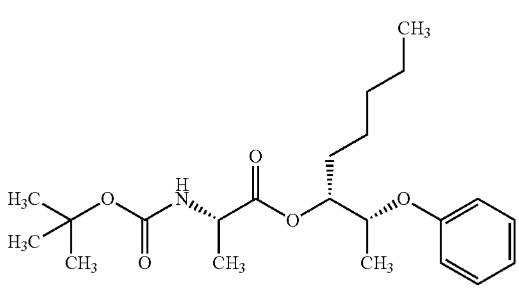 [SMILES: CCCCC[C@@H](OC(=O)[C@H](C)NC(=O)OC(C)(C)C)[C@@H](C)Oc1ccccc1] | Example 1A; Example 3A; Example 11. | Clear, Colorless Oil |

TABLE 1-continued

Compound Structure, Preparation Method, and Appearance

| *Cmpd. No. | Structure | As Prepared According To | Appearance |
|---|---|---|---|
| 19 | 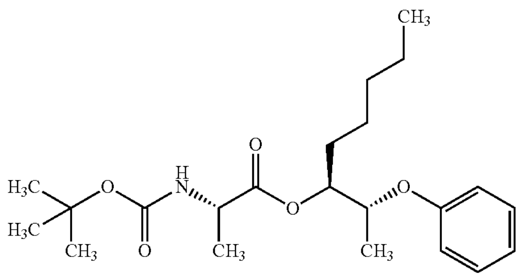 [SMILES: CCCCC[C@H](OC(=O)[C@H](C)NC(=O)OC(C)(C)C)[C@@H](C)Oc1ccccc1] | Example 1A; Example 3A; Example 11. | Clear, Colorless Oil |
| 20 | 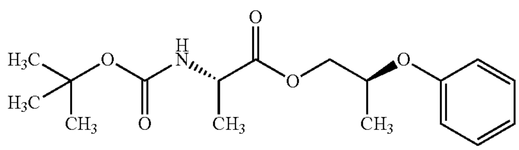 [SMILES: C[C@H](NC(=O)OC(C)(C)C)C(=O)OC[C@H](C)Oc1ccccc1] | Example 1A; Example 3A; Example 11. | Clear, Colorless Oil |
| 21 | 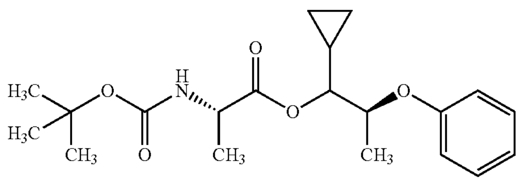 [SMILES: C[C@H](NC(=O)OC(C)(C)C)C(=O)OC(C1CC1)[C@H](C)Oc1ccccc1] | Example 1A; Example 3A; Example 11. | Clear, Colorless Oil |
| 22 | 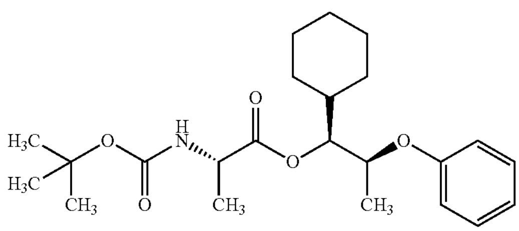 [SMILES: C[C@H](NC(=O)OC(C)(C)C)C(=O)O[C@@H](C1CCCCC1)[C@H](C)Oc1ccccc1] | Example 1A; Example 3A; Example 11. | Clear, Colorless Oil |
| 23 | 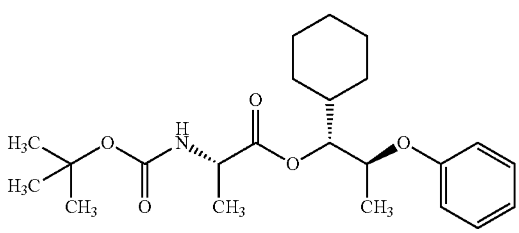 [SMILES: C[C@H](NC(=O)OC(C)(C)C)C(=O)O[C@H](C1CCCCC1)[C@H](C)Oc1ccccc1] | Example 1A; Example 3A; Example 11. | Clear, Colorless Oil |
| 24 | 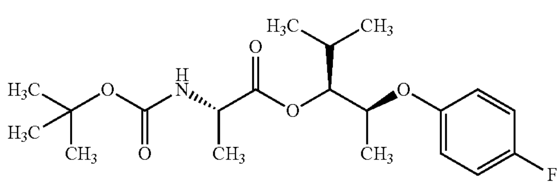 [SMILES: CC(C)[C@H](OC(=O)[C@H](C)NC(=O)OC(C)(C)C)[C@H](C)Oc1ccc(F)cc1] | Example 1A; Example 3A; Example 11. | Clear, Colorless Oil |
| 25 | 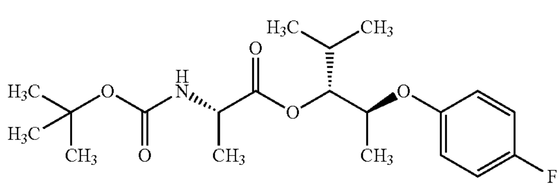 [SMILES: CC(C)[C@@H](OC(=O)[C@H](C)NC(=O)OC(C)(C)C)[C@H](C)Oc1ccc(F)cc1] | Example 1A; Example 3A; Example 11. | Clear, Colorless Oil |

TABLE 1-continued

Compound Structure, Preparation Method, and Appearance

| *Cmpd. No. | Structure | As Prepared According To | Appearance |
|---|---|---|---|
| 26 | 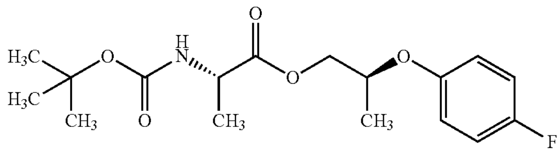 [SMILES: C[C@H](NC(=O)OC(C)(C)C)C(=O)OC[C@H](C)Oc1ccc(F)cc1] | Example 1A; Example 3A; Example 11. | Clear, Colorless Oil |
| 27 | 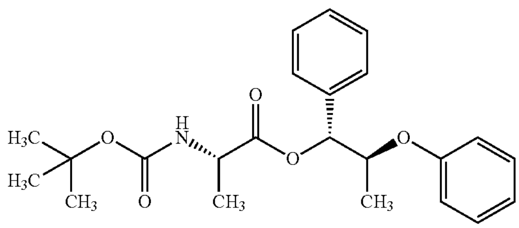 [SMILES: C[C@H](NC(=O)OC(C)(C)C)C(=O)O[C@H](c1ccccc1)[C@H](C)Oc1ccccc1] | Example 4C; Example 5C; Example 6A; Example 10B; Example 11. | Clear, Colorless Oil |
| 28 | 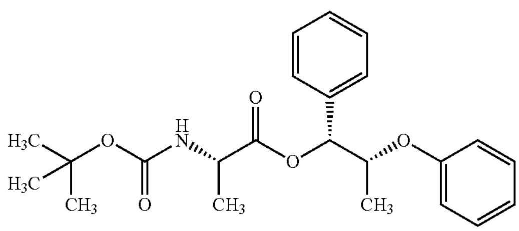 [SMILES: C[C@H](NC(=O)OC(C)(C)C)C(=O)O[C@H](c1ccccc1)[C@@H](C)Oc1ccccc1] | Example 4C; Example 5C; Example 6A; Example 10B; Example 11. | Clear, Colorless Oil |
| 29 | 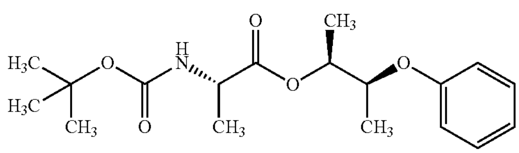 [SMILES: C[C@H](NC(=O)OC(C)(C)C)C(=O)O[C@@H](C)[C@H](C)Oc1ccccc1] | Example 1A; Example 3A; Example 11. | Clear, Colorless Oil |
| 30 | 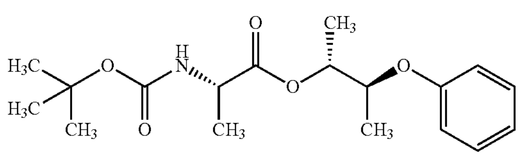 [SMILES: C[C@H](NC(=O)OC(C)(C)C)C(=O)O[C@H](C)[C@H](C)Oc1ccccc1] | Example 1A; Example 3A; Example 11. | Clear, Colorless Oil |
| 31 | 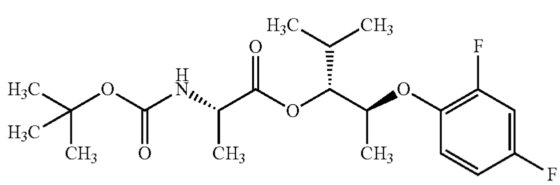 [SMILES: CC(C)[C@@H](OC(=O)[C@H](C)NC(=O)OC(C)(C)C)[C@H](C)Oc1ccc(F)cc1F] | Example 1D; Example 3A; Example 4A; Example 5A; Example 6B; Example 10C; Example 11. | Clear, Colorless Oil |
| 32 | 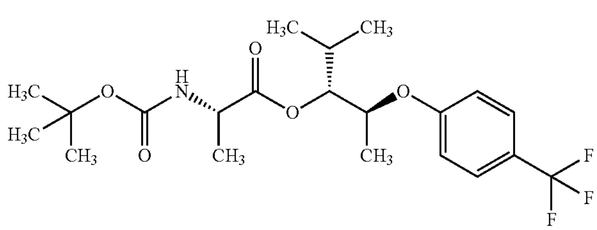 [SMILES: CC(C)[C@@H](OC(=O)[C@H](C)NC(=O)OC(C)(C)C)[C@H](C)Oc1ccc(C(F)(F)F)cc1] | Example 1D; Example 3A; Example 4A; Example 5A; Example 6B; Example 10C; Example 11. | Clear, Colorless Oil |
| 33 | 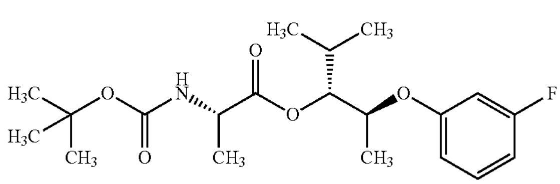 [SMILES: CC(C)[C@@H](OC(=O)[C@H](C)NC(=O)OC(C)(C)C)[C@H](C)Oc1cccc(F)c1] | Example 1D; Example 3A; Example 4A; Example 5A; Example 6B; Example 10C; Example 11. | Clear, Colorless Oil |

TABLE 1-continued

Compound Structure, Preparation Method, and Appearance

| *Cmpd. No. | Structure | As Prepared According To | Appearance |
|---|---|---|---|
| 34 | 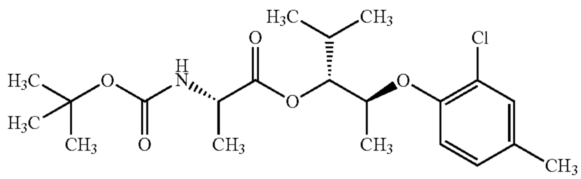 [SMILES: Cc1ccc(O[C@@H](C)[C@H](OC(=O)[C@H](C)NC(=O)OC(C)(C)C)C(C)C)c(Cl)c1] | Example 1D; Example 3A; Example 4A; Example 5A; Example 6B; Example 10C; Example 11. | Clear, Colorless Oil |
| 35 | 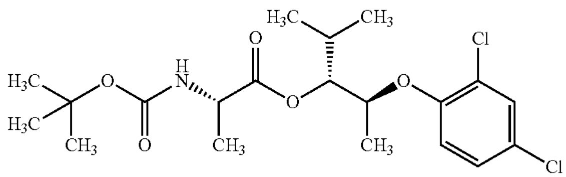 [SMILES: CC(C)[C@@H](OC(=O)[C@H](C)NC(=O)OC(C)(C)C)[C@H](C)Oc1ccc(Cl)cc1Cl] | Example 1D; Example 3A; Example 4A; Example 5A; Example 6B; Example 10C; Example 11. | Clear, Colorless Oil |
| 36 | 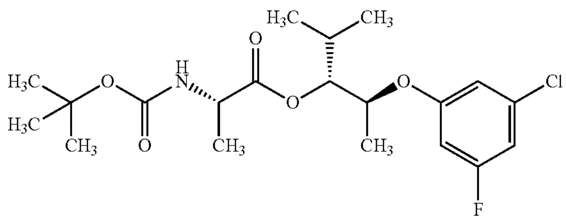 [SMILES: CC(C)[C@@H](OC(=O)[C@H](C)NC(=O)OC(C)(C)C)[C@H](C)Oc1cc(F)cc(Cl)c1] | Example 1D; Example 3A; Example 4A; Example 5A; Example 6B; Example 10C; Example 11. | Clear, Colorless Oil |
| 37 | 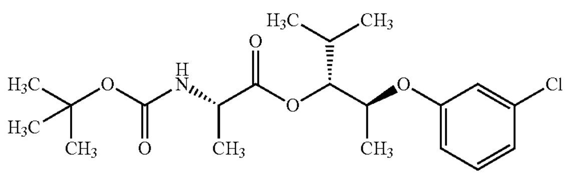 [SMILES: CC(C)[C@@H](OC(=O)[C@H](C)NC(=O)OC(C)(C)C)[C@H](C)Oc1cccc(Cl)c1] | Example 1D; Example 3A; Example 4A; Example 5A; Example 6B; Example 10C; Example 11. | Clear, Colorless Oil |
| 38 | 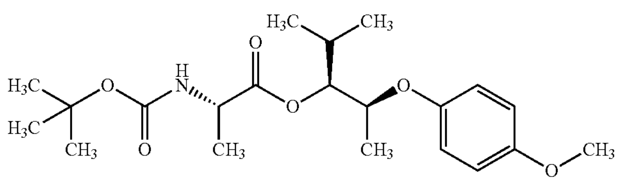 [SMILES: COc1ccc(O[C@@H](C)[C@@H](OC(=O)[C@H](C)NC(=O)OC(C)(C)C)C(C)C)cc1] | Example 1A; Example 3A; Example 11. | Clear, Colorless Oil |
| 39 | 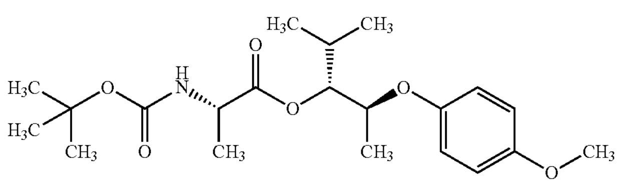 [SMILES: COc1ccc(O[C@@H](C)[C@H](OC(=O)[C@H](C)NC(=O)OC(C)(C)C)C(C)C)cc1] | Example 1A; Example 3A; Example 11. | Clear, Colorless Oil |
| 40 | 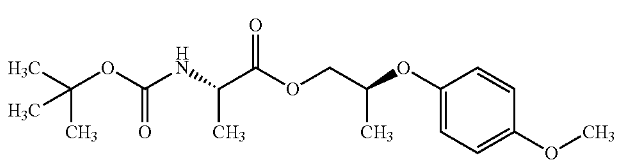 [SMILES: COc1ccc(O[C@@H](C)COC(=O)[C@H](C)NC(=O)OC(C)(C)C)cc1] | Example 1A; Example 3A; Example 11. | Clear, Colorless Oil |
| 41 | 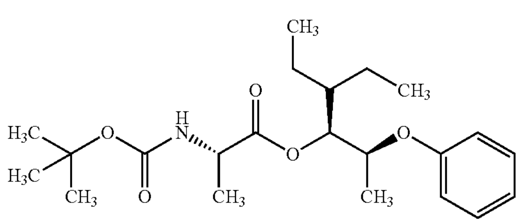 [SMILES: CCC(CC)[C@H](OC(=O)[C@H](C)NC(=O)OC(C)(C)C)[C@H](C)Oc1ccccc1] | Example 1A; Example 3A; Example 11. | Clear, Colorless Oil |

TABLE 1-continued

Compound Structure, Preparation Method, and Appearance

| *Cmpd. No. | Structure | As Prepared According To | Appearance |
|---|---|---|---|
| 42 | 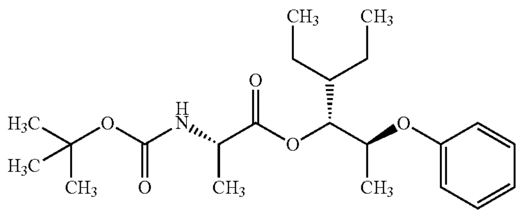 [SMILES: CCC(CC)[C@@H](OC(=O)[C@H](C)NC(=O)OC(C)(C)C)[C@H](C)Oc1ccccc1] | Example 1A; Example 3A; Example 11. | Clear, Colorless Oil |
| 43 | 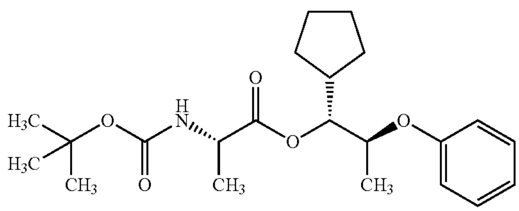 [SMILES: C[C@H](NC(=O)OC(C)(C)C)C(=O)O[C@H](C1CCCC1)[C@H](C)Oc1ccccc1] | Example 1A; Example 3A; Example 11. | Clear, Colorless Oil |
| 44 | 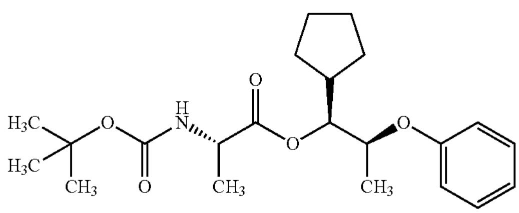 [SMILES: C[C@H](NC(=O)OC(C)(C)C)C(=O)O[C@@H](C1CCCC1)[C@H](C)Oc1ccccc1] | Example 1A; Example 3A; Example 11. | Clear, Colorless Oil |
| 45 | 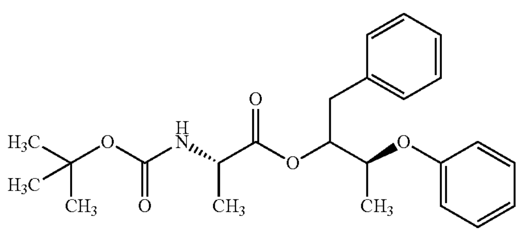 [SMILES: C[C@H](NC(=O)OC(C)(C)C)C(=O)OC(Cc1ccccc1)[C@H](C)Oc1ccccc1] | Example 1A; Example 3A; Example 11. | Clear, Colorless Oil |
| 46 | 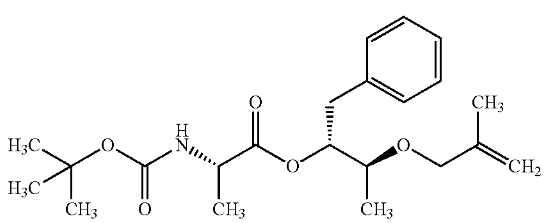 | Example 1D; Example 5C; Example 6C; Example 10A; Example 11. | Colorless Oil |
| 47 | 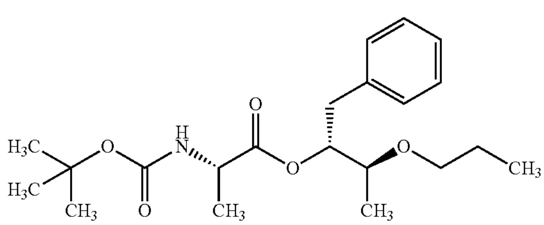 [SMILES: CCCO[C@@H](C)[C@@H](Cc1ccccc1)OC(=O)[C@H](C)NC(=O)OC(C)(C)C] | Example 1D; Example 5C; Example 6C; Example 10A; Example 11. | Colorless Oil |
| 48 | 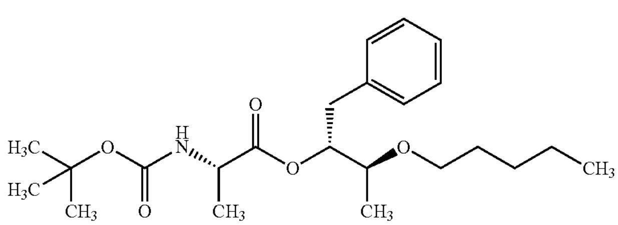 [SMILES: CCCCCO[C@@H](C)[C@@H](Cc1ccccc1)OC(=O)[C@H](C)NC(=O)OC(C)(C)C] | Example 1D; Example 5C; Example 6C; Example 10A; Example 11. | Colorless Oil |

TABLE 1-continued

Compound Structure, Preparation Method, and Appearance

| *Cmpd. No. | Structure | As Prepared According To | Appearance |
|---|---|---|---|
| 49 | 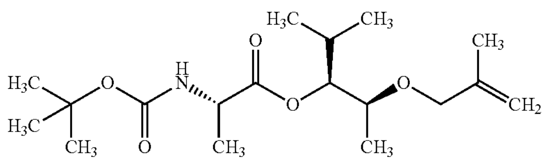 [SMILES: C=C(C)CO[C@@H](C)[C@@H](OC(=O)[C@H](C)NC(=O)OC(C)(C)C)C(C)C] | Example 1C; Example 3A; Example 11. | Colorless Oil |
| 50 | 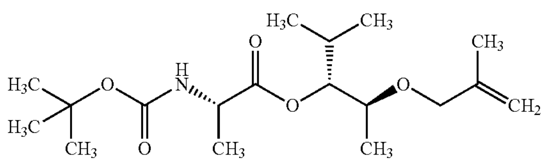 [SMILES: C=C(C)CO[C@@H](C)[C@H](OC(=O)[C@H](C)NC(=O)OC(C)(C)C)C(C)C] | Example 1C; Example 3A; Example 11. | Colorless Oil |
| 51 | 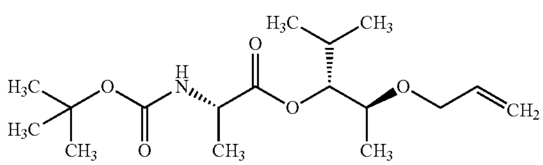 [SMILES: C=CCO[C@@H](C)[C@H](OC(=O)[C@H](C)NC(=O)OC(C)(C)C)C(C)C] | Example 1C; Example 3A; Example 11. | Colorless Oil |
| 52 | 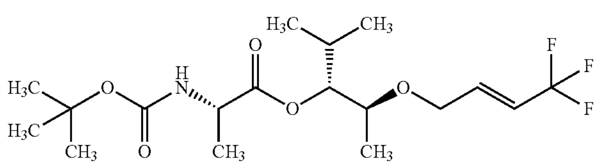 [SMILES: CC(C)[C@@H](OC(=O)[C@H](C)NC(=O)OC(C)(C)C)[C@H](C)OC/C=C/C(F)(F)F] | Example 1C; Example 3A; Example 11. | Colorless Oil |
| 53 | 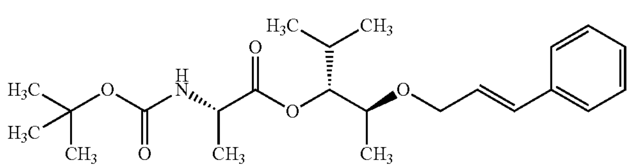 [SMILES: CC(C)[C@@H](OC(=O)[C@H](C)NC(=O)OC(C)(C)C)[C@H](C)OC/C=C/c1ccccc1] | Example 1C; Example 3A; Example 11. | Colorless Oil |
| 54 | 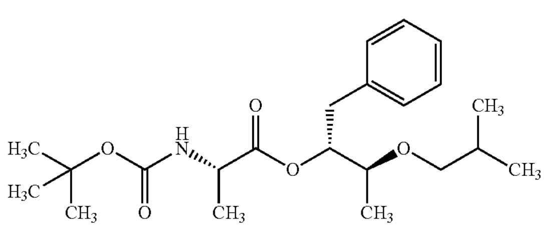 [SMILES: CC(C)CO[C@@H](C)[C@@H](Cc1ccccc1)OC(=O)[C@H](C)NC(=O)OC(C)(C)C] | Example 1D; Example 5C; Example 6C; Example 10A; Example 11; Example 12A. | Colorless Oil |
| 55 | 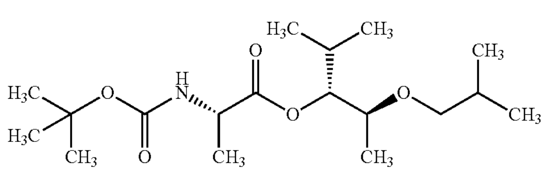 | Example 1C; Example 3A; Example 11; Example 12A. | Colorless Oil |
| 56 | 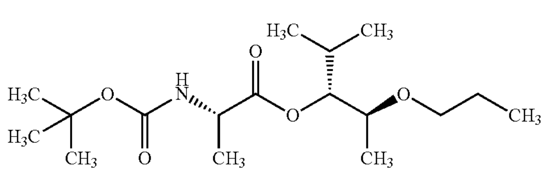 | Example 1C; Example 3A; Example 11; Example 12A. | Colorless Oil |

TABLE 1-continued

Compound Structure, Preparation Method, and Appearance

| *Cmpd. No. | Structure | As Prepared According To | Appearance |
|---|---|---|---|
| 57 | 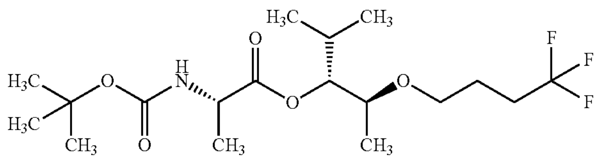 [SMILES: CC(C)[C@@H](OC(=O)[C@H](C)NC(=O)OC(C)(C)C)[C@H](C)OCCCC(F)(F)F] | Example 1C; Example 3A; Example 11; Example 12A. | Colorless Oil |
| 58 | 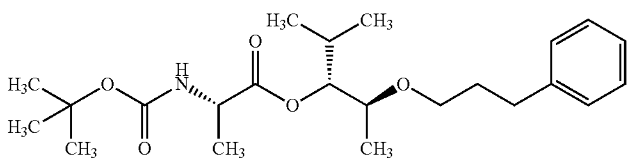 [SMILES: CC(C)[C@@H](OC(=O)[C@H](C)NC(=O)OC(C)(C)C)[C@H](C)OCCCc1ccccc1] | Example 1C; Example 3A; Example 11; Example 12A. | Colorless Oil |
| 59 | 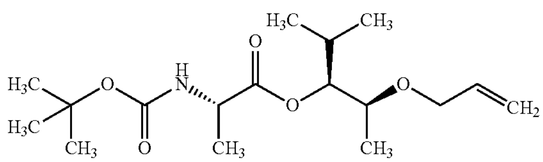 [SMILES: C=CCO[C@@H](C)[C@@H](OC(=O)[C@H](C)NC(=O)OC(C)(C)C)C(C)C] | Example 1C; Example 3A; Example 11. | Thick Oil |
| 60 | 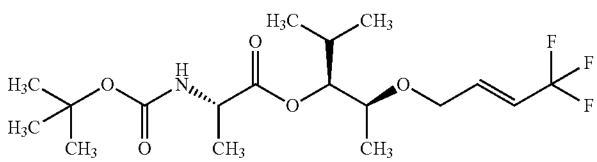 [SMILES: CC(C)[C@H](OC(=O)[C@H](C)NC(=O)OC(C)(C)C)[C@H](C)OC/C=C/C(F)(F)F] | Example 1C; Example 3A; Example 11. | Colorless Oil |
| 61 | 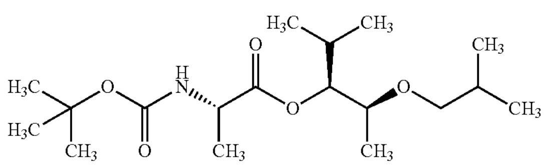 | Example 1C; Example 3A; Example 11; Example 12A. | Colorless Oil |
| 62 | 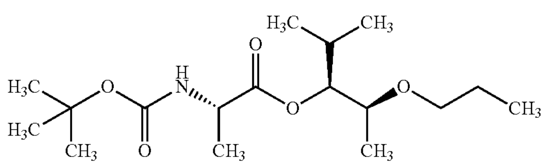 [SMILES: CCCO[C@@H](C)[C@@H](OC(=O)[C@H](C)NC(=O)OC(C)(C)C)C(C)C] | Example 1C; Example 3A; Example 11; Example 12A. | Colorless Oil |
| 63 | 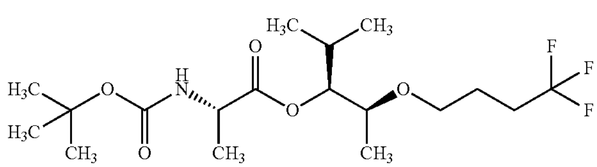 [SMILES: CC(C)[C@H](OC(=O)[C@H](C)NC(=O)OC(C)(C)C)[C@H](C)OCCCC(F)(F)F] | Example 1C; Example 3A; Example 11; Example 12A. | Colorless Oil |
| 64 | 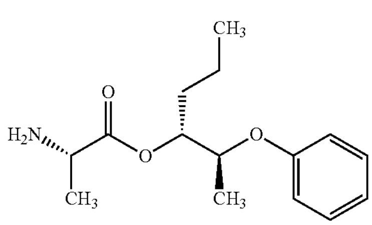 [SMILES: CCC[C@@H](OC(=O)[C@H](C)N)[C@H](C)Oc1ccccc1] | Example 13A, Step 1. | Clear, Colorless Oil |

TABLE 1-continued

Compound Structure, Preparation Method, and Appearance

| *Cmpd. No. | Structure | As Prepared According To | Appearance |
|---|---|---|---|
| 65 | 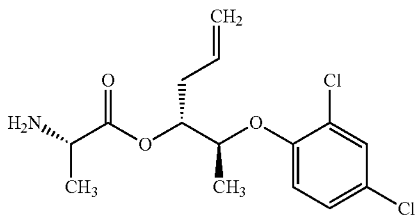 [SMILES: C=CC[C@@H](OC(=O)[C@H](C)N)[C@H](C)Oc1ccc(Cl)cc1Cl] | Example 13B, Step 1. | Clear, Colorless Oil |
| 66 | 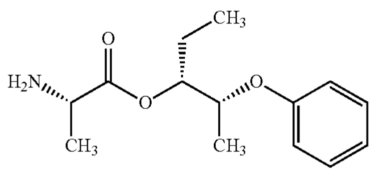 [SMILES: CC[C@@H](OC(=O)[C@H](C)N)[C@@H](C)Oc1ccccc1] | Example 13A, Step 1. | Clear, Colorless Oil |
| 67 | 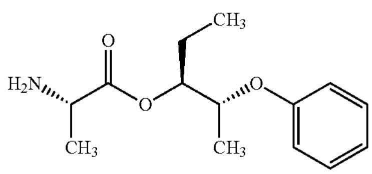 [SMILES: CC[C@H](OC(=O)[C@H](C)N)[C@@H](C)Oc1ccccc1] | Example 13A, Step 1. | Pale Yellow Oil |
| 68 | 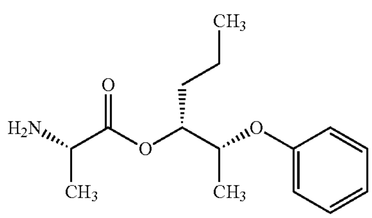 [SMILES: CCC[C@@H](OC(=O)[C@H](C)N)[C@@H](C)Oc1ccccc1] | Example 13A, Step 1. | Clear, Colorless Oil |
| 69 | 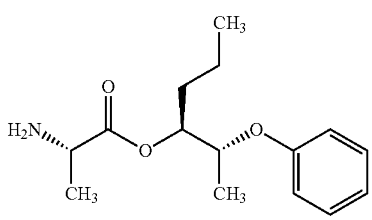 [SMILES: CCC[C@H](OC(=O)[C@H](C)N)[C@@H](C)Oc1ccccc1] | Example 13A, Step 1. | White Semisolid |
| 70 | 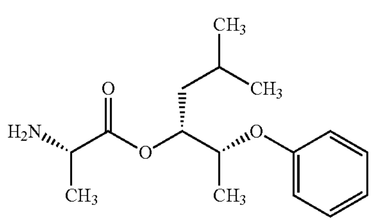 [SMILES: CC(C)C[C@@H](OC(=O)[C@H](C)N)[C@@H](C)Oc1ccccc1] | Example 13A, Step 1. | Clear, Colorless Oil |
| 71 | 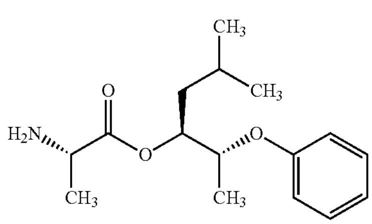 [SMILES: CC(C)C[C@H](OC(=O)[C@H](C)N)[C@@H](C)Oc1ccccc1] | Example 13A, Step 1. | Clear, Colorless Oil |

TABLE 1-continued

Compound Structure, Preparation Method, and Appearance

| *Cmpd. No. | Structure | As Prepared According To | Appearance |
|---|---|---|---|
| 72 | 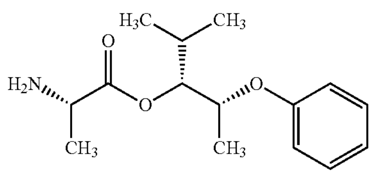 [SMILES: CC(C)[C@@H](OC(=O)[C@H](C)N)[C@@H](C)Oc1ccccc1] | Example 13A, Step 1. | White Semisolid |
| 73 | 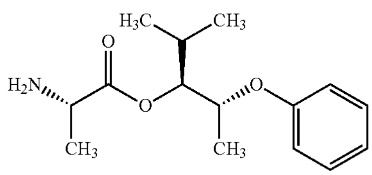 [SMILES: CC(C)[C@H](OC(=O)[C@H](C)N)[C@@H](C)Oc1ccccc1] | Example 13A, Step 1. | White Semisolid |
| 74 | 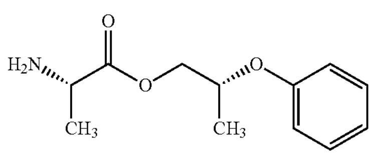 [SMILES: C[C@H](COC(=O)[C@H](C)N)Oc1ccccc1] | Example 13A, Step 1. | White Semisolid |
| 75 | 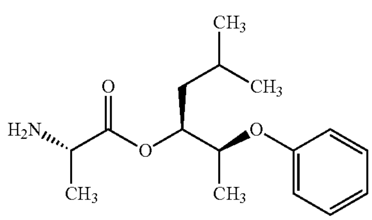 [SMILES: CC(C)C[C@H](OC(=O)[C@H](C)N)[C@H](C)Oc1ccccc1] | Example 13A, Step 1. | Clear, Colorless Oil |
| 76 | 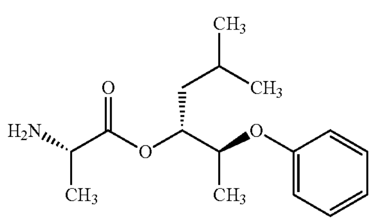 [SMILES: CC(C)C[C@@H](OC(=O)[C@H](C)N)[C@H](C)Oc1ccccc1] | Example 13A, Step 1. | Clear, Colorless Oil |
| 77 | 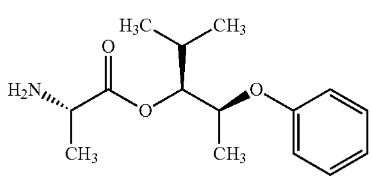 [SMILES: CC(C)[C@H](OC(=O)[C@H](C)N)[C@H](C)Oc1ccccc1] | Example 13A, Step 1. | White Solid |
| 78 | 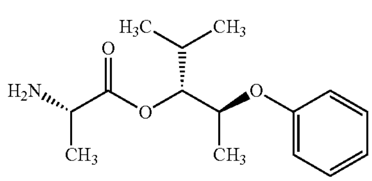 [SMILES: CC(C)[C@@H](OC(=O)[C@H](C)N)[C@H](C)Oc1ccccc1] | Example 13A, Step 1. | White Solid |

TABLE 1-continued

Compound Structure, Preparation Method, and Appearance

| *Cmpd. No. | Structure | As Prepared According To | Appearance |
|---|---|---|---|
| 79 | 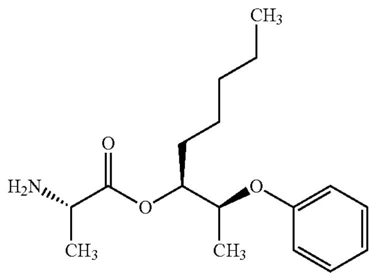 [SMILES: CCCCC[C@H](OC(=O)[C@H](C)N)[C@H](C)Oc1ccccc1] | Example 13A, Step 1. | Clear, Colorless Oil |
| 80 | 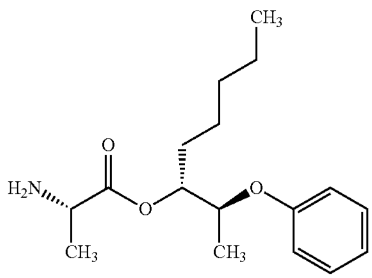 [SMILES: CCCCC[C@@H](OC(=O)[C@H](C)N)[C@H](C)Oc1ccccc1] | Example 13A, Step 1. | Clear, Colorless Oil |
| 81 | 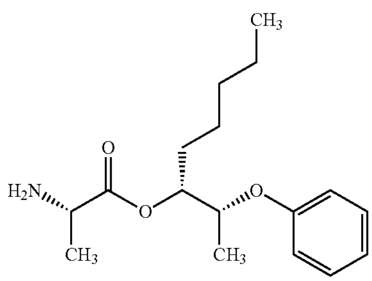 [SMILES: CCCCC[C@@H](OC(=O)[C@H](C)N)[C@@H](C)Oc1ccccc1] | Example 13A, Step 1. | White Solid |
| 82 | 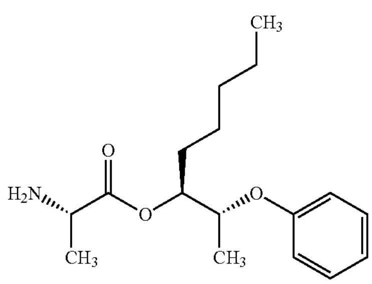 [SMILES: CCCCC[C@H](OC(=O)[C@H](C)N)[C@@H](C)Oc1ccccc1] | Example 13A, Step 1. | White Solid |
| 83 | 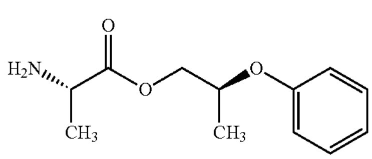 [SMILES: C[C@H](N)C(=O)OC[C@H](C)Oc1ccccc1] | Example 13A, Step 1. | White Solid |
| 84 | 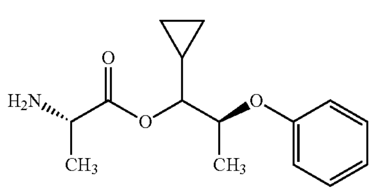 [SMILES: C[C@H](N)C(=O)OC(C1CC1)[C@H](C)Oc1ccccc1] | Example 13A, Step 1. | Pale Yellow Oil |

TABLE 1-continued

Compound Structure, Preparation Method, and Appearance

| *Cmpd. No. | Structure | As Prepared According To | Appearance |
|---|---|---|---|
| 85 | 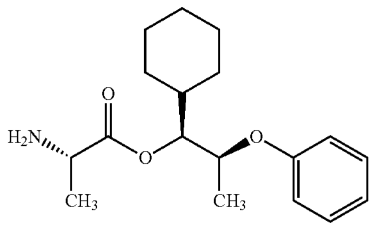 [SMILES: C[C@H](N)C(=O)O[C@@H](C1CCCCC1)[C@H](C)Oc1ccccc1] | Example 13A, Step 1. | White Semisolid |
| 86 | 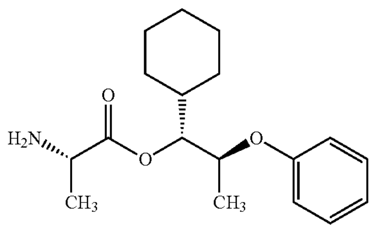 [SMILES: C[C@H](N)C(=O)O[C@H](C1CCCCC1)[C@H](C)Oc1ccccc1] | Example 13A, Step 1. | White Solid |
| 87 | 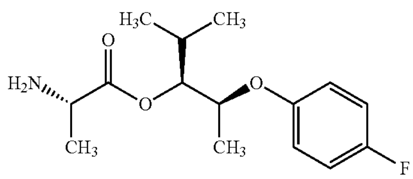 [SMILES: CC(C)[C@H](OC(=O)[C@H](C)N)[C@H](C)Oc1ccc(F)cc1] | Example 13A, Step 1. | Pale Yellow Oil |
| 88 | 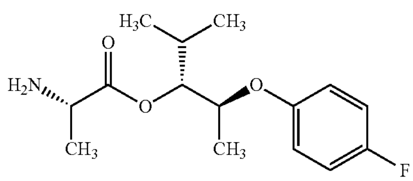 [SMILES: CC(C)[C@@H](OC(=O)[C@H](C)N)[C@H](C)Oc1ccc(F)cc1] | Example 13A, Step 1. | Pale Yellow Oil |
| 89 | 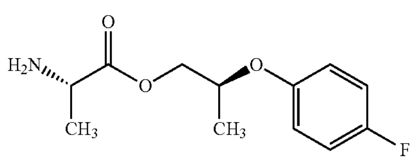 [SMILES: C[C@H](N)C(=O)OC[C@H](C)Oc1ccc(F)cc1] | Example 13A, Step 1. | White Semisolid |
| 90 | 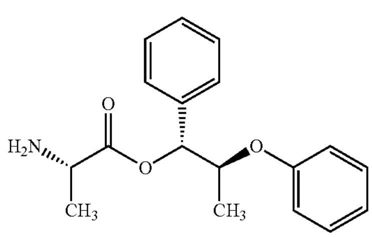 [SMILES: C[C@H](N)C(=O)O[C@H](c1ccccc1)[C@H](C)Oc1ccccc1] | Example 13A, Step 1. | Clear, Colorless Oil |
| 91 | 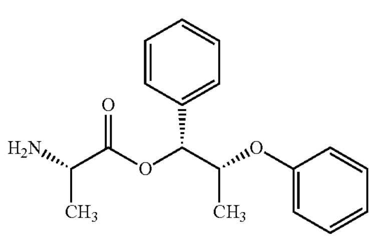 [SMILES: C[C@H](N)C(=O)O[C@H](c1ccccc1)[C@@H](C)Oc1ccccc1] | Example 13A, Step 1. | Clear, Colorless Oil |

TABLE 1-continued

Compound Structure, Preparation Method, and Appearance

| *Cmpd. No. | Structure | As Prepared According To | Appearance |
|---|---|---|---|
| 92 | alanine ester with 1-phenoxypropan-2-yl group | Example 13A, Step 1. | Clear, Colorless Oil |
| 93 | alanine ester with 1-phenoxypropan-2-yl group (diastereomer) | Example 13A, Step 1. | Clear, Colorless Oil |
| 94 | alanine ester with 3-methyl-1-(2,4-difluorophenoxy)butan-2-yl group | Example 13A, Step 1. | White Semisolid |
| 95 | alanine ester with 3-methyl-1-(4-trifluoromethylphenoxy)butan-2-yl group | Example 13A, Step 1. | Clear, Colorless Oil |
| 96 | alanine ester with 3-methyl-1-(3-fluorophenoxy)butan-2-yl group | Example 13A, Step 1. | White Semisolid |
| 97 | alanine ester with 3-methyl-1-(2-chloro-4-methylphenoxy)butan-2-yl group | Example 13A, Step 1. | Clear, Colorless Oil |
| 98 | alanine ester with 3-methyl-1-(2,4-dichlorophenoxy)butan-2-yl group | Example 13A, Step 1. | Clear, Colorless Oil |
| 99 | alanine ester with 3-methyl-1-(3-chloro-5-fluorophenoxy)butan-2-yl group | Example 13A, Step 1. | Clear, Colorless Oil |

TABLE 1-continued

Compound Structure, Preparation Method, and Appearance

| *Cmpd. No. | Structure | As Prepared According To | Appearance |
|---|---|---|---|
| 100 | 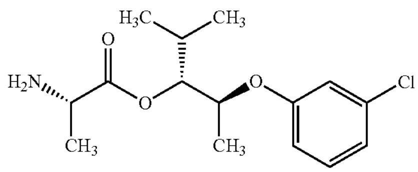 [SMILES: CC(C)[C@@H](OC(=O)[C@H](C)N)[C@H](C)Oc1cccc(Cl)c1] | Example 13A, Step 1. | White Semisolid |
| 101 | 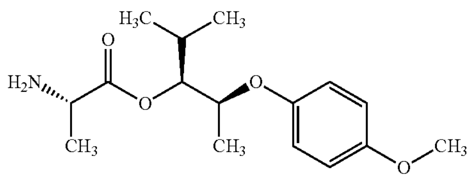 [SMILES: COc1ccc(O[C@@H](C)[C@@H](OC(=O)[C@H](C)N)C(C)C)cc1] | Example 13A, Step 1. | White Powdery Solid |
| 102 | 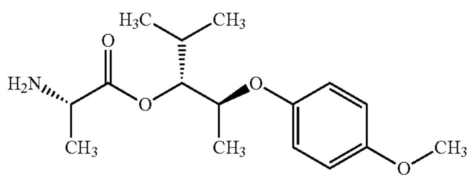 [SMILES: COc1ccc(O[C@@H](C)[C@H](OC(=O)[C@H](C)N)C(C)C)cc1] | Example 13A, Step 1. | White Powdery Solid |
| 103 | 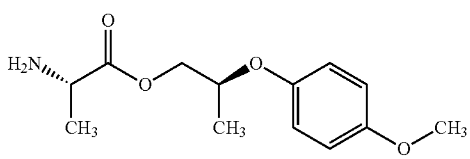 [SMILES: COc1ccc(O[C@@H](C)COC(=O)[C@H](C)N)cc1] | Example 13A, Step 1. | White Powdery Solid |
| 104 | 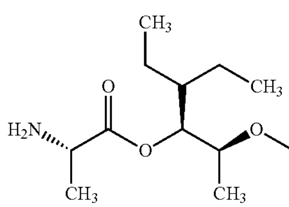 | Example 13A, Step 1. | Pale Yellow Oil |
| 105 | 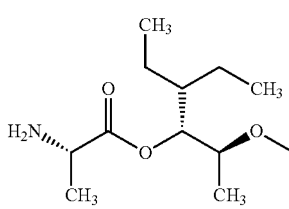 | Example 13A, Step 1. | Pale Yellow Oil |
| 106 | 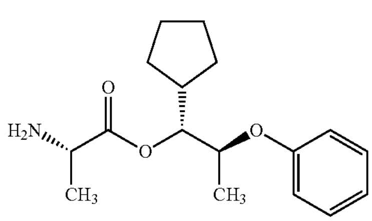 [SMILES: C[C@H](N)C(=O)O[C@H](C1CCCC1)[C@H](C)Oc1ccccc1] | Example 13A, Step 1. | Pale Yellow Oil |

TABLE 1-continued

Compound Structure, Preparation Method, and Appearance

| *Cmpd. No. | Structure | As Prepared According To | Appearance |
|---|---|---|---|
| 107 | (cyclopentyl-substituted alanine ester with phenoxy group) | Example 13A, Step 1. | Pale Yellow Oil |
| 108 | (benzyl-substituted alanine ester with phenoxy group) | Example 13A, Step 1. | Yellow Liquid |
| 109 | (benzyl-substituted alanine ester with propoxy group) | Example 13A, Step 1. | Thick Oil |
| 110 | (benzyl-substituted alanine ester with pentyloxy group) | Example 13A, Step 1. | Thick Oil |
| 111 | (benzyl-substituted alanine ester with isobutoxy group) | Example 13A, Step 1. | Thick Oil |
| 112 | (isopropyl-substituted alanine ester with isobutoxy group) | Example 13A, Step 1. | White Solid |
| 113 | (isopropyl-substituted alanine ester with propoxy group) | Example 13A, Step 1. | Thick Oil |

TABLE 1-continued

Compound Structure, Preparation Method, and Appearance

| *Cmpd. No. | Structure | As Prepared According To | Appearance |
|---|---|---|---|
| 114 | (structure) | Example 13A, Step 1. | White Solid |
| 115 | (structure) | Example 13A, Step 1. | Thick Oil |
| 116 | (structure) | Example 13B, Step 1. | Thick Oil |
| 117 | (structure) | Example 13B, Step 1. | Thick Oil |
| 118 | (structure) | Example 13B, Step 1. | Thick Oil |
| 119 | (structure) | Example 13A, Step 1. | White Solid |
| 120 | (structure) | Example 13A, Step 1. | White Solid |
| 121 | (structure) | Example 13A, Step 1. | White Solid |

TABLE 1-continued

Compound Structure, Preparation Method, and Appearance

| *Cmpd. No. | Structure | As Prepared According To | Appearance |
|---|---|---|---|
| 122 | (structure) | Example 13A, Step 2. | Clear, Colorless Oil |
| 123 | (structure) | Example 13B, Step 2. | Clear, Colorless Oil |
| 124 | (structure) | Example 13A, Step 2. | Clear, Colorless Oil |
| 125 | (structure) | Example 13A, Step 2. | Clear, Colorless Oil |
| 126 | (structure) | Example 13A, Step 2. | Clear, Colorless Oil |
| 127 | (structure) | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 128 | 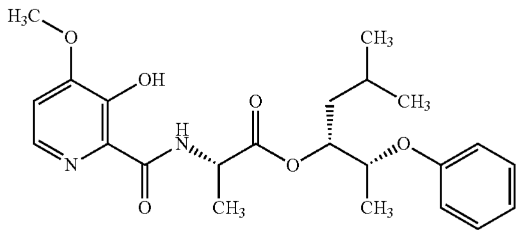 [SMILES: COc1ccnc(C(=O)N[C@@H](C)C(=O)O[C@H](CC(C)C)[C@@H](C)Oc2ccccc2)c1O] | Example 13A, Step 2. | Clear, Colorless Oil |
| 129 | 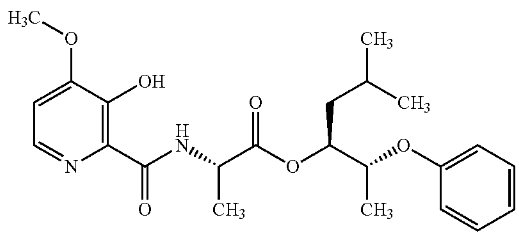 [SMILES: COc1ccnc(C(=O)N[C@@H](C)C(=O)O[C@@H](CC(C)C)[C@@H](C)Oc2ccccc2)c1O] | Example 13A, Step 2. | Clear, Colorless Oil |
| 130 | 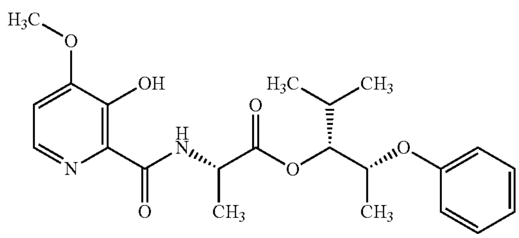 [SMILES: COc1ccnc(C(=O)N[C@@H](C)C(=O)O[C@H](C(C)C)[C@@H](C)Oc2ccccc2)c1O] | Example 13A, Step 2. | Clear, Colorless Oil |
| 131 | 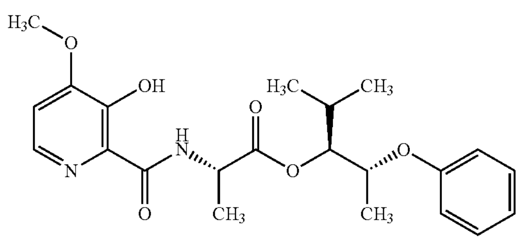 [SMILES: COc1ccnc(C(=O)N[C@@H](C)C(=O)O[C@@H](C(C)C)[C@@H](C)Oc2ccccc2)c1O] | Example 13A, Step 2. | White Powdery Solid |
| 132 | 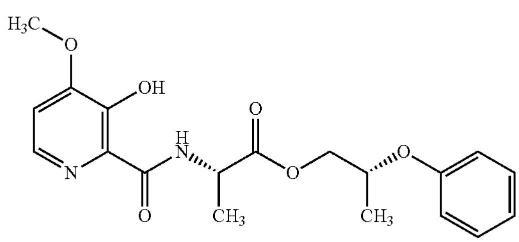 [SMILES: COc1ccnc(C(=O)N[C@@H](C)C(=O)OC[C@@H](C)Oc2ccccc2)c1O] | Example 13A, Step 2. | Clear, Colorless Oil |
| 133 | 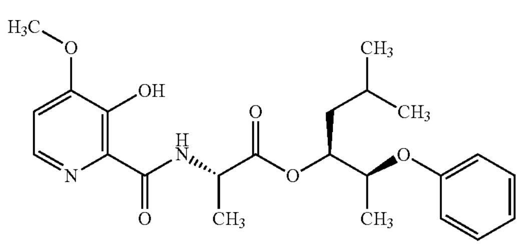 [SMILES: COc1ccnc(C(=O)N[C@@H](C)C(=O)O[C@@H](CC(C)C)[C@H](C)Oc2ccccc2)c1O] | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 134 | 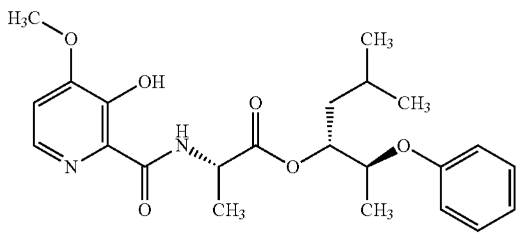 [SMILES: COc1ccnc(C(=O)N[C@@H](C)C(=O)O[C@H](CC(C)C)[C@H](C)Oc2ccccc2)c1O] | Example 13A, Step 2. | Clear, Colorless Oil |
| 135 | 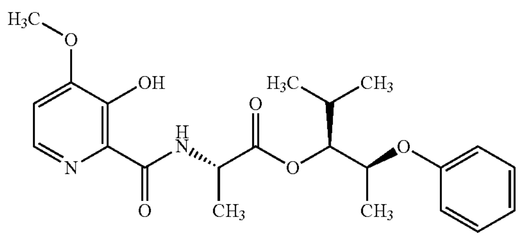 [SMILES: COc1ccnc(C(=O)N[C@@H](C)C(=O)O[C@@H](C(C)C)[C@H](C)Oc2ccccc2)c1O] | Example 13A, Step 2. | Clear, Colorless Oil |
| 136 | 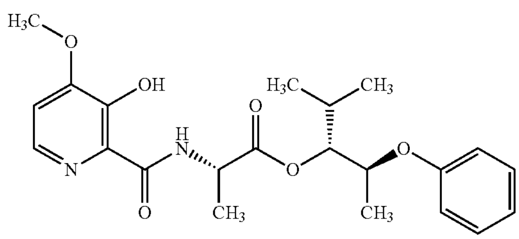 [SMILES: COc1ccnc(C(=O)N[C@@H](C)C(=O)O[C@H](C(C)C)[C@H](C)Oc2ccccc2)c1O] | Example 13A, Step 2. | Clear, Colorless Oil |
| 137 | 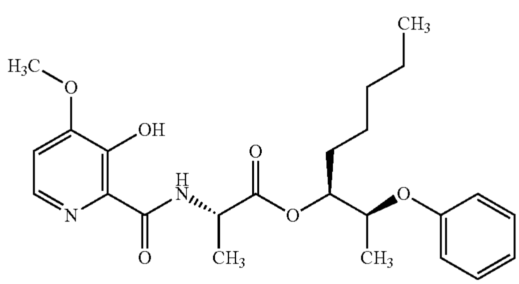 [SMILES: CCCCC[C@H](OC(=O)[C@H](C)NC(=O)c1nccc(OC)c1O)[C@H](C)Oc1ccccc1] | Example 13A, Step 2. | Clear, Colorless Oil |
| 138 | 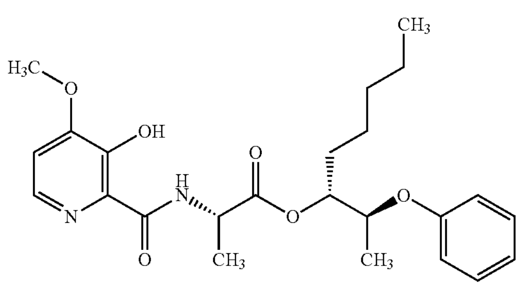 | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 139 | 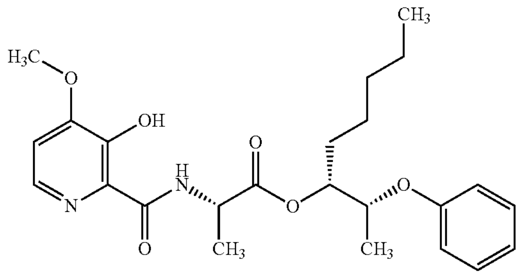 [SMILES: CCCCC[C@@H](OC(=O)[C@H](C)NC(=O)c1nccc(OC)c1O)[C@@H](C)Oc1ccccc1] | Example 13A, Step 2. | Clear, Colorless Oil |
| 140 | 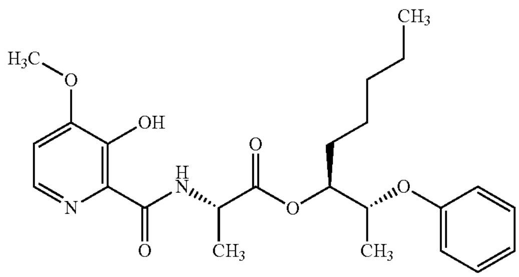 [SMILES: CCCCC[C@H](OC(=O)[C@H](C)NC(=O)c1nccc(OC)c1O)[C@@H](C)Oc1ccccc1] | Example 13A, Step 2. | Clear, Colorless Oil |
| 141 | 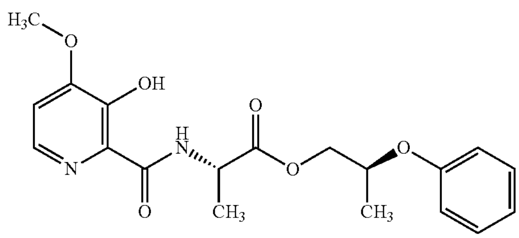 [SMILES: COc1ccnc(C(=O)N[C@@H](C)C(=O)OC[C@H](C)Oc2ccccc2)c1O] | Example 13A, Step 2. | Clear, Colorless Oil |
| 142 | 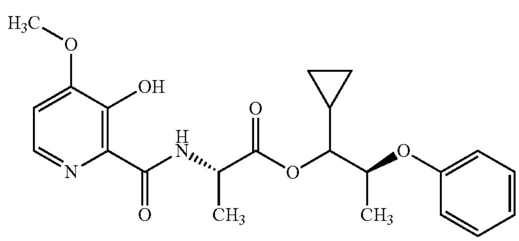 [SMILES: COc1ccnc(C(=O)N[C@@H](C)C(=O)OC(C2CC2)[C@H](C)Oc2ccccc2)c1O] | Example 13A, Step 2. | Clear, Colorless Oil |
| 143 | 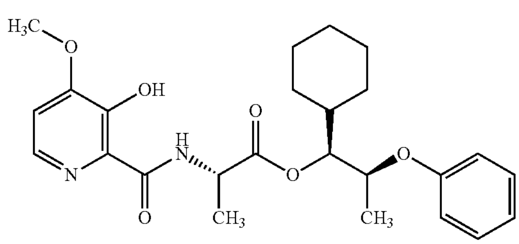 [SMILES: COc1ccnc(C(=O)N[C@@H](C)C(=O)O[C@@H](C2CCCCC2)[C@H](C)Oc2ccccc2)c1O] | Example 13A, Step 2. | Clear, Colorless Oil |
| 144 | 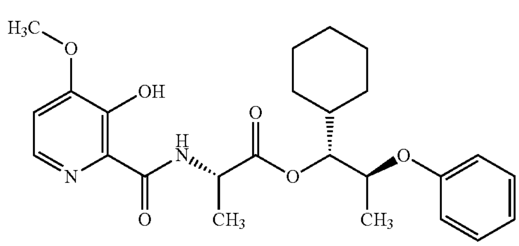 [SMILES: COc1ccnc(C(=O)N[C@@H](C)C(=O)O[C@H](C2CCCCC2)[C@H](C)Oc2ccccc2)c1O] | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 145 | 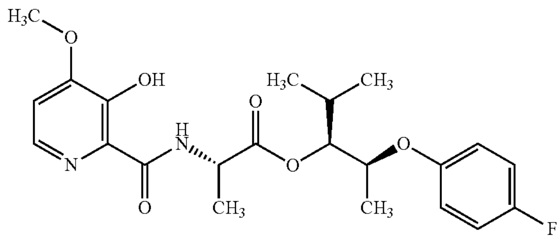 [SMILES: COc1ccnc(C(=O)N[C@@H](C)C(=O)O[C@@H](C(C)C)[C@H](C)Oc2ccc(F)cc2)c1O] | Example 13A, Step 2. | Clear, Colorless Oil |
| 146 | 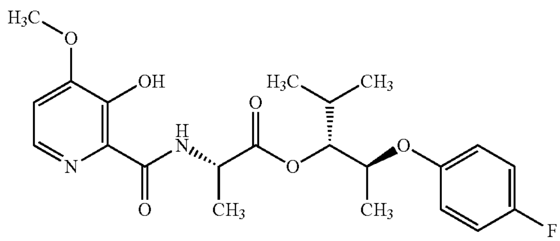 [SMILES: COc1ccnc(C(=O)N[C@@H](C)C(=O)O[C@H](C(C)C)[C@H](C)Oc2ccc(F)cc2)c1O] | Example 13A, Step 2. | Clear, Colorless Oil |
| 147 | 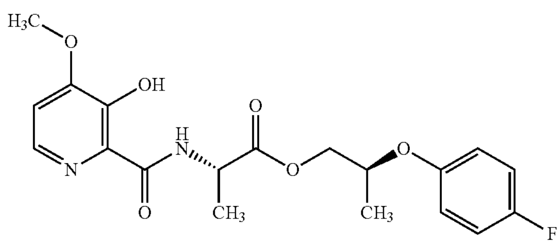 [SMILES: COc1ccnc(C(=O)N[C@@H](C)C(=O)OC[C@H](C)Oc2ccc(F)cc2)c1O] | Example 13A, Step 2. | Clear, Colorless Oil |
| 148 | 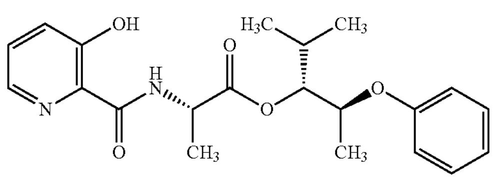 [SMILES: CC(C)[C@@H](OC(=O)[C@H](C)NC(=O)c1ncccc1O)[C@H](C)Oc1ccccc1] | Example 13A, Step 2. | Pale Yellow Oil |
| 149 | 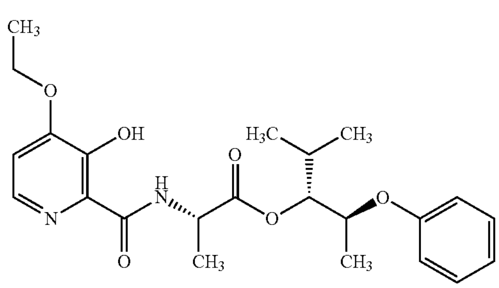 [SMILES: CCOc1ccnc(C(=O)N[C@@H](C)C(=O)O[C@H](C(C)C)[C@H](C)Oc2ccccc2)c1O] | Example 13A, Step 2. | Clear, Colorless Oil |
| 153 | 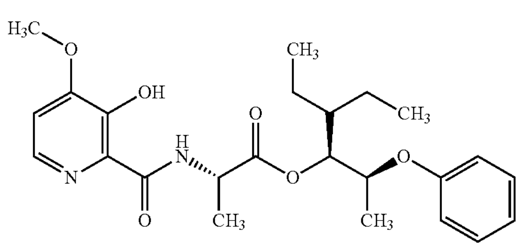 [SMILES: CCC(CC)[C@H](OC(=O)[C@H](C)NC(=O)c1nccc(OC)c1O)[C@H](C)Oc1ccccc1] | Example 13A, Step 2. | Orange-Brown Liquid |

TABLE 1-continued

Compound Structure, Preparation Method, and Appearance

| *Cmpd. No. | Structure | As Prepared According To | Appearance |
|---|---|---|---|
| 154 | 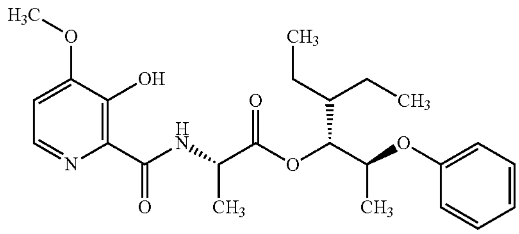 [SMILES: CCC(CC)[C@@H](OC(=O)[C@H](C)NC(=O)c1nccc(OC)c1O)[C@H](C)Oc1ccccc1] | Example 13A, Step 2. | Yellow Liquid |
| 155 | 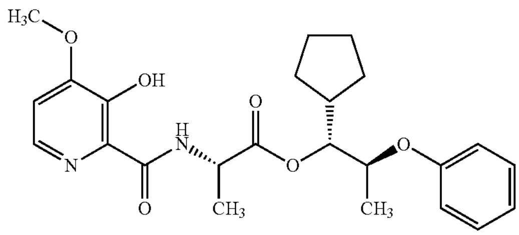 [SMILES: COc1ccnc(C(=O)N[C@@H](C)C(=O)O[C@H](C2CCCC2)[C@H](C)Oc2ccccc2)c1O] | Example 13A, Step 2. | Yellow Orange Liquid |
| 156 | 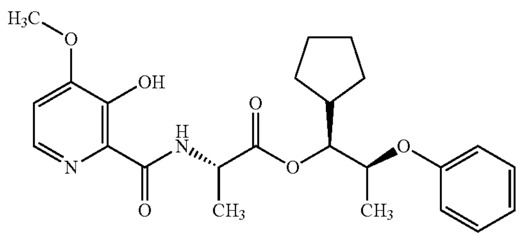 [SMILES: COc1ccnc(C(=O)N[C@@H](C)C(=O)O[C@@H](C2CCCC2)[C@H](C)Oc2ccccc2)c1O] | Example 13A, Step 2. | Dark Green Liquid |
| 157 | 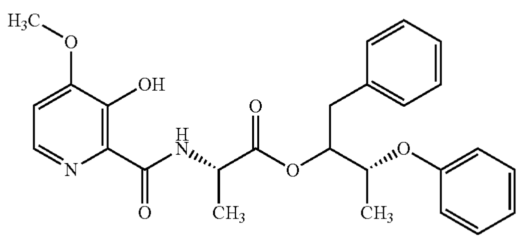 [SMILES: COc1ccnc(C(=O)N[C@@H](C)C(=O)OC(Cc2ccccc2)[C@@H](C)Oc2ccccc2)c1O] | Example 13A, Step 2. | Orange Liquid |
| 158 | 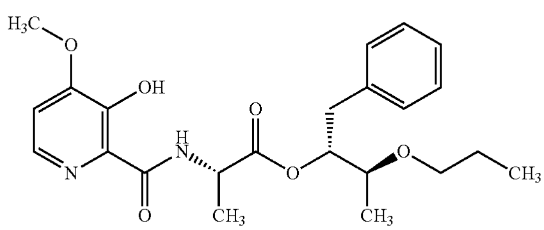 [SMILES: CCCO[C@@H](C)[C@@H](Cc1ccccc1)OC(=O)[C@H](C)NC(=O)c1nccc(OC)c1O] | Example 13A, Step 2. | Thick Oil |
| 159 | 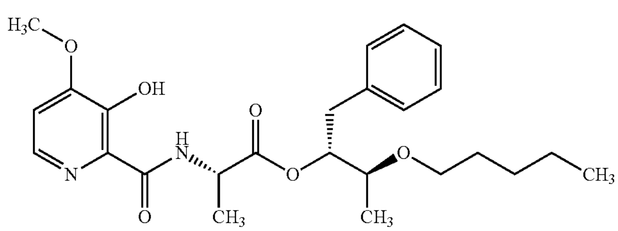 [SMILES: CCCCCO[C@@H](C)[C@@H](Cc1ccccc1)OC(=O)[C@H](C)NC(=O)c1nccc(OC)c1O] | Example 13A, Step 2. | Thick Oil |

TABLE 1-continued

Compound Structure, Preparation Method, and Appearance

| *Cmpd. No. | Structure | As Prepared According To | Appearance |
|---|---|---|---|
| 160 | 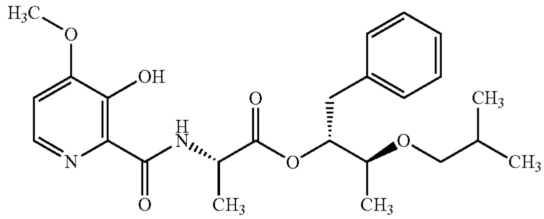 [SMILES: COc1ccnc(C(=O)N[C@@H](C)C(=O)O[C@H](Cc2ccccc2)[C@H](C)OCC(C)C)c1O] | Example 13A, Step 2. | Thick Oil |
| 161 | 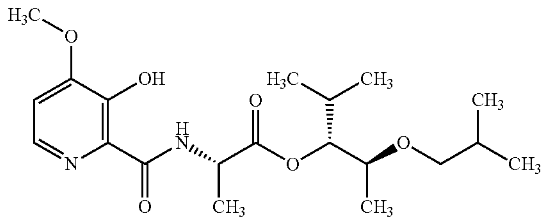 [SMILES: COc1ccnc(C(=O)N[C@@H](C)C(=O)O[C@H](C(C)C)[C@H](C)OCC(C)C)c1O] | Example 13A, Step 2. | Thick Oil |
| 162 | 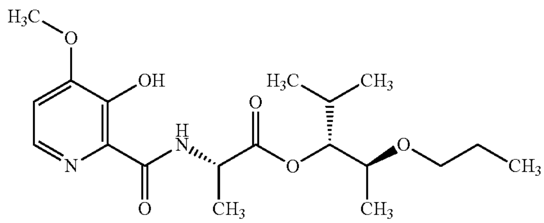 [SMILES: CCCO[C@@H](C)[C@H](OC(=O)[C@H](C)NC(=O)c1nccc(OC)c1O)C(C)C] | Example 13A, Step 2. | Thick Oil |
| 163 | 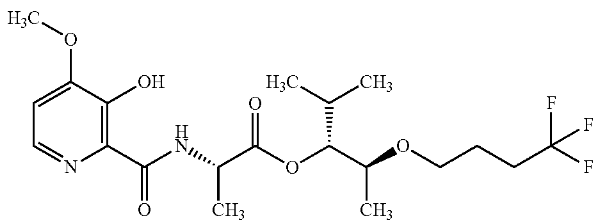 [SMILES: COc1ccnc(C(=O)N[C@@H](C)C(=O)O[C@H](C(C)C)[C@H](C)OCCCC(F)(F)F)c1O] | Example 13A, Step 2. | Thick Oil |
| 164 | 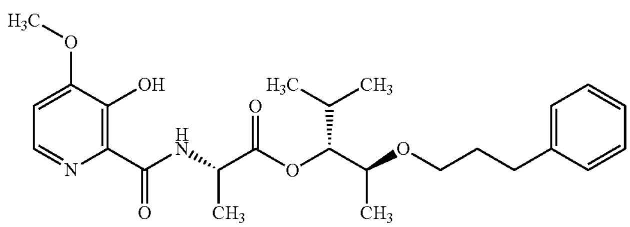 [SMILES: COc1ccnc(C(=O)N[C@@H](C)C(=O)O[C@H](C(C)C)[C@H](C)OCCCc2ccccc2)c1O] | Example 13A, Step 2. | Thick Oil |
| 165 | 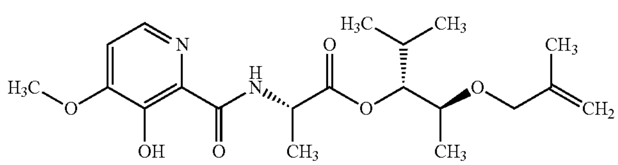 [SMILES: C=C(C)CO[C@@H](C)[C@H](OC(=O)[C@H](C)NC(=O)c1nccc(OC)c1O)C(C)C] | Example 13B, Step 2. | Thick Oil |
| 166 | 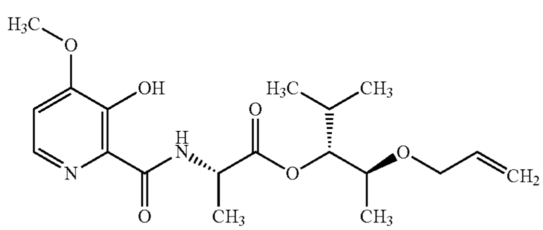 [SMILES: C=CCO[C@@H](C)[C@H](OC(=O)[C@H](C)NC(=O)c1nccc(OC)c1O)C(C)C] | Example 13B, Step 2. | Thick Oil |

TABLE 1-continued

Compound Structure, Preparation Method, and Appearance

| *Cmpd. No. | Structure | As Prepared According To | Appearance |
|---|---|---|---|
| 167 | 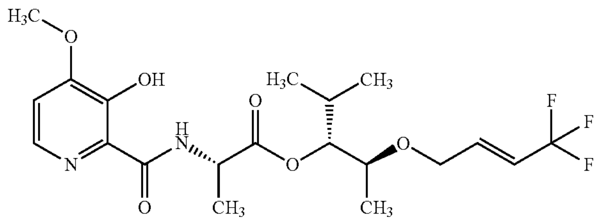 [SMILES: COc1ccnc(C(=O)N[C@@H](C)C(=O)O[C@H](C(C)C)[C@H](C)OC/C=C/C(F)(F)F)c1O] | Example 13B, Step 2. | Thick Oil |
| 168 | 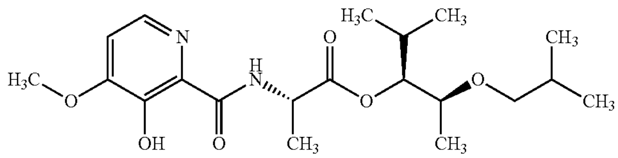 [SMILES: COc1ccnc(C(=O)N[C@@H](C)C(=O)O[C@@H](C(C)C)[C@H](C)OCC(C)C)c1O] | Example 13A, Step 2. | Thick Oil |
| 169 | 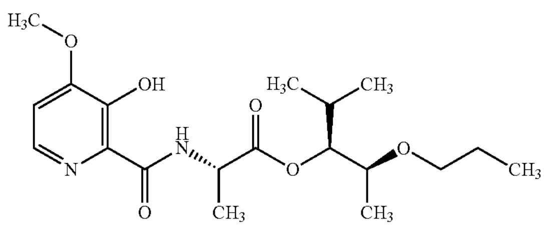 [SMILES: CCCO[C@@H](C)[C@@H](OC(=O)[C@H](C)NC(=O)c1nccc(OC)c1O)C(C)C] | Example 13A, Step 2. | Thick Oil |
| 170 | 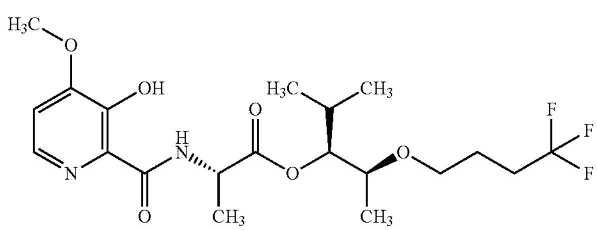 [SMILES: COc1ccnc(C(=O)N[C@@H](C)C(=O)O[C@@H](C(C)C)[C@H](C)OCCCC(F)(F)F)c1O] | Example 13A, Step 2. | Thick Oil |
| 171 | 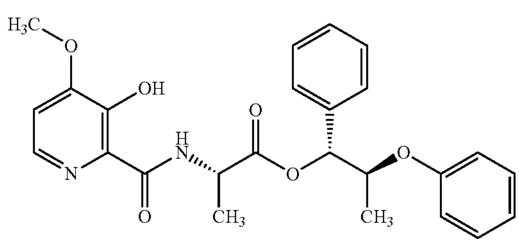 [SMILES: COc1ccnc(C(=O)N[C@@H](C)C(=O)O[C@H](c2ccccc2)[C@H](C)Oc2ccccc2)c1O] | Example 13A, Step 2. | Clear, Colorless Oil |
| 172 | 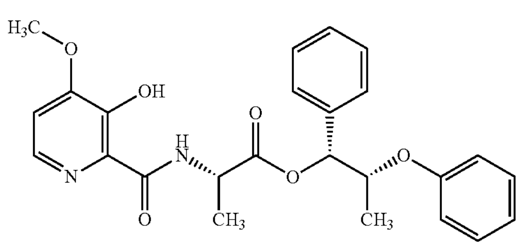 [SMILES: COc1ccnc(C(=O)N[C@@H](C)C(=O)O[C@H](c2ccccc2)[C@@H](C)Oc2ccccc2)c1O] | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 173 | 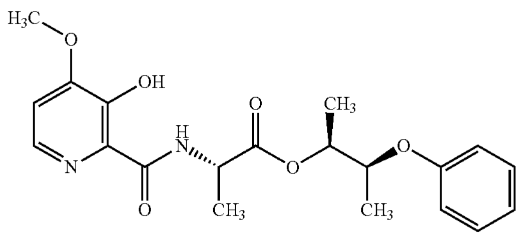 [SMILES: COc1ccnc(C(=O)N[C@@H](C)C(=O)O[C@@H](C)[C@H](C)Oc2ccccc2)c1O] | Example 13A, Step 2. | Clear, Colorless Oil |
| 174 | 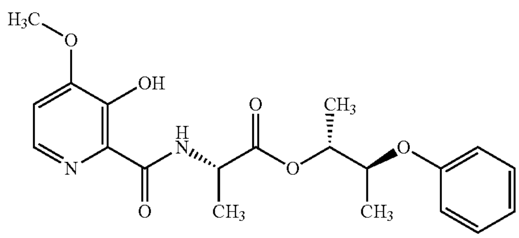 [SMILES: COc1ccnc(C(=O)N[C@@H](C)C(=O)O[C@H](C)[C@H](C)Oc2ccccc2)c1O] | Example 13A, Step 2. | Clear, Colorless Oil |
| 175 | 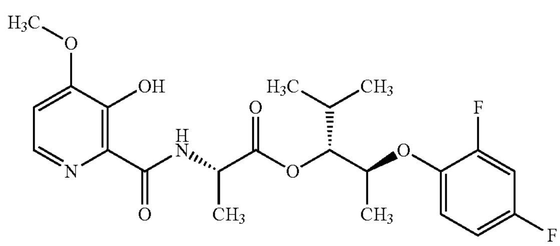 [SMILES: COc1ccnc(C(=O)N[C@@H](C)C(=O)O[C@H](C(C)C)[C@H](C)Oc2ccc(F)cc2F)c1O] | Example 13A, Step 2. | Clear, Colorless Oil |
| 176 | 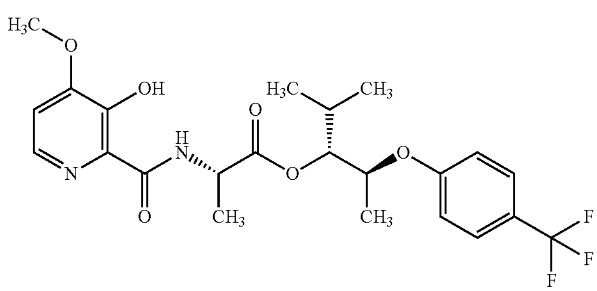 [SMILES: COc1ccnc(C(=O)N[C@@H](C)C(=O)O[C@H](C(C)C)[C@H](C)Oc2ccc(C(F)(F)F)cc2)c1O] | Example 13A, Step 2. | Clear, Colorless Oil |
| 177 | 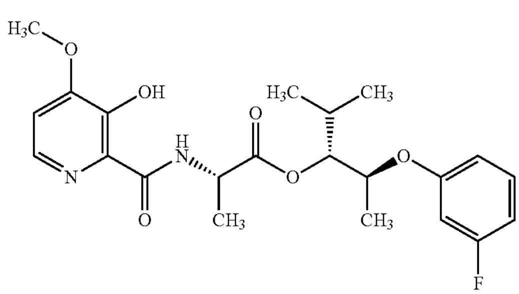 [SMILES: COc1ccnc(C(=O)N[C@@H](C)C(=O)O[C@H](C(C)C)[C@H](C)Oc2cccc(F)c2)c1O] | Example 13A, Step 2. | Clear, Colorless Oil |
| 178 | 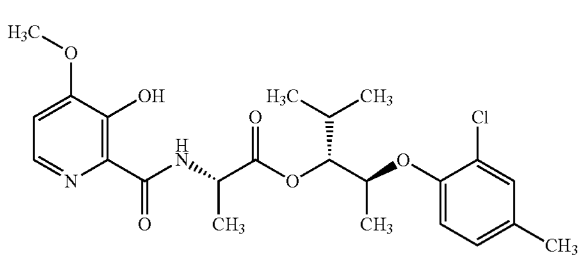 [SMILES: COc1ccnc(C(=O)N[C@@H](C)C(=O)O[C@H](C(C)C)[C@H](C)Oc2ccc(C)cc2Cl)c1O] | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 179 | 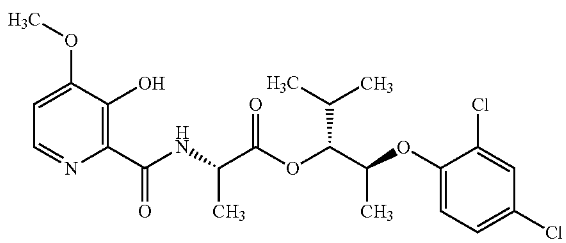 [SMILES: COc1ccnc(C(=O)N[C@@H](C)C(=O)O[C@H](C(C)C)[C@H](C)Oc2ccc(Cl)cc2Cl)c1O] | Example 13A, Step 2. | Clear, Colorless Oil |
| 180 | 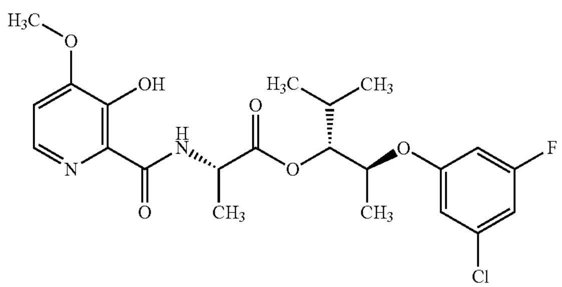 [SMILES: COc1ccnc(C(=O)N[C@@H](C)C(=O)O[C@H](C(C)C)[C@H](C)Oc2cc(F)cc(Cl)c2)c1O] | Example 13A, Step 2. | Clear, Colorless Oil |
| 181 | 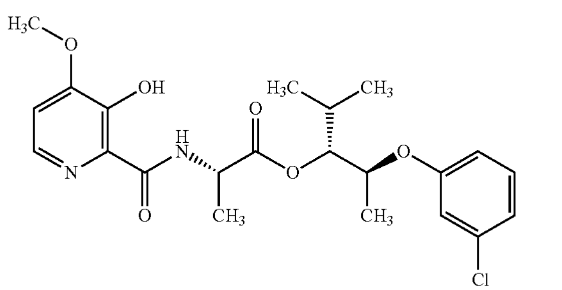 [SMILES: COc1ccnc(C(=O)N[C@@H](C)C(=O)O[C@H](C(C)C)[C@H](C)Oc2cccc(Cl)c2)c1O] | Example 13A, Step 2. | Clear, Colorless Oil |
| 182 | 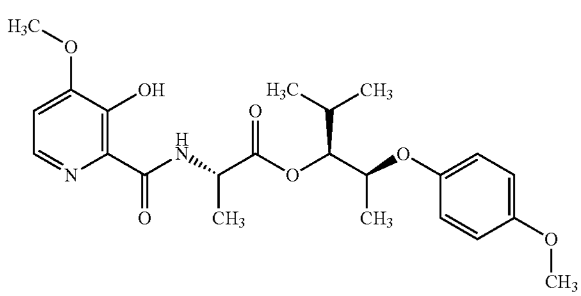 [SMILES: COc1ccc(O[C@@H](C)[C@@H](OC(=O)[C@H](C)NC(=O)c2nccc(OC)c2O)C(C)C)cc1] | Example 13A, Step 2. | Clear, Colorless Oil |
| 183 | 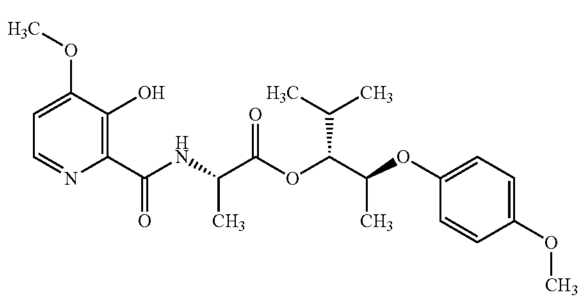 [SMILES: COc1ccc(O[C@@H](C)[C@H](OC(=O)[C@H](C)NC(=O)c2nccc(OC)c2O)C(C)C)cc1] | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 184 | 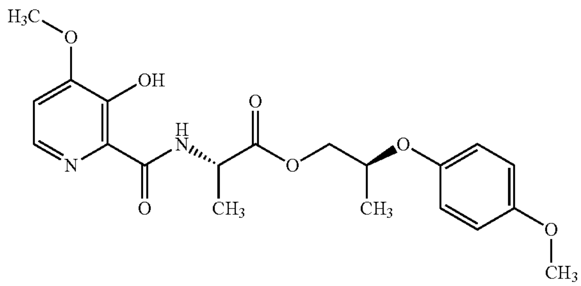 [SMILES: COc1ccc(O[C@@H](C)COC(=O)[C@H](C)NC(=O)c2nccc(OC)c2O)cc1] | Example 13A, Step 2. | Clear, Colorless Oil |
| 185 | 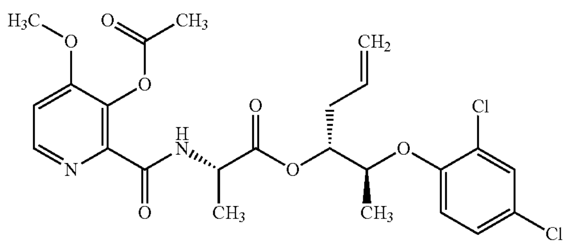 [SMILES: C=CC[C@@H](OC(=O)[C@H](C)NC(=O)c1nccc(OC)c1OC(C)=O)[C@H](C)Oc1ccc(Cl)cc1Cl] | Example 14A. | Pale Yellow Oil |
| 186 | 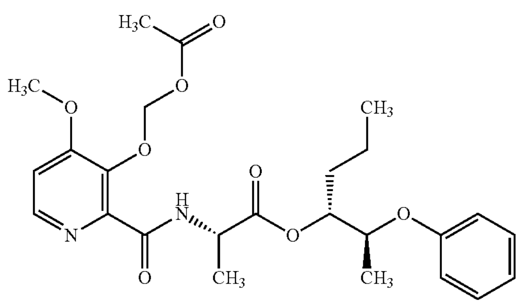 [SMILES: CCC[C@@H](OC(=O)[C@H](C)NC(=O)c1nccc(OC)c1OCOC(C)=O)[C@H](C)Oc1ccccc1] | Example 14B. | Pale Yellow Oil |
| 187 | 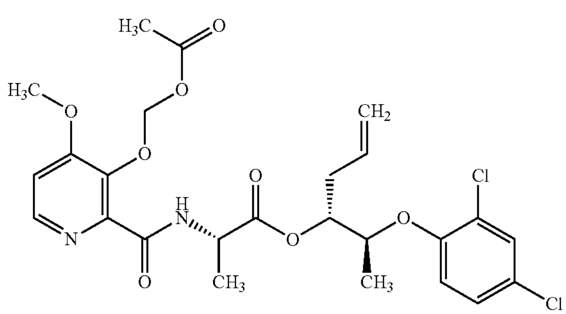 [SMILES: C=CC[C@@H](OC(=O)[C@H](C)NC(=O)c1nccc(OC)c1OCOC(C)=O)[C@H](C)Oc1ccc(Cl)cc1Cl] | Example 14B. | Pale Yellow Oil |
| 188 | 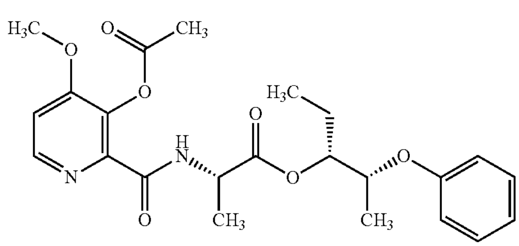 [SMILES: CC[C@@H](OC(=O)[C@H](C)NC(=O)c1nccc(OC)c1OC(C)=O)[C@@H](C)Oc1ccccc1] | Example 14A. | Clear, Colorless Oil |

TABLE 1-continued

Compound Structure, Preparation Method, and Appearance

| *Cmpd. No. | Structure | As Prepared According To | Appearance |
|---|---|---|---|
| 189 | 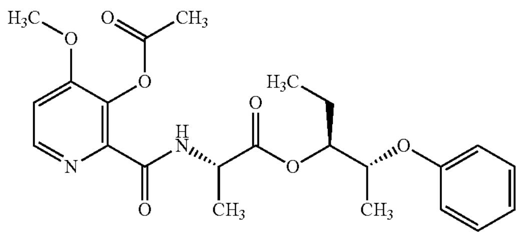 [SMILES: CC[C@H](OC(=O)[C@H](C)NC(=O)c1nccc(OC)c1OC(C)=O)[C@@H](C)Oc1ccccc1] | Example 14A. | Pale Yellow Oil |
| 190 | 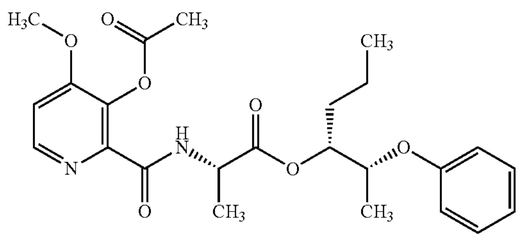 [SMILES: CCC[C@@H](OC(=O)[C@H](C)NC(=O)c1nccc(OC)c1OC(C)=O)[C@@H](C)Oc1ccccc1] | Example 14A. | Pale, Yellow Oil |
| 191 | 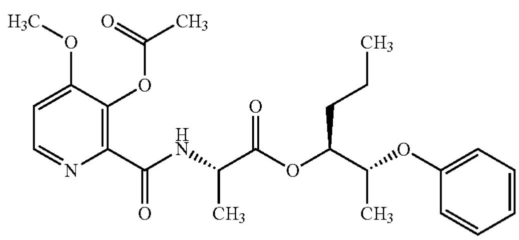 [SMILES: CCC[C@H](OC(=O)[C@H](C)NC(=O)c1nccc(OC)c1OC(C)=O)[C@@H](C)Oc1ccccc1] | Example 14A. | Pale Yellow Oil |
| 192 | 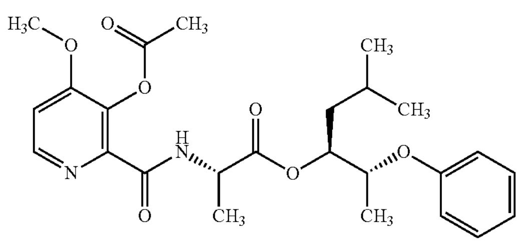 [SMILES: COc1ccnc(C(=O)N[C@@H](C)C(=O)O[C@@H](CC(C)C)[C@@H](C)Oc2ccccc2)c1OC(C)=O] | Example 14A. | Clear, Colorless Oil |
| 193 | 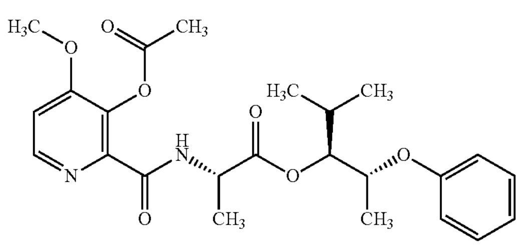 [SMILES: COc1ccnc(C(=O)N[C@@H](C)C(=O)O[C@@H](C(C)C)[C@@H](C)Oc2ccccc2)c1OC(C)=O] | Example 14A. | Pale Yellow Oil |
| 194 | 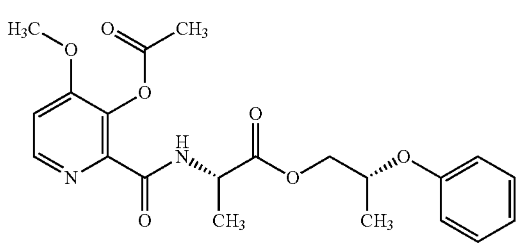 [SMILES: COc1ccnc(C(=O)N[C@@H](C)C(=O)OC[C@@H](C)Oc2ccccc2)c1OC(C)=O] | Example 14A. | Pale Yellow Oil |

TABLE 1-continued

Compound Structure, Preparation Method, and Appearance

| *Cmpd. No. | Structure | As Prepared According To | Appearance |
|---|---|---|---|
| 195 | 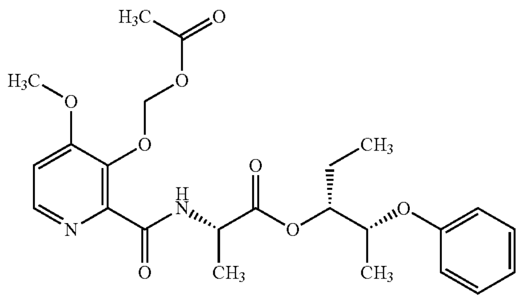 [SMILES: CC[C@@H](OC(=O)[C@H](C)NC(=O)c1nccc(OC)c1OCOC(C)=O)[C@@H](C)Oc1ccccc1] | Example 14B. | Clear, Colorless Oil |
| 196 | 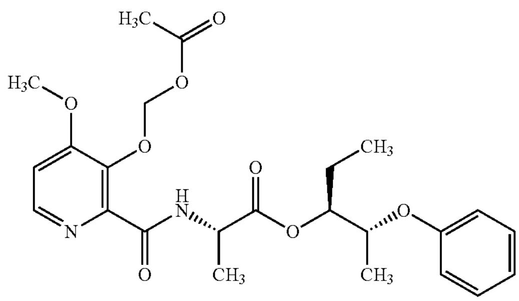 [SMILES: CC[C@H](OC(=O)[C@H](C)NC(=O)c1nccc(OC)c1OCOC(C)=O)[C@@H](C)Oc1ccccc1] | Example 14B. | Pale Yellow Oil |
| 197 | 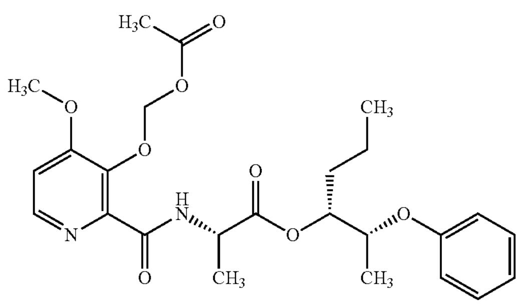 [SMILES: CCC[C@@H](OC(=O)[C@H](C)NC(=O)c1nccc(OC)c1OCOC(C)=O)[C@@H](C)Oc1ccccc1] | Example 14B. | Clear, Colorless Oil |
| 198 | 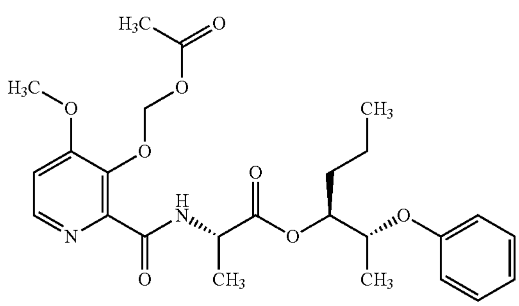 [SMILES: CCC[C@H](OC(=O)[C@H](C)NC(=O)c1nccc(OC)c1OCOC(C)=O)[C@@H](C)Oc1ccccc1] | Example 14B. | Pale Yellow Oil |
| 199 | 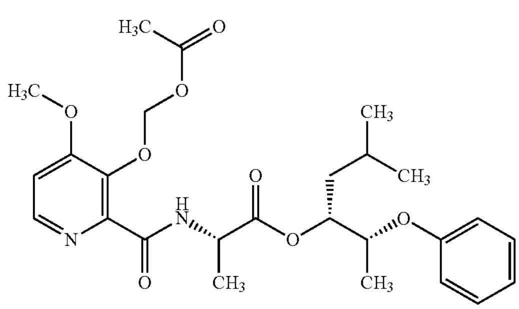 [SMILES: COc1ccnc(C(=O)N[C@@H](C)C(=O)O[C@H](CC(C)C)[C@@H](C)Oc2ccccc2)c1OCOC(C)=O] | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 200 | 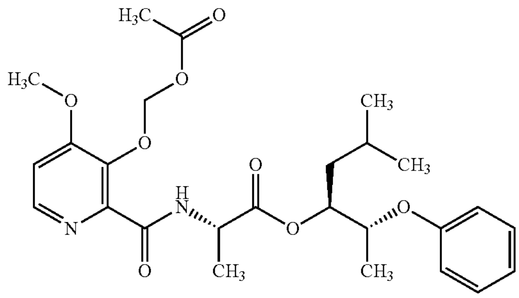 [SMILES: COc1ccnc(C(=O)N[C@@H](C)C(=O)O[C@@H](CC(C)C)[C@@H](C)Oc2ccccc2)c1OCOC(C)=O] | Example 14B. | Pale Yellow Oil |
| 201 | 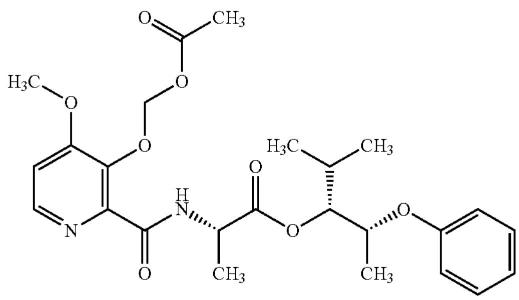 [SMILES: COc1ccnc(C(=O)N[C@@H](C)C(=O)O[C@H](C(C)C)[C@@H](C)Oc2ccccc2)c1OCOC(C)=O] | Example 14B. | Clear, Colorless Oil |
| 202 | 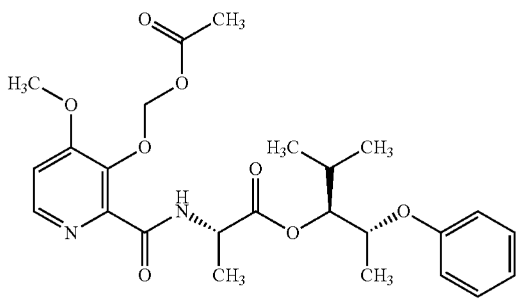 [SMILES: COc1ccnc(C(=O)N[C@@H](C)C(=O)O[C@@H](C(C)C)[C@@H](C)Oc2ccccc2)c1OCOC(C)=O] | Example 14B. | Clear, Colorless Oil |
| 203 | 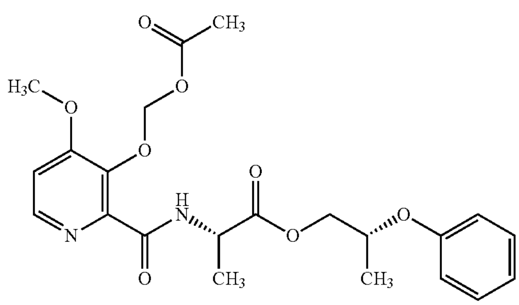 [SMILES: COc1ccnc(C(=O)N[C@@H](C)C(=O)OC[C@@H](C)Oc2ccccc2)c1OCOC(C)=O] | Example 14B. | Pale Yellow Oil |
| 204 | 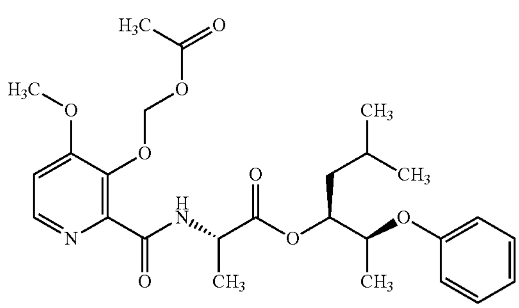 [SMILES: COc1ccnc(C(=O)N[C@@H](C)C(=O)O[C@@H](CC(C)C)[C@H](C)Oc2ccccc2)c1OCOC(C)=O] | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 205 | 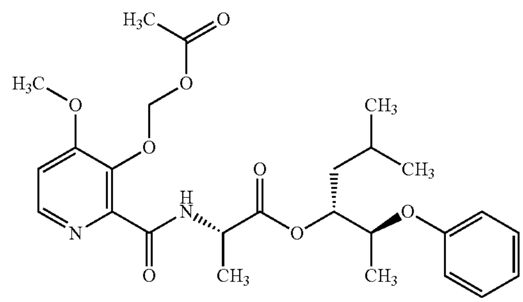 [SMILES: COc1ccnc(C(=O)N[C@@H](C)C(=O)O[C@H](CC(C)C)[C@H](C)Oc2ccccc2)c1OCOC(C)=O] | Example 14B. | Pale Yellow Oil |
| 206 | 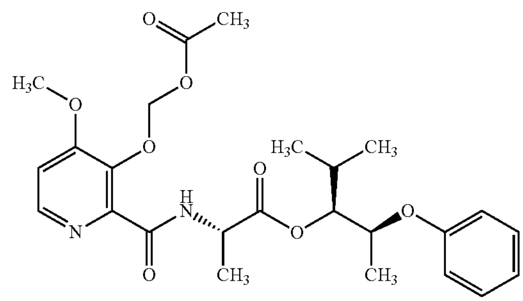 [SMILES: COc1ccnc(C(=O)N[C@@H](C)C(=O)O[C@@H](C(C)C)[C@H](C)Oc2ccccc2)c1OCOC(C)=O] | Example 14B. | Clear, Colorless Oil |
| 207 | 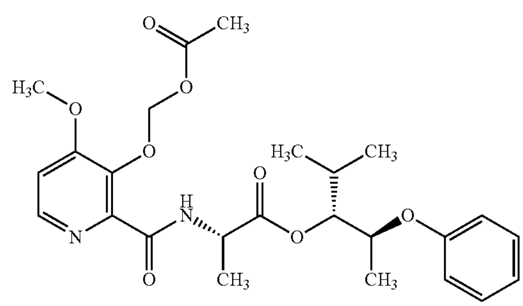 [SMILES: COc1ccnc(C(=O)N[C@@H](C)C(=O)O[C@H](C(C)C)[C@H](C)Oc2ccccc2)c1OCOC(C)=O] | Example 14B. | Clear, Colorless Oil |
| 208 | 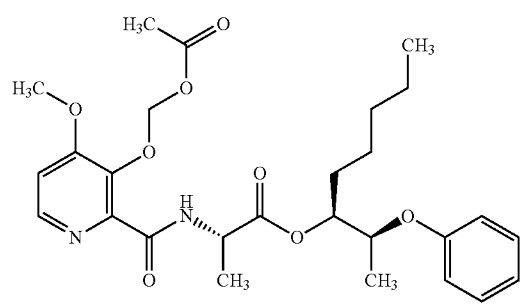 [SMILES: CCCCC[C@H](OC(=O)[C@H](C)NC(=O)c1nccc(OC)c1OCOC(C)=O)[C@H](C)Oc1ccccc1] | Example 14B. | Clear, Colorless Oil |
| 209 | 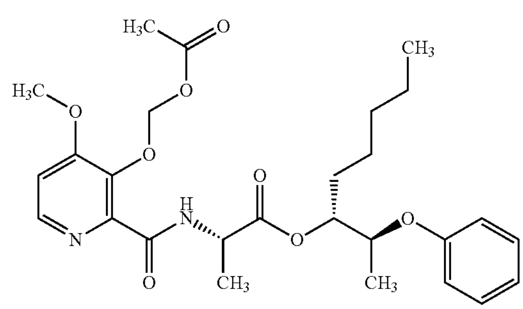 [SMILES: CCCCC[C@@H](OC(=O)[C@H](C)NC(=O)c1nccc(OC)c1OCOC(C)=O)[C@H](C)Oc1ccccc1] | Example 14B. | Clear, Colorless Oil |

TABLE 1-continued
Compound Structure, Preparation Method, and Appearance
| *Cmpd. No. | Structure | As Prepared According To | Appearance |
| --- | --- | --- | --- |
| 210 | 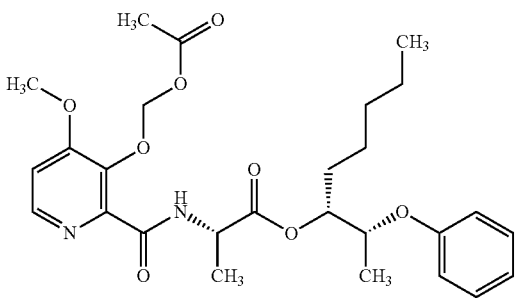 [SMILES: CCCCC[C@@H](OC(=O)[C@H](C)NC(=O)c1nccc(OC)c1OCOC(C)=O)[C@@H](C)Oc1ccccc1] | Example 14B. | Clear, Colorless Oil |
| 211 | 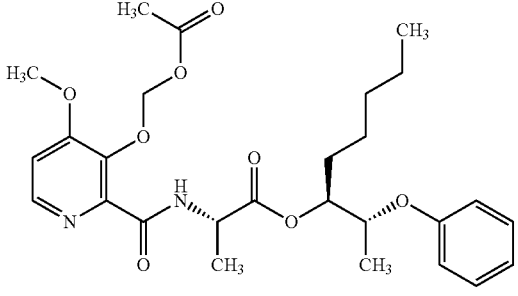 [SMILES: CCCCC[C@H](OC(=O)[C@H](C)NC(=O)c1nccc(OC)c1OCOC(C)=O)[C@@H](C)Oc1ccccc1] | Example 14B. | Clear, Colorless Oil |
| 212 | 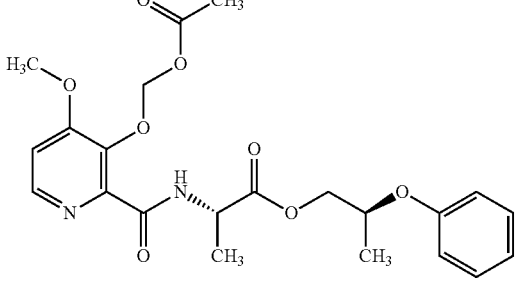 | Example 14B. | Clear, Colorless Oil |
| 213 | 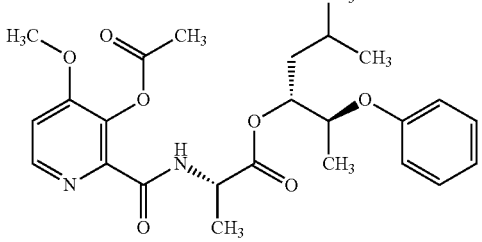 | Example 14A. | Clear, Colorless Oil |
| 214 | 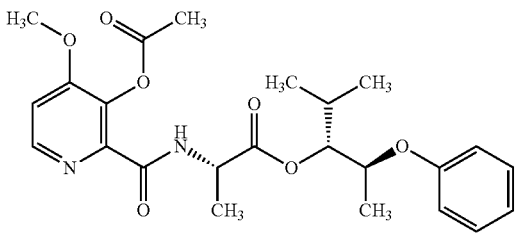 [SMILES: COc1ccnc(C(=O)N[C@@H](C)C(=O)O[C@H](C(C)C)[C@H](C)Oc2ccccc2)c1OC(C)=O] | Example 14A. | Clear, Colorless Oil |

TABLE 1-continued

Compound Structure, Preparation Method, and Appearance

| *Cmpd. No. | Structure | As Prepared According To | Appearance |
|---|---|---|---|
| 215 | 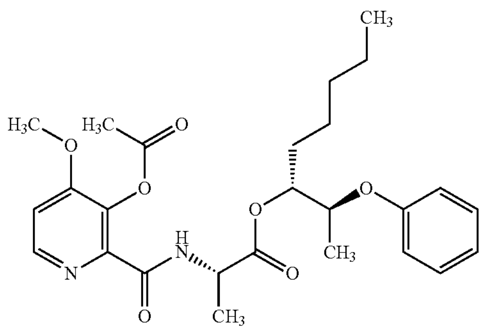 [SMILES: CCCCC[C@@H](OC(=O)[C@H](C)NC(=O)c1nccc(OC)c1OC(C)=O)[C@H](C)Oc1ccccc1] | Example 14A. | Clear, Colorless Oil |
| 216 | 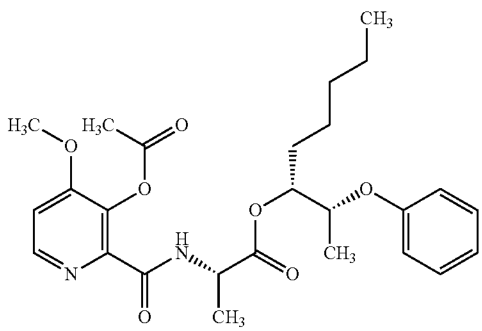 [SMILES: CCCCC[C@@H](OC(=O)[C@H](C)NC(=O)c1nccc(OC)c1OC(C)=O)[C@@H](C)Oc1ccccc1] | Example 14A. | Clear, Colorless Oil |
| 217 | 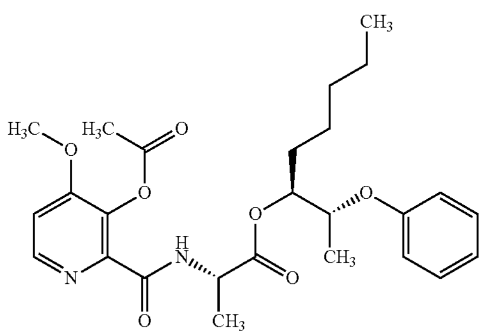 [SMILES: CCCCC[C@H](OC(=O)[C@H](C)NC(=O)c1nccc(OC)c1OC(C)=O)[C@@H](C)Oc1ccccc1] | Example 14A. | Clear, Colorless Oil |
| 218 | 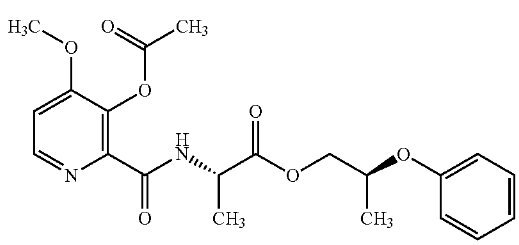 [SMILES: COc1ccnc(C(=O)N[C@@H](C)C(=O)OC[C@H](C)Oc2ccccc2)c1OC(C)=O] | Example 14A. | Clear, Colorless Oil |
| 219 | 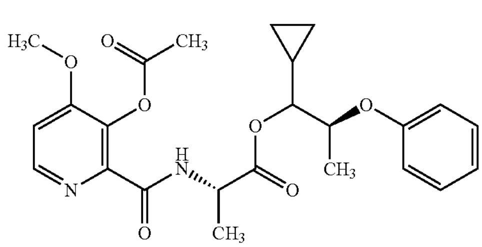 [SMILES: COc1ccnc(C(=O)N[C@@H](C)C(=O)OC(C2CC2)[C@H](C)Oc2ccccc2)c1OC(C)=O] | Example 14A. | Clear, Colorless Oil |

TABLE 1-continued

Compound Structure, Preparation Method, and Appearance

| *Cmpd. No. | Structure | As Prepared According To | Appearance |
|---|---|---|---|
| 220 | 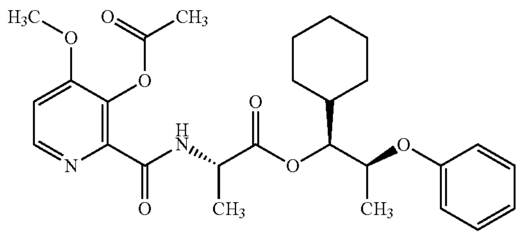 [SMILES: COc1ccnc(C(=O)N[C@@H](C)C(=O)O[C@@H](C2CCCCC2)[C@H](C)Oc2ccccc2)c1OC(C)=O] | Example 14A. | Clear, Colorless Oil |
| 221 | 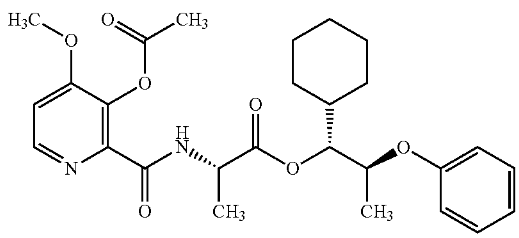 [SMILES: COc1ccnc(C(=O)N[C@@H](C)C(=O)O[C@H](C2CCCCC2)[C@H](C)Oc2ccccc2)c1OC(C)=O] | Example 14A. | Clear, Colorless Oil |
| 222 | 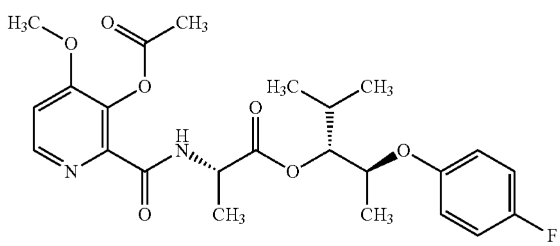 [SMILES: COc1ccnc(C(=O)N[C@@H](C)C(=O)O[C@H](C(C)C)[C@H](C)Oc2ccc(F)cc2)c1OC(C)=O] | Example 14A. | Clear, Colorless Oil |
| 223 | 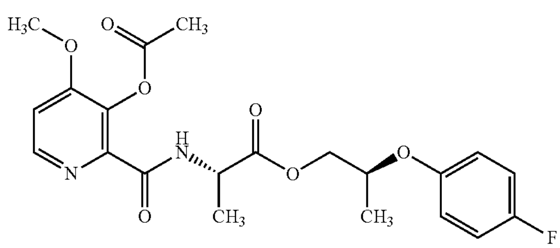 [SMILES: COc1ccnc(C(=O)N[C@@H](C)C(=O)OC[C@H](C)Oc2ccc(F)cc2)c1OC(C)=O] | Example 14A. | Clear, Colorless Oil |
| 224 | 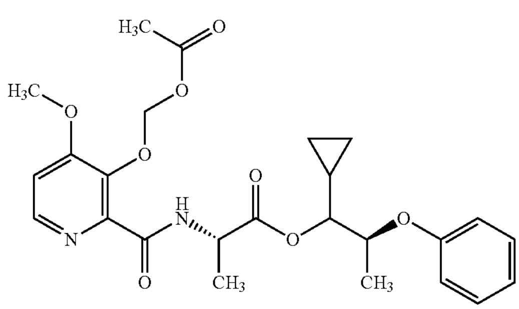 [SMILES: COc1ccnc(C(=O)N[C@@H](C)C(=O)OC(C2CC2)[C@H](C)Oc2ccccc2)c1OCOC(C)=O] | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 225 | 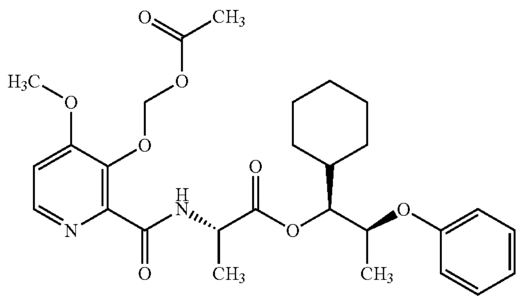 [SMILES: COc1ccnc(C(=O)N[C@@H](C)C(=O)O[C@@H](C2CCCCC2)[C@H](C)Oc2ccccc2)c1OCOC(C)=O] | Example 14B. | Clear, Colorless Oil |
| 226 | 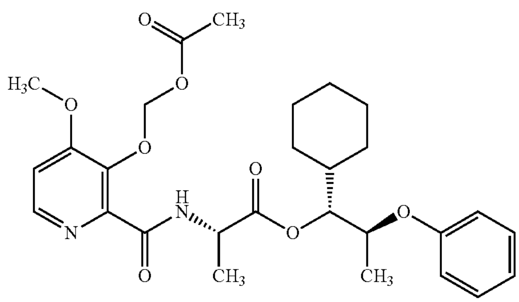 [SMILES: COc1ccnc(C(=O)N[C@@H](C)C(=O)O[C@H](C2CCCCC2)[C@H](C)Oc2ccccc2)c1OCOC(C)=O] | Example 14B. | Clear, Colorless Oil |
| 227 | 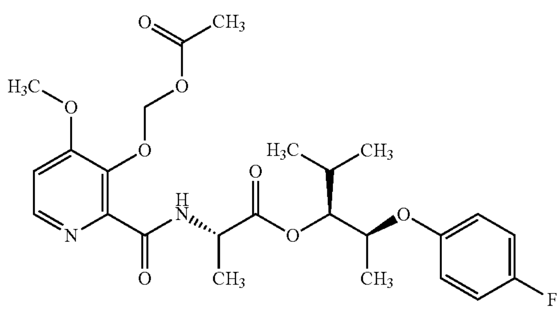 [SMILES: COc1ccnc(C(=O)N[C@@H](C)C(=O)O[C@@H](C(C)C)[C@H](C)Oc2ccc(F)cc2)c1OCOC(C)=O] | Example 14B. | Clear, Colorless Oil |
| 228 | 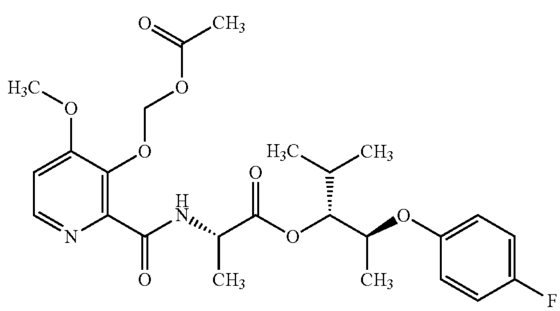 [SMILES: COc1ccnc(C(=O)N[C@@H](C)C(=O)O[C@H](C(C)C)[C@H](C)Oc2ccc(F)cc2)c1OCOC(C)=O] | Example 14B. | Clear, Colorless Oil |
| 229 | 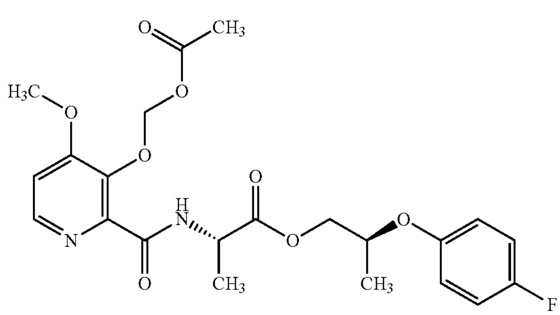 [SMILES: COc1ccnc(C(=O)N[C@@H](C)C(=O)OC[C@H](C)Oc2ccc(F)cc2)c1OCOC(C)=O] | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 230 | 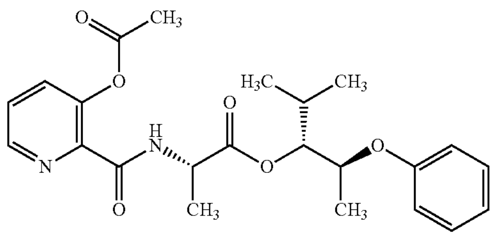 [SMILES: CC(=O)Oc1cccnc1C(=O)N[C@@H](C)C(=O)O[C@H](C(C)C)[C@H](C)Oc1ccccc1] | Example 14A. | Clear, Colorless Oil |
| 231 | 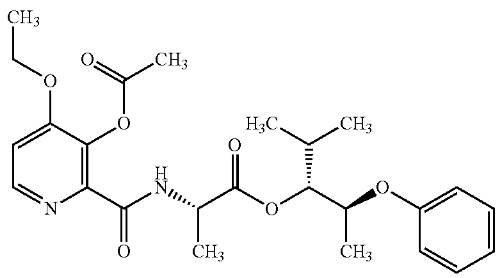 [SMILES: CCOc1ccnc(C(=O)N[C@@H](C)C(=O)O[C@H](C(C)C)[C@H](C)Oc2ccccc2)c1OC(C)=O] | Example 14A. | Clear, Colorless Oil |
| 233 | 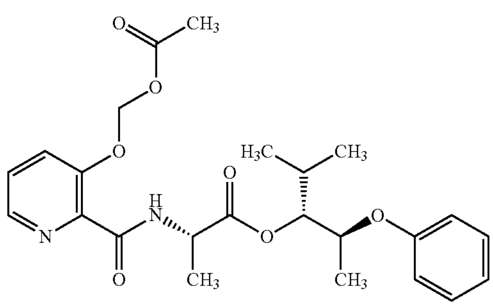 [SMILES: CC(=O)OCOc1cccnc1C(=O)N[C@@H](C)C(=O)O[C@H](C(C)C)[C@H](C)Oc1ccccc1] | Example 14B. | Clear, Colorless Oil |
| 234 | 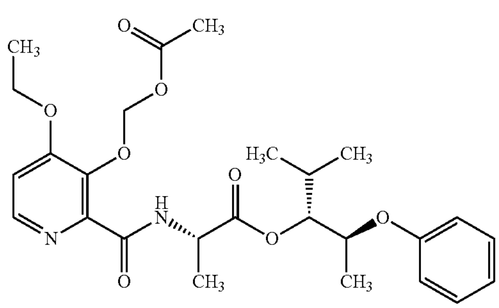 [SMILES: CCOc1ccnc(C(=O)N[C@@H](C)C(=O)O[C@H](C(C)C)[C@H](C)Oc2ccccc2)c1OCOC(C)=O] | Example 14B. | Clear, Colorless Oil |
| 236 | 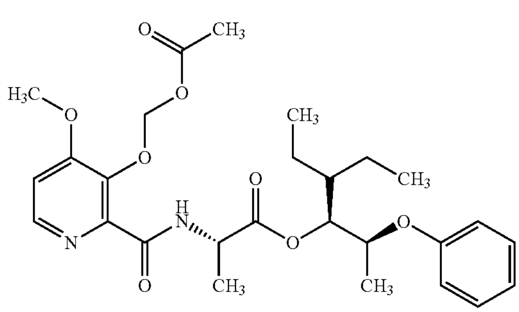 [SMILES: CCC(CC)[C@H](OC(=O)[C@H](C)NC(=O)c1nccc(OC)c1OCOC(C)=O)[C@H](C)Oc1ccccc1] | Example 14B. | Couldy Yellow Liquid |

TABLE 1-continued

Compound Structure, Preparation Method, and Appearance

| *Cmpd. No. | Structure | As Prepared According To | Appearance |
|---|---|---|---|
| 237 | 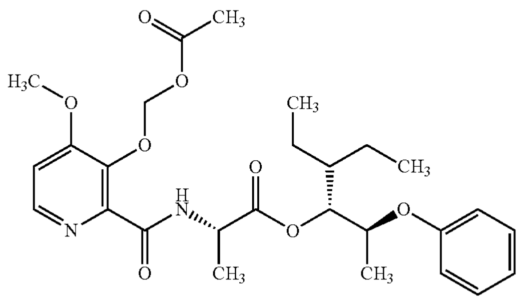 [SMILES: CCC(CC)[C@@H](OC(=O)[C@H](C)NC(=O)c1nccc(OC)c1OCOC(C)=O)[C@H](C)Oc1ccccc1] | Example 14B. | Cloudy Yellow Liquid |
| 238 | 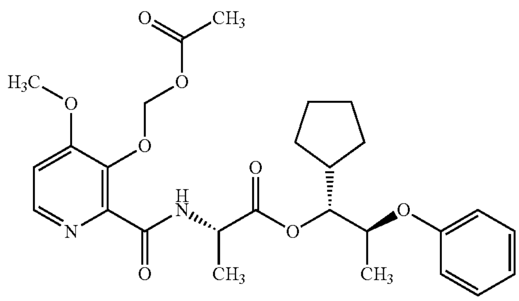 [SMILES: COc1ccnc(C(=O)N[C@@H](C)C(=O)O[C@H](C2CCCC2)[C@H](C)Oc2ccccc2)c1OCOC(C)=O] | Example 14B. | Yellow Liquid |
| 239 | 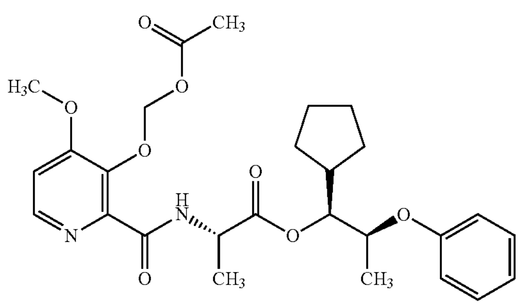 [SMILES: COc1ccnc(C(=O)N[C@@H](C)C(=O)O[C@@H](C2CCCC2)[C@H](C)Oc2ccccc2)c1OCOC(C)=O] | Example 14B. | Yellow Orange Liqiud |
| 240 | 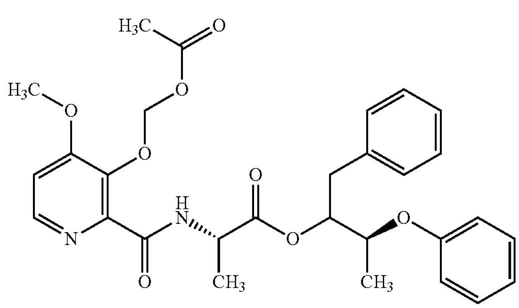 [SMILES: COc1ccnc(C(=O)N[C@@H](C)C(=O)OC(Cc2ccccc2)[C@H](C)Oc2ccccc2)c1OCOC(C)=O] | Example 14B. | Yellow Liquid |
| 241 | 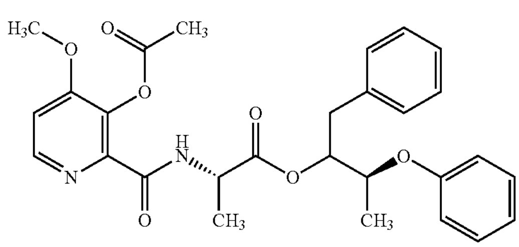 [SMILES: COc1ccnc(C(=O)N[C@@H](C)C(=O)OC(Cc2ccccc2)[C@H](C)Oc2ccccc2)c1OC(C)=O] | Example 14A. | Oil |

TABLE 1-continued
Compound Structure, Preparation Method, and Appearance
| *Cmpd. No. | Structure | As Prepared According To | Appearance |
|---|---|---|---|
| 242 | 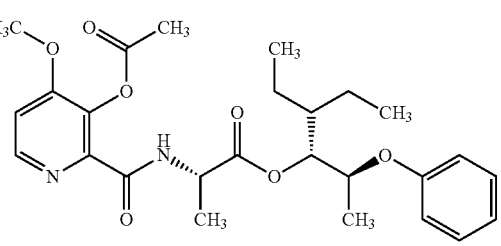 | Example 14A. | Oil |
| 243 | 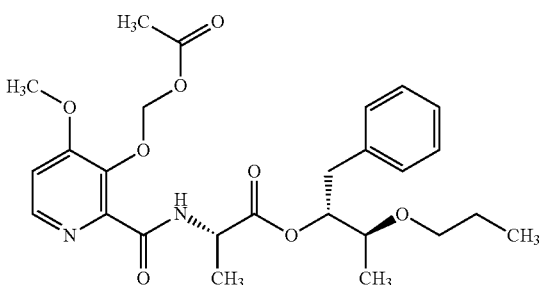 | Example 14B. | Thick Oil |
| 244 | 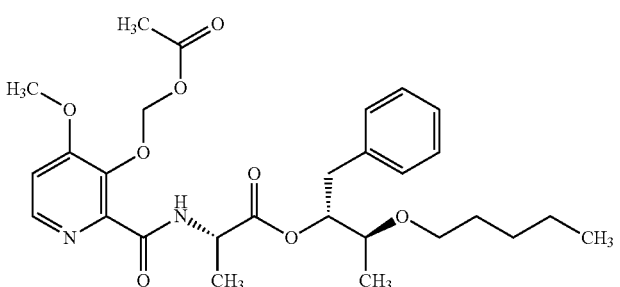 | Example 14B. | Thick Oil |
| 245 | 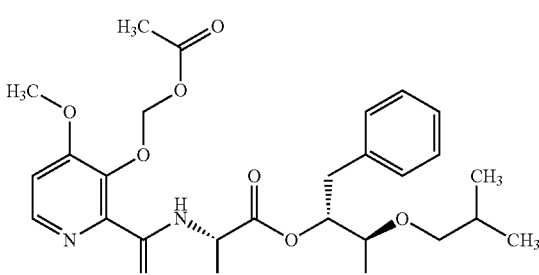 | Example 14B. | Thick Oil |
| 246 | 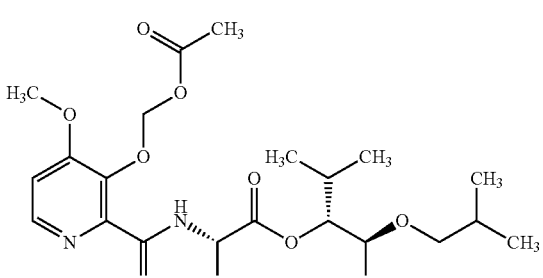 | Example 14B. | Thick Oil |

TABLE 1-continued

Compound Structure, Preparation Method, and Appearance

| *Cmpd. No. | Structure | As Prepared According To | Appearance |
|---|---|---|---|
| 247 | 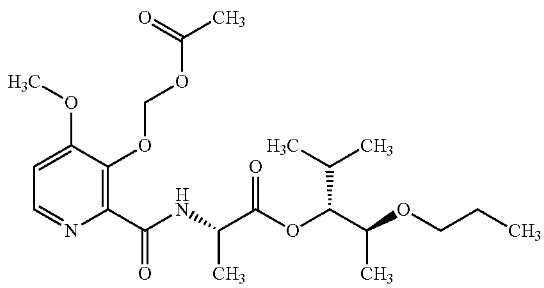 [SMILES: CCCO[C@@H](C)[C@H](OC(=O)[C@H](C)NC(=O)c1nccc(OC)c1OCOC(C)=O)C(C)C] | Example 14B. | Thick Oil |
| 248 | 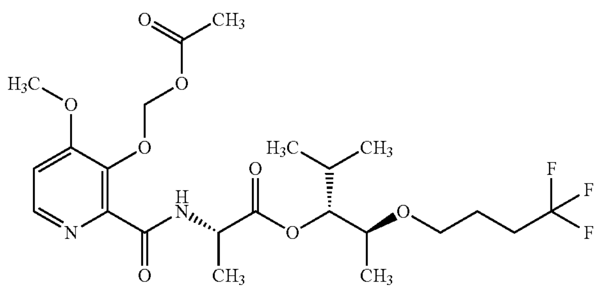 [SMILES: COc1ccnc(C(=O)N[C@@H](C)C(=O)O[C@H](C(C)C)[C@H](C)OCCCC(F)(F)F)c1OCOC(C)=O] | Example 14B. | Thick Oil |
| 249 | 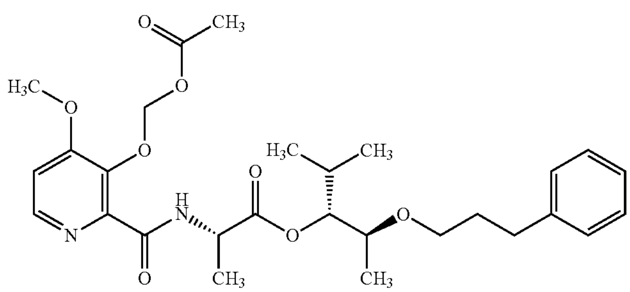 [SMILES: COc1ccnc(C(=O)N[C@@H](C)C(=O)O[C@H](C(C)C)[C@H](C)OCCCc2ccccc2)c1OCOC(C)=O] | Example 14B. | Thick Oil |
| 250 | 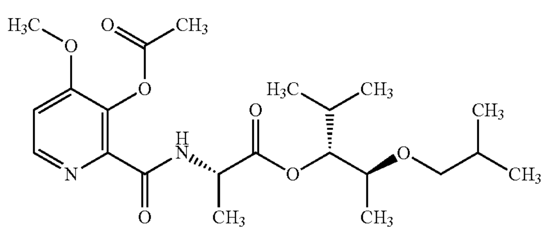 [SMILES: COc1ccnc(C(=O)N[C@@H](C)C(=O)O[C@H](C(C)C)[C@H](C)OCC(C)C)c1OC(C)=O] | Example 14A. | White Foam |
| 251 | 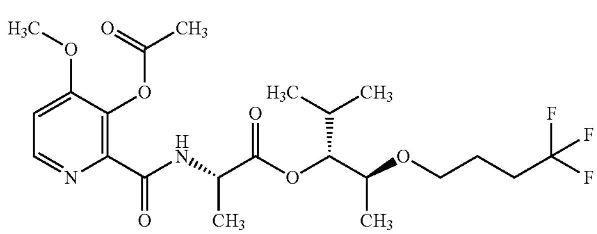 [SMILES: COc1ccnc(C(=O)N[C@@H](C)C(=O)O[C@H](C(C)C)[C@H](C)OCCCC(F)(F)F)c1OC(C)=O] | Example 14A. | Thick Oil |
| 252 | 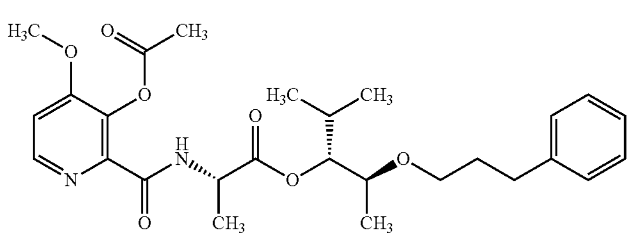 [SMILES: COc1ccnc(C(=O)N[C@@H](C)C(=O)O[C@H](C(C)C)[C@H](C)OCCCc2ccccc2)c1OC(C)=O] | Example 14A. | Thick Oil |

TABLE 1-continued

Compound Structure, Preparation Method, and Appearance

| *Cmpd. No. | Structure | As Prepared According To | Appearance |
|---|---|---|---|
| 253 | 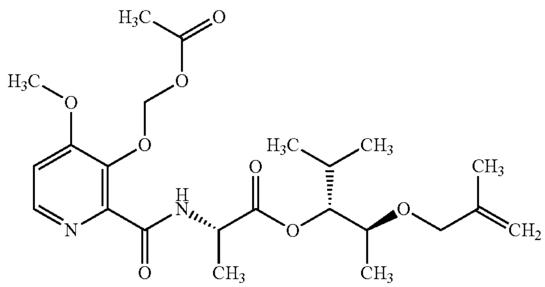 [SMILES: C=C(C)CO[C@@H](C)[C@H](OC(=O)[C@H](C)NC(=O)c1nccc(OC)c1OCOC(C)=O)C(C)C] | Example 14B. | Thick Oil |
| 254 | 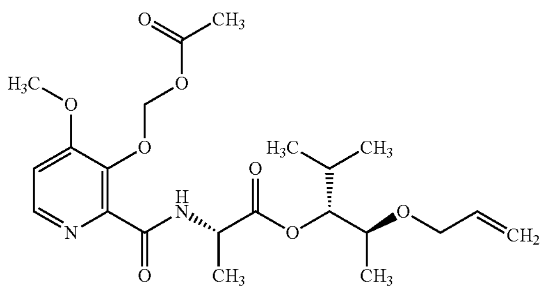 [SMILES: C=CCO[C@@H](C)[C@H](OC(=O)[C@H](C)NC(=O)c1nccc(OC)c1OCOC(C)=O)C(C)C] | Example 14B. | Thick Oil |
| 255 | 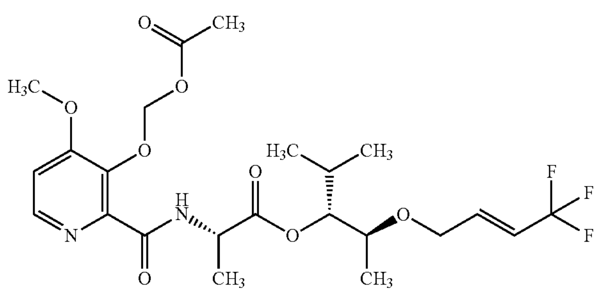 [SMILES: COc1ccnc(C(=O)N[C@@H](C)C(=O)O[C@H](C(C)C)[C@H](C)OC/C=C/C(F)(F)F)c1OCOC(C)=O] | Example 14B. | Thick Oil |
| 256 | 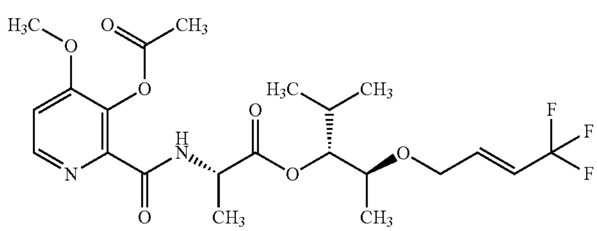 [SMILES: COc1ccnc(C(=O)N[C@@H](C)C(=O)O[C@H](C(C)C)[C@H](C)OC/C=C/C(F)(F)F)c1OC(C)=O] | Example 14A. | Thick Oil |
| 257 | 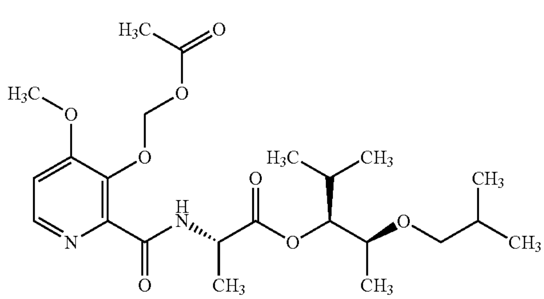 [SMILES: COc1ccnc(C(=O)N[C@@H](C)C(=O)O[C@@H](C(C)C)[C@H](C)OCC(C)C)c1OCOC(C)=O] | Example 14B. | Thick Oil |

TABLE 1-continued

Compound Structure, Preparation Method, and Appearance

| *Cmpd. No. | Structure | As Prepared According To | Appearance |
|---|---|---|---|
| 258 | 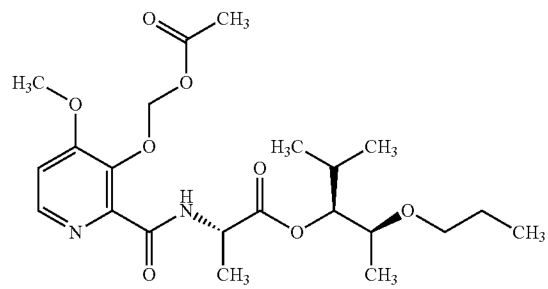 [SMILES: CCCO[C@@H](C)[C@@H](OC(=O)[C@H](C)NC(=O)c1nccc(OC)c1OCOC(C)=O)C(C)C] | Example 14B. | Thick Oil |
| 259 | 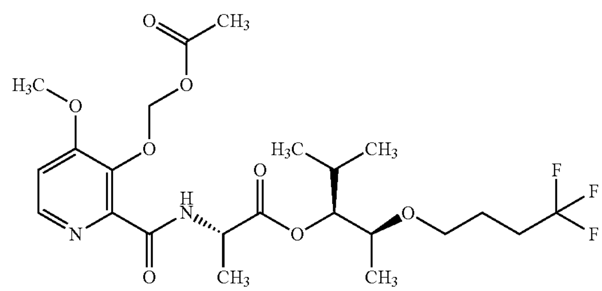 [SMILES: COc1ccnc(C(=O)N[C@@H](C)C(=O)O[C@@H](C(C)C)[C@H](C)OCCCC(F)(F)F)c1OCOC(C)=O] | Example 14B. | Thick Oil |
| 260 | 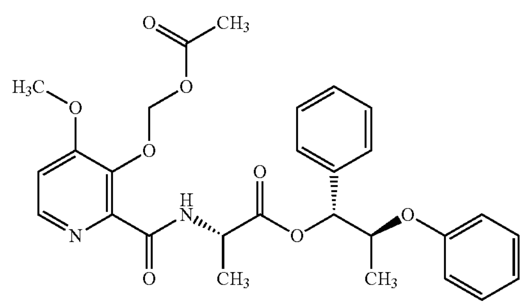 [SMILES: COc1ccnc(C(=O)N[C@@H](C)C(=O)O[C@H](c2ccccc2)[C@H](C)Oc2ccccc2)c1OCOC(C)=O] | Example 14B. | Clear, Colorless Oil |
| 261 | 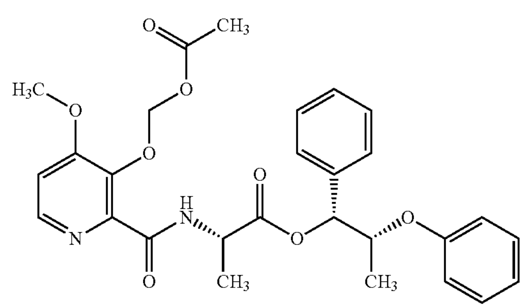 [SMILES: COc1ccnc(C(=O)N[C@@H](C)C(=O)O[C@H](c2ccccc2)[C@@H](C)Oc2ccccc2)c1OCOC(C)=O] | Example 14B. | Clear, Colorless Oil |
| 262 | 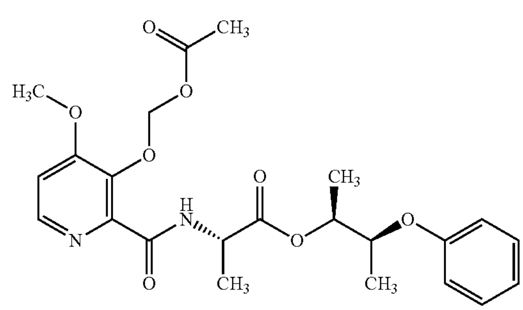 [SMILES: COc1ccnc(C(=O)N[C@@H](C)C(=O)O[C@@H](C)[C@H](C)Oc2ccccc2)c1OCOC(C)=O] | Example 14B. | Clear, Colorless Oil |

137
TABLE 1-continued
Compound Structure, Preparation Method, and Appearance
| *Cmpd. No. | Structure | As Prepared According To | Appearance |
|---|---|---|---|
| 263 | 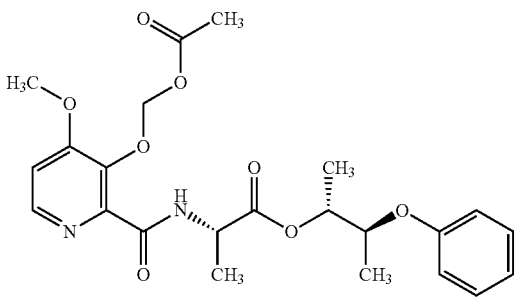 [SMILES: COc1ccnc(C(=O)N[C@@H](C)C(=O)O[C@H](C)[C@H](C)Oc2ccccc2)c1OCOC(C)=O] | Example 14B. | Clear, Colorless Oil |
| 264 | 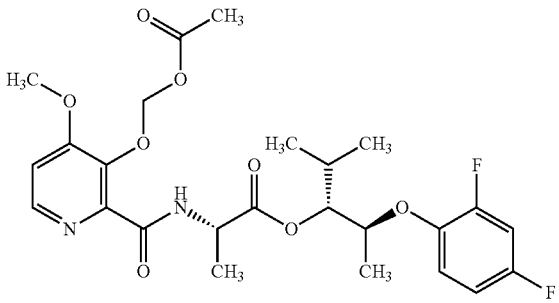 [SMILES: COc1ccnc(C(=O)N[C@@H](C)C(=O)O[C@H](C(C)C)[C@H](C)Oc2ccc(F)cc2F)c1OCOC(C)=O] | Example 14B. | Clear, Colorless Oil |
| 265 | 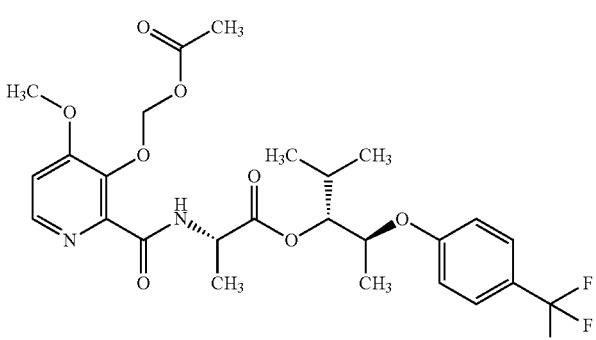 | Example 14B. | Clear, Colorless Oil |
| 266 | 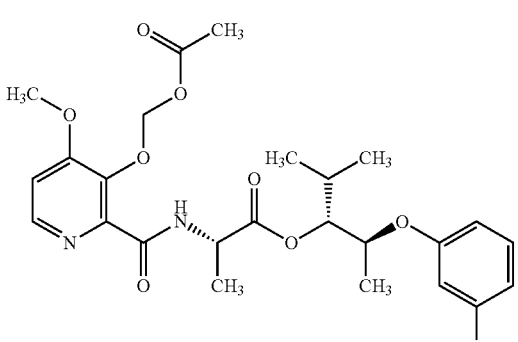 | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 267 | 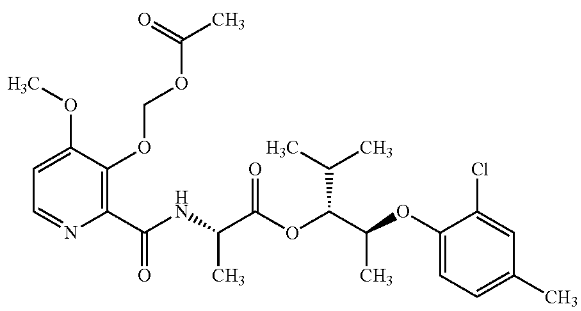 [SMILES: COc1ccnc(C(=O)N[C@@H](C)C(=O)O[C@H](C(C)C)[C@H](C)Oc2ccc(C)cc2Cl)c1OCOC(C)=O] | Example 14B. | Clear, Colorless Oil |
| 268 | 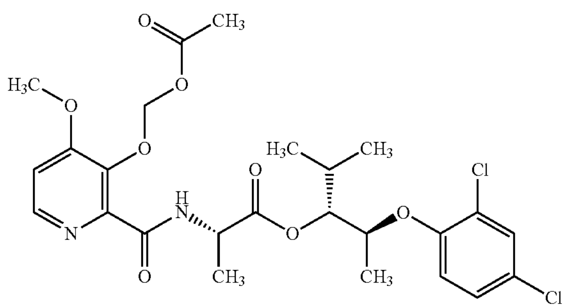 [SMILES: COc1ccnc(C(=O)N[C@@H](C)C(=O)O[C@H](C(C)C)[C@H](C)Oc2ccc(Cl)cc2Cl)c1OCOC(C)=O] | Example 14B. | Clear, Colorless Oil |
| 269 | 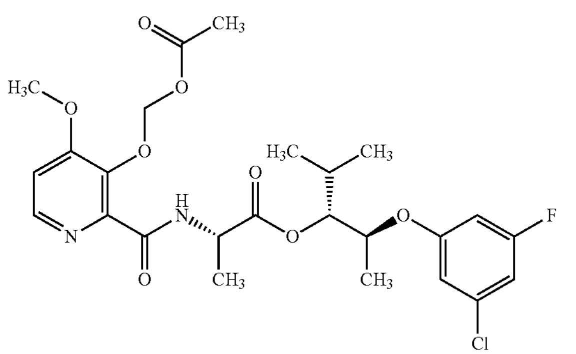 [SMILES: COc1ccnc(C(=O)N[C@@H](C)C(=O)O[C@H](C(C)C)[C@H](C)Oc2cc(F)cc(Cl)c2)c1OCOC(C)=O] | Example 14B. | Clear, Colorless Oil |
| 270 | 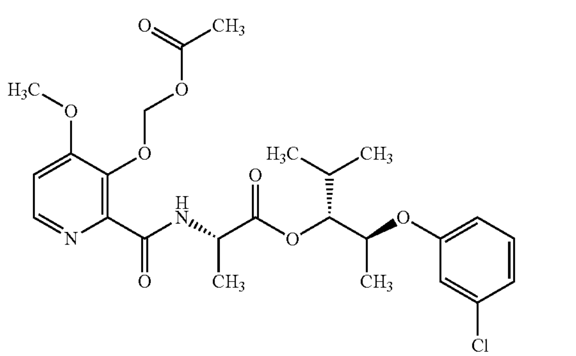 [SMILES: COc1ccnc(C(=O)N[C@@H](C)C(=O)O[C@H](C(C)C)[C@H](C)Oc2cccc(Cl)c2)c1OCOC(C)=O] | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 271 | 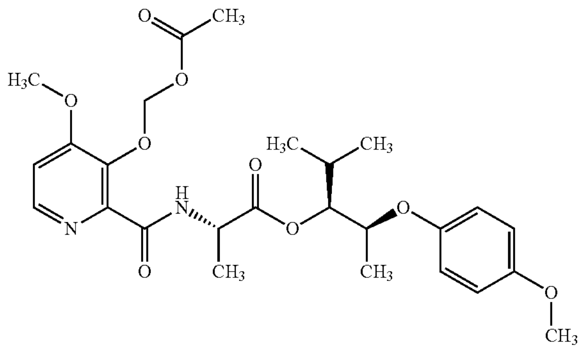 [SMILES: COc1ccc(O[C@@H](C)[C@@H](OC(=O)[C@H](C)NC(=O)c2nccc(OC)c2OCOC(C)=O)C(C)C)cc1] | Example 14B. | Clear, Colorless Oil |
| 272 | 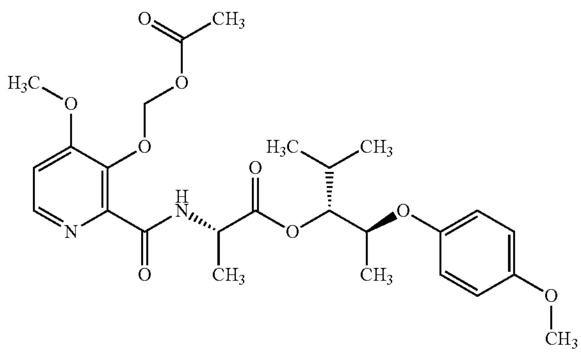 [SMILES: COc1ccc(O[C@@H](C)[C@H](OC(=O)[C@H](C)NC(=O)c2nccc(OC)c2OCOC(C)=O)C(C)C)cc1] | Example 14B. | Pale Yellow Oil |
| 273 | 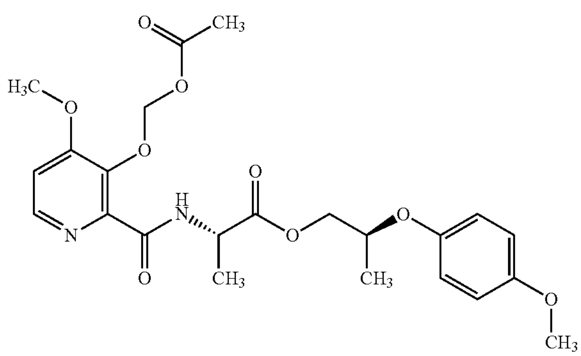 [SMILES: COc1ccc(O[C@@H](C)COC(=O)[C@H](C)NC(=O)c2nccc(OC)c2OCOC(C)=O)cc1] | Example 14B. | Pale Yellow Oil |
| 274 | 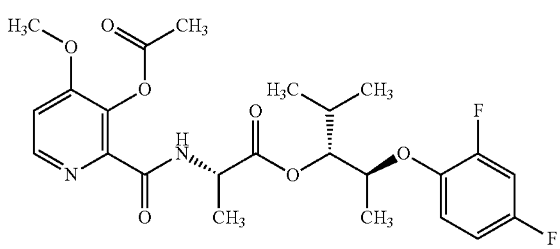 [SMILES: COc1ccnc(C(=O)N[C@@H](C)C(=O)O[C@H](C(C)C)[C@H](C)Oc2ccc(F)cc2F)c1OC(C)=O] | Example 14A. | Clear, Colorless Oil |

TABLE 1-continued

Compound Structure, Preparation Method, and Appearance

| *Cmpd. No. | Structure | As Prepared According To | Appearance |
|---|---|---|---|
| 275 | 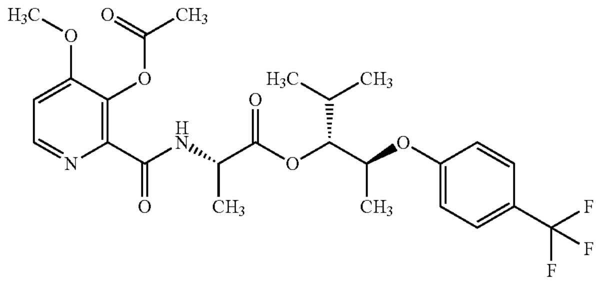 [SMILES: COc1ccnc(C(=O)N[C@@H](C)C(=O)O[C@H](C(C)C)[C@H](C)Oc2ccc(C(F)(F)F)cc2)c1OC(C)=O] | Example 14A. | Clear, Colorless Oil |
| 276 | 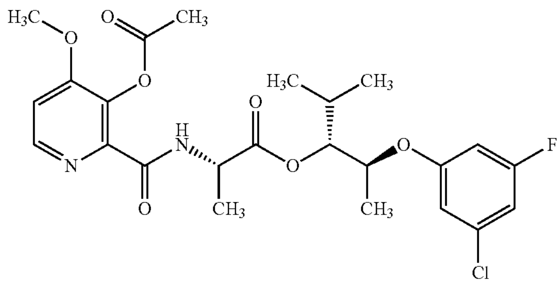 [SMILES: COc1ccnc(C(=O)N[C@@H](C)C(=O)O[C@H](C(C)C)[C@H](C)Oc2cc(F)cc(Cl)c2)c1OC(C)=O] | Example 14A. | Clear, Colorless Oil |
| 277 | 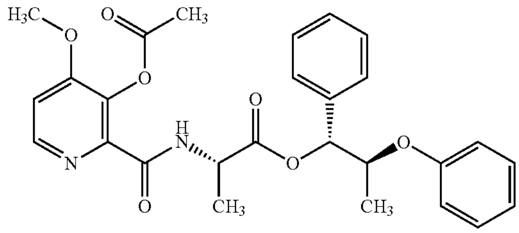 [SMILES: COc1ccnc(C(=O)N[C@@H](C)C(=O)O[C@H](c2ccccc2)[C@H](C)Oc2ccccc2)c1OC(C)=O] | Example 14A. | Clear, Colorless Oil |
| 278 | 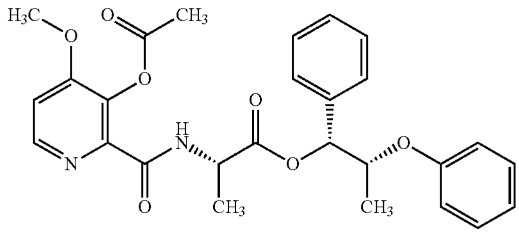 [SMILES: COc1ccnc(C(=O)N[C@@H](C)C(=O)O[C@H](c2ccccc2)[C@@H](C)Oc2ccccc2)c1OC(C)=O] | Example 14A. | Clear, Colorless Oil |
| 279 | 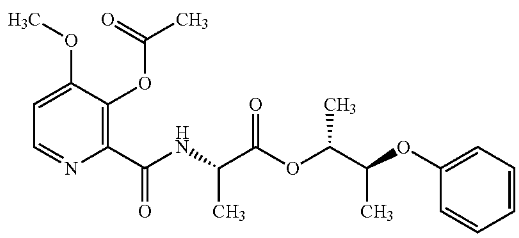 [SMILES: COc1ccnc(C(=O)N[C@@H](C)C(=O)O[C@H](C)[C@H](C)Oc2ccccc2)c1OC(C)=O] | Example 14A. | Clear, Colorless Oil |
| 280 | 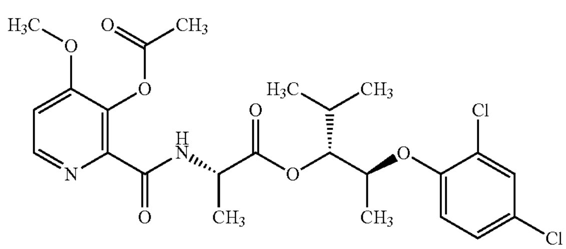 [SMILES: COc1ccnc(C(=O)N[C@@H](C)C(=O)O[C@H](C(C)C)[C@H](C)Oc2ccc(Cl)cc2Cl)c1OC(C)=O] | Example 14A. | Clear, Colorless Oil |

TABLE 1-continued

Compound Structure, Preparation Method, and Appearance

| *Cmpd. No. | Structure | As Prepared According To | Appearance |
|---|---|---|---|
| 281 | 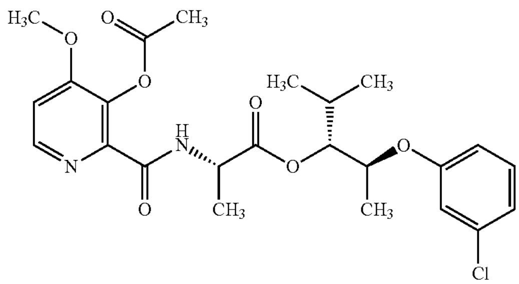 [SMILES: COc1ccnc(C(=O)N[C@@H](C)C(=O)O[C@H](C(C)C)[C@H](C)Oc2cccc(Cl)c2)c1OC(C)=O] | Example 14A. | Clear, Colorless Oil |
| 282 | 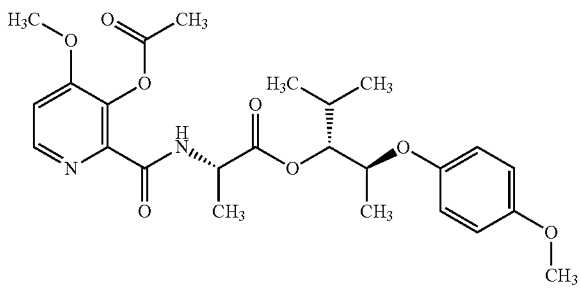 [SMILES: COc1ccc(O[C@@H](C)[C@H](OC(=O)[C@H](C)NC(=O)c2nccc(OC)c2OC(C)=O)C(C)C)cc1] | Example 14A. | Pale Yellow Oil |
| 283 | 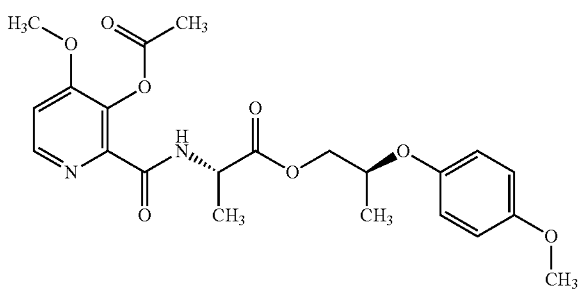 [SMILES: COc1ccc(O[C@@H](C)COC(=O)[C@H](C)NC(=O)c2nccc(OC)c2OC(C)=O)cc1] | Example 14A. | Clear, Colorless Oil |
| 285 | 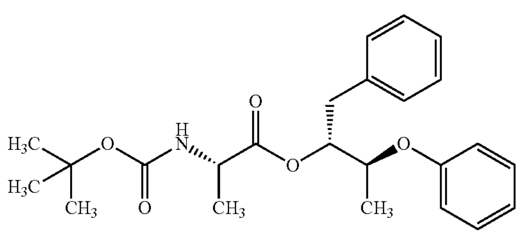 | Example 1D; Example 5C; Example 6A; Example 10A; Example 11. | Clear, Colorless Oil |
| 286 | 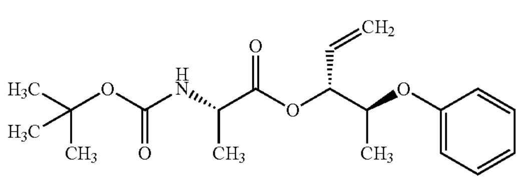 [SMILES: C=C[C@@H](OC(=O)[C@H](C)NC(=O)OC(C)(C)C)[C@H](C)Oc1ccccc1] | Example 1B; Example 2; Example 3B; Example 4B; Example 5B; Example 6A; Example 10A; Example 11. | Clear, Colorless Oil |
| 287 | 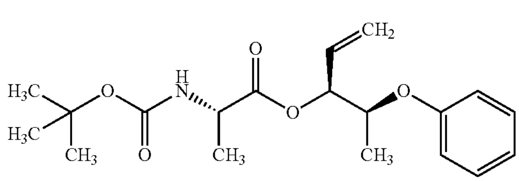 [SMILES: C=C[C@H](OC(=O)[C@H](C)NC(=O)OC(C)(C)C)[C@H](C)Oc1ccccc1] | Example 1B; Example 2; Example 3B; Example 4B; Example 5B; Example 6A; Example 10A; Example 11. | Clear, Colorless Oil |

TABLE 1-continued

Compound Structure, Preparation Method, and Appearance

| *Cmpd. No. | Structure | As Prepared According To | Appearance |
|---|---|---|---|
| 288 | 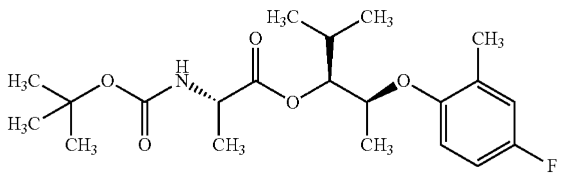 [SMILES: Cc1cc(F)ccc1O[C@@H](C)[C@@H](OC(=O)[C@H](C)NC(=O)OC(C)(C)C)C(C)C] | Example 1F, Steps 1-2; Example 3A; Example 11. | Clear, Colorless Oil |
| 289 | 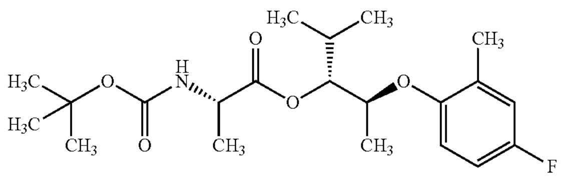 [SMILES: Cc1cc(F)ccc1O[C@@H](C)[C@H](OC(=O)[C@H](C)NC(=O)OC(C)(C)C)C(C)C] | Example 1F, Steps 1-2; Example 3A; Example 11. | Clear, Colorless Oil |
| 290 | 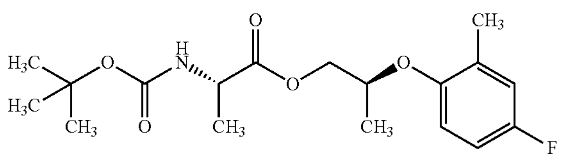 [SMILES: Cc1cc(F)ccc1O[C@@H](C)COC(=O)[C@H](C)NC(=O)OC(C)(C)C] | Example 1F, Steps 1-2; Example 3A; Example 11. | Clear, Colorless Oil |
| 291 | 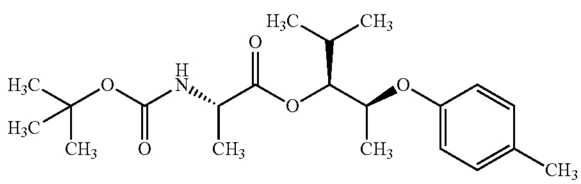 [SMILES: Cc1ccc(O[C@@H](C)[C@@H](OC(=O)[C@H](C)NC(=O)OC(C)(C)C)C(C)C)cc1] | Example 1F, Steps 1-2; Example 3A; Example 11. | Clear, Colorless Oil |
| 292 | 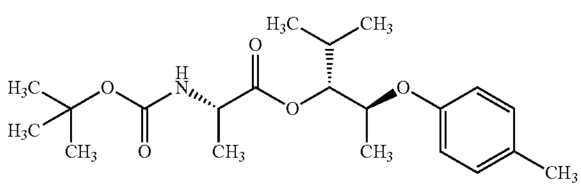 [SMILES: Cc1ccc(O[C@@H](C)[C@H](OC(=O)[C@H](C)NC(=O)OC(C)(C)C)C(C)C)cc1] | Example 1F, Steps 1-2; Example 3A; Example 11. | Clear, Colorless Oil |
| 293 | 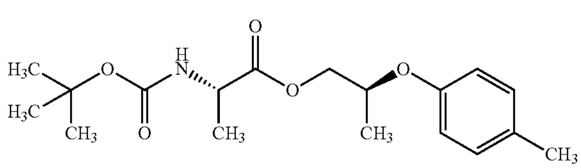 [SMILES: Cc1ccc(O[C@@H](C)COC(=O)[C@H](C)NC(=O)OC(C)(C)C)cc1] | Example 1F, Steps 1-2; Example 3A; Example 11. | Clear, Colorless Oil |
| 294 | 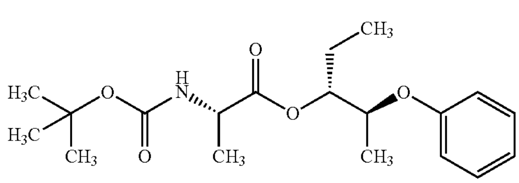 [SMILES: CC[C@@H](OC(=O)[C@H](C)NC(=O)OC(C)(C)C)[C@H](C)Oc1ccccc1] | Example 1B; Example 2; Example 3B; Example 4B; Example 5B; Example 6A; Example 10A; Example 11; Example 12B. | Clear, Colorless Oil |
| 295 | 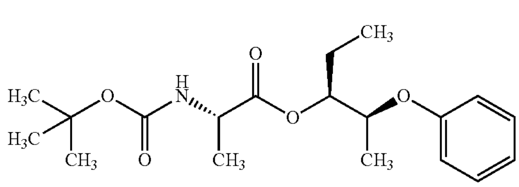 [SMILES: CC[C@H](OC(=O)[C@H](C)NC(=O)OC(C)(C)C)[C@H](C)Oc1ccccc1] | Example 1B; Example 2; Example 3B; Example 4B; Example 5B; Example 6A; Example 10A; Example 11; Example 12B. | Clear, Colorless Oil |

TABLE 1-continued

Compound Structure, Preparation Method, and Appearance

| *Cmpd. No. | Structure | As Prepared According To | Appearance |
|---|---|---|---|
| 296 | 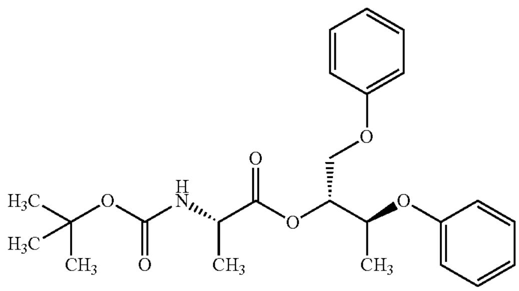 [SMILES: C[C@H](NC(=O)OC(C)(C)C)C(=O)O[C@H](COc1ccccc1)[C@H](C)Oc1ccccc1] | Example 1B; Example 2; Example 3B; Example 4B; Example 5B; Example 6A; Example 7; Example 8A; Example 10A; Example 11. | Clear, Colorless Oil |
| 297 | 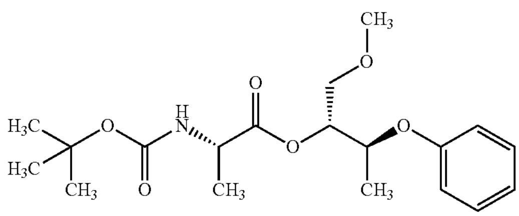 [SMILES: COC[C@@H](OC(=O)[C@H](C)NC(=O)OC(C)(C)C)[C@H](C)Oc1ccccc1] | Example 1B; Example 2; Example 3B; Example 4B; Example 5B; Example 6A; Example 7; Example 8B; Example 10A; Example 11. | Clear, Colorless Oil |
| 298 | 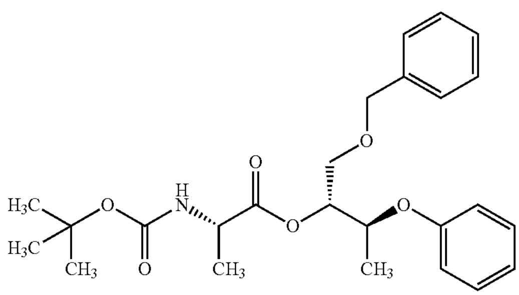 [SMILES: C[C@H](NC(=O)OC(C)(C)C)C(=O)O[C@H](COCc1ccccc1)[C@H](C)Oc1ccccc1] | Example 1B; Example 2; Example 3B; Example 4B; Example 5B; Example 6A; Example 7; Example 8C; Example 10A; Example 11. | Clear, Colorless Oil |
| 299 | 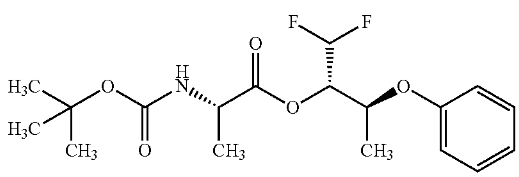 [SMILES: C[C@H](NC(=O)OC(C)(C)C)C(=O)O[C@H](C(F)F)[C@H](C)Oc1ccccc1] | Example 1B; Example 2; Example 3B; Example 4B; Example 5B; Example 6A; Example 9, Steps 1-2; Example 10A; Example 11. | Clear, Colorless Oil |
| 300 | 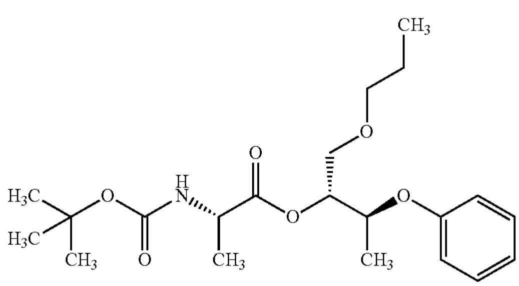 [SMILES: CCCOC[C@@H](OC(=O)[C@H](C)NC(=O)OC(C)(C)C)[C@H](C)Oc1ccccc1] | Example 1B; Example 2; Example 3B; Example 4B; Example 5B; Example 6A; Example 7; Example 8D; Example 10A; Example 11; Example 12B. | Clear, Colorless Oil |

TABLE 1-continued

Compound Structure, Preparation Method, and Appearance

| *Cmpd. No. | Structure | As Prepared According To | Appearance |
|---|---|---|---|
| 301 | 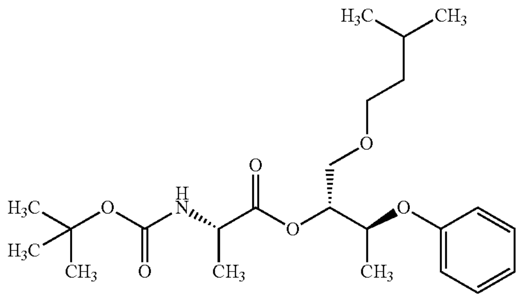 [SMILES: CC(C)CCOC[C@@H](OC(=O)[C@H](C)NC(=O)OC(C)(C)C)[C@H](C)Oc1ccccc1] | Example 1B; Example 2; Example 3B; Example 4B; Example 5B; Example 6A; Example 7; Example 8D; Example 10A; Example 11; Example 12B. | Clear, Colorless Oil |
| 302 | 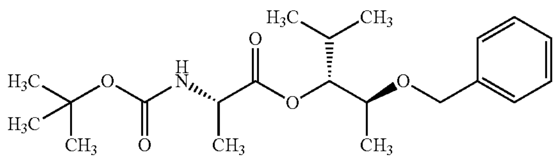 [SMILES: CC(C)[C@@H](OC(=O)[C@H](C)NC(=O)OC(C)(C)C)[C@H](C)OCc1ccccc1] | Example 1D; Example 3A; Example 4A; Example 5A; Example 6C; Example 10C; Example 11. | Colorless Oil |
| 303 | 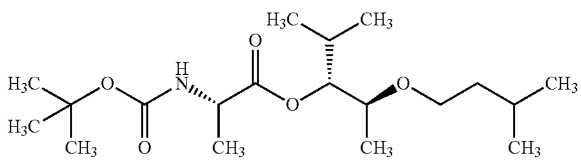 [SMILES: CC(C)CCO[C@@H](C)[C@H](OC(=O)[C@H](C)NC(=O)OC(C)(C)C)C(C)C] | Example 1D; Example 3A; Example 4A; Example 5A; Example 6C; Example 10C; Example 11. | Colorless Oil |
| 304 | 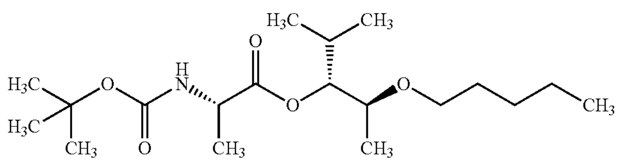 [SMILES: CCCCCO[C@@H](C)[C@H](OC(=O)[C@H](C)NC(=O)OC(C)(C)C)C(C)C] | Example 1D; Example 3A; Example 4A; Example 5A; Example 6C; Example 10C; Example 11. | Colorless Oil |
| 305 | 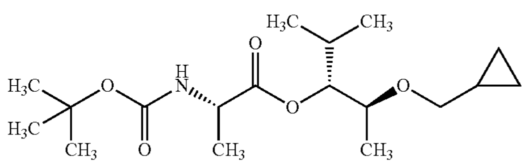 [SMILES: CC(C)[C@@H](OC(=O)[C@H](C)NC(=O)OC(C)(C)C)[C@H](C)OCC1CC1] | Example 1D; Example 3A; Example 4A; Example 5A; Example 6C; Example 10C; Example 11. | Colorless Oil |
| 306 | 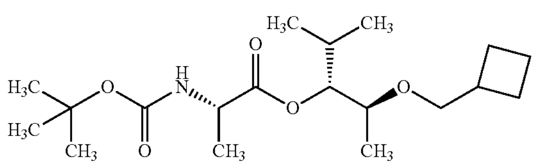 [SMILES: CC(C)[C@@H](OC(=O)[C@H](C)NC(=O)OC(C)(C)C)[C@H](C)OCC1CCC1] | Example 1D; Example 3A; Example 4A; Example 5A; Example 6C; Example 10C; Example 11. | Colorless Oil |
| 307 | 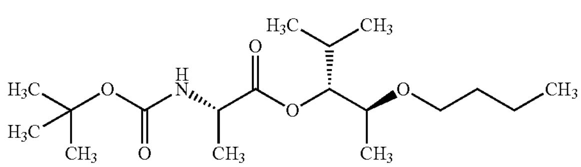 [SMILES: CCCCO[C@@H](C)[C@H](OC(=O)[C@H](C)NC(=O)OC(C)(C)C)C(C)C] | Example 1D; Example 3A; Example 4A; Example 5A; Example 6C; Example 10C; Example 11. | Colorless Oil |
| 308 | 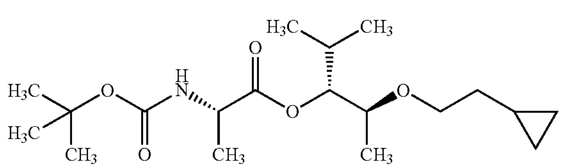 [SMILES: CC(C)[C@@H](OC(=O)[C@H](C)NC(=O)OC(C)(C)C)[C@H](C)OCCC1CC1] | Example 1D; Example 3A; Example 4A; Example 5A; Example 6C; Example 10C; Example 11. | Colorless Oil |

TABLE 1-continued

Compound Structure, Preparation Method, and Appearance

| *Cmpd. No. | Structure | As Prepared According To | Appearance |
|---|---|---|---|
| 309 | 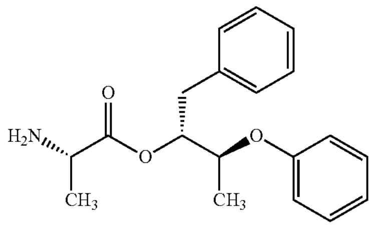 [SMILES: C[C@H](N)C(=O)O[C@H](Cc1ccccc1)[C@H](C)Oc1ccccc1] | Example 13A, Step 1. | Off White Semisolid |
| 310 | 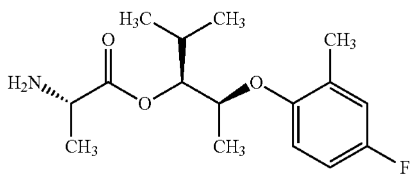 [SMILES: Cc1cc(F)ccc1O[C@@H](C)[C@@H](OC(=O)[C@H](C)N)C(C)C] | Example 13A, Step 1. | Clear, Colorless Oil |
| 311 | 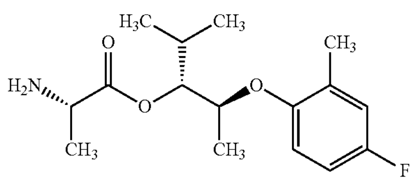 [SMILES: Cc1cc(F)ccc1O[C@@H](C)[C@H](OC(=O)[C@H](C)N)C(C)C] | Example 13A, Step 1. | White Semisolid |
| 312 | 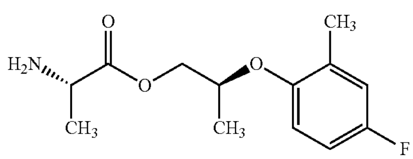 [SMILES: Cc1cc(F)ccc1O[C@@H](C)COC(=O)[C@H](C)N] | Example 13A, Step 1. | White Fluffy Semisolid |
| 313 | 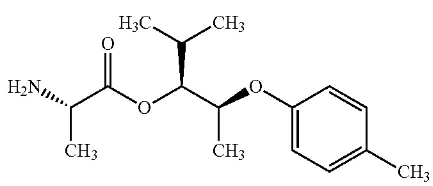 [SMILES: Cc1ccc(O[C@@H](C)[C@@H](OC(=O)[C@H](C)N)C(C)C)cc1] | Example 13A, Step 1. | White Semisolid |
| 314 | 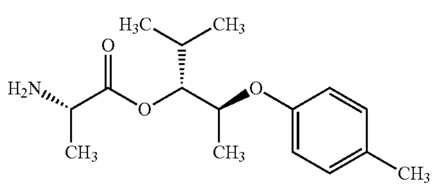 [SMILES: Cc1ccc(O[C@@H](C)[C@H](OC(=O)[C@H](C)N)C(C)C)cc1] | Example 13A, Step 1. | White Fluffy Semisolid |
| 315 | 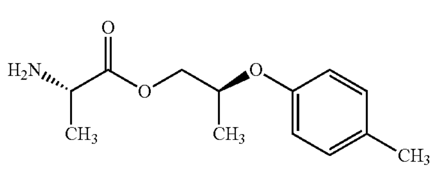 [SMILES: Cc1ccc(O[C@@H](C)COC(=O)[C@H](C)N)cc1] | Example 13A, Step 1. | White Semisolid |
| 316 | 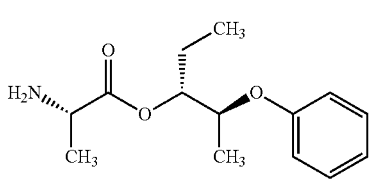 [SMILES: CC[C@@H](OC(=O)[C@H](C)N)[C@H](C)Oc1ccccc1] | Example 13A, Step 1. | Clear, Colorless Oil |

TABLE 1-continued

Compound Structure, Preparation Method, and Appearance

| *Cmpd. No. | Structure | As Prepared According To | Appearance |
|---|---|---|---|
| 317 | 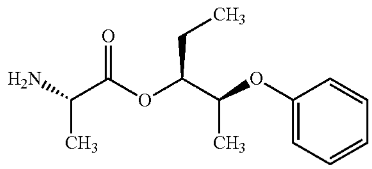 [SMILES: CC[C@H](OC(=O)[C@H](C)N)[C@H](C)Oc1ccccc1] | Example 13A, Step 1. | White Semisolid |
| 318 | 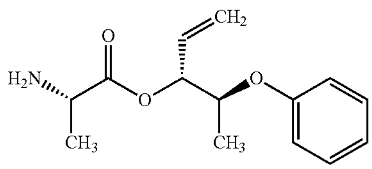 [SMILES: C=C[C@@H](OC(=O)[C@H](C)N)[C@H](C)Oc1ccccc1] | Example 13B, Step 1. | Pale Yellow Oil |
| 319 | 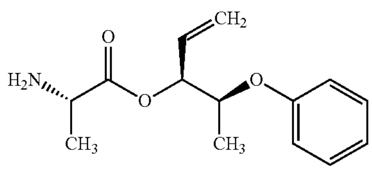 [SMILES: C=C[C@H](OC(=O)[C@H](C)N)[C@H](C)Oc1ccccc1] | Example 13B, Step 1. | Pale Yellow Oil |
| 320 | 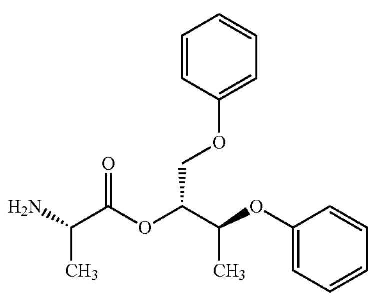 [SMILES: C[C@H](N)C(=O)O[C@H](COc1ccccc1)[C@H](C)Oc1ccccc1] | Example 13A, Step 1. | Clear, Colorless Oil |
| 321 | 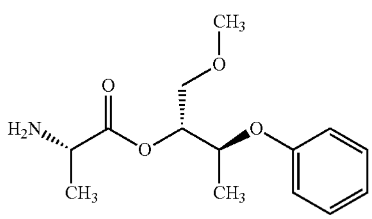 [SMILES: COC[C@@H](OC(=O)[C@H](C)N)[C@H](C)Oc1ccccc1] | Example 13A, Step 1. | White Semisolid |
| 322 | 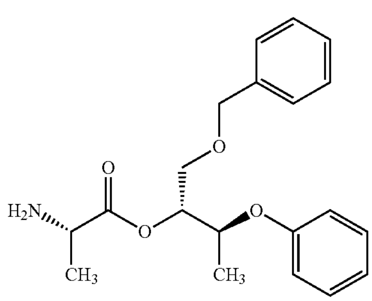 [SMILES: C[C@H](N)C(=O)O[C@H](COCc1ccccc1)[C@H](C)Oc1ccccc1] | Example 13A, Step 1. | Yellow Oil |
| 323 | 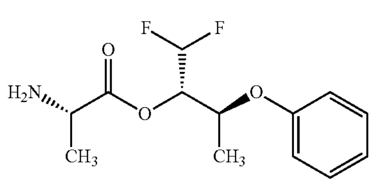 [SMILES: C[C@H](N)C(=O)O[C@H](C(F)F)[C@H](C)Oc1ccccc1] | Example 13A, Step 1. | White Semisolid |

TABLE 1-continued

Compound Structure, Preparation Method, and Appearance

| *Cmpd. No. | Structure | As Prepared According To | Appearance |
|---|---|---|---|
| 324 | 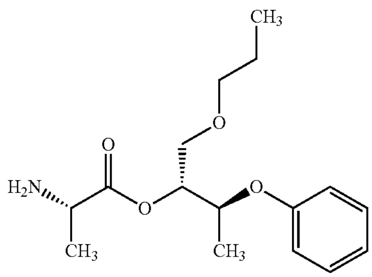 [SMILES: CCCOC[C@@H](OC(=O)[C@H](C)N)[C@H](C)Oc1ccccc1] | Example 13A, Step 1. | Clear, Colorless Oil |
| 325 | 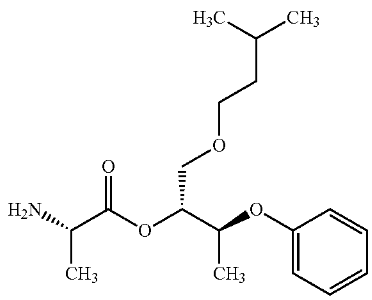 [SMILES: CC(C)CCOC[C@@H](OC(=O)[C@H](C)N)[C@H](C)Oc1ccccc1] | Example 13A, Step 1. | Clear, Colorless Oil |
| 326 | 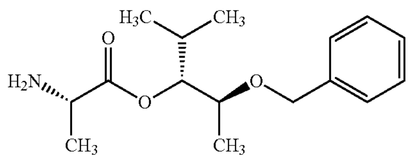 [SMILES: CC(C)[C@@H](OC(=O)[C@H](C)N)[C@H](C)OCc1ccccc1] | Example 13A, Step 1. | Thick Oil |
| 327 | 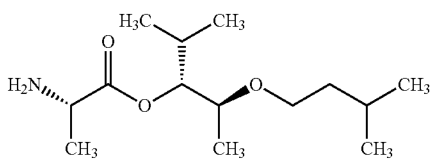 [SMILES: CC(C)CCO[C@@H](C)[C@H](OC(=O)[C@H](C)N)C(C)C] | Example 13A, Step 1. | Thick Oil |
| 328 | 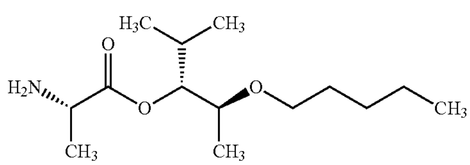 [SMILES: CCCCCO[C@@H](C)[C@H](OC(=O)[C@H](C)N)C(C)C] | Example 13A, Step 1. | Thick Oil |
| 329 | 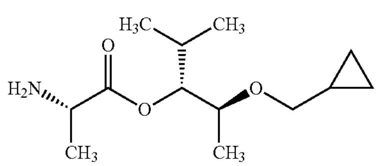 [SMILES: CC(C)[C@@H](OC(=O)[C@H](C)N)[C@H](C)OCC1CC1] | Example 13A, Step 1. | Thick Oil |
| 330 | 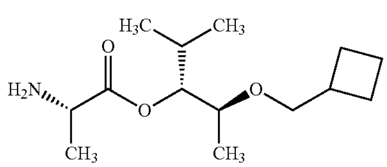 [SMILES: CC(C)[C@@H](OC(=O)[C@H](C)N)[C@H](C)OCC1CCC1] | Example 13A, Step 1. | Thick Oil |

TABLE 1-continued

Compound Structure, Preparation Method, and Appearance

| *Cmpd. No. | Structure | As Prepared According To | Appearance |
| --- | --- | --- | --- |
| 331 | 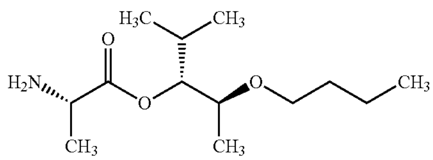 [SMILES: CCCCO[C@@H](C)[C@H](OC(=O)[C@H](C)N)C(C)C] | Example 13A, Step 1. | Thick Oil |
| 332 | 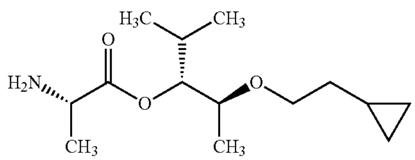 [SMILES: CC(C)[C@@H](OC(=O)[C@H](C)N)[C@H](C)OCCC1CC1] | Example 13A, Step 1. | Thick Oil |
| 333 | 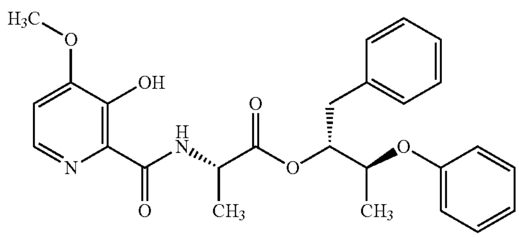 [SMILES: COc1ccnc(C(=O)N[C@@H](C)C(=O)O[C@H](Cc2ccccc2)[C@H](C)Oc2ccccc2)c1O] | Example 13A, Step 2. | Pale Yellow Oil |
| 334 | 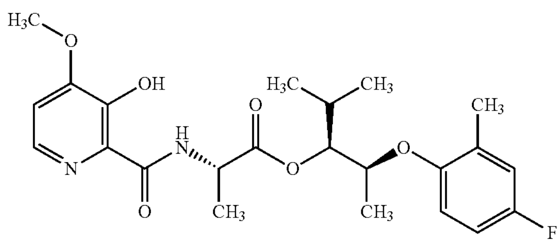 [SMILES: COc1ccnc(C(=O)N[C@@H](C)C(=O)O[C@@H](C(C)C)[C@H](C)Oc2ccc(F)cc2C)c1O] | Example 13A, Step 2. | Clear, Colorless Oil |
| 335 | 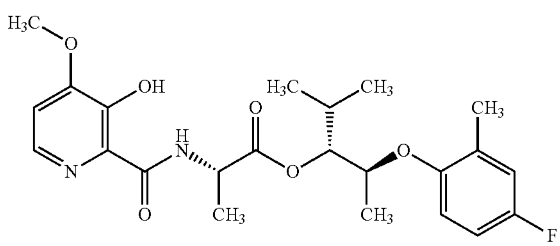 [SMILES: COc1ccnc(C(=O)N[C@@H](C)C(=O)O[C@H](C(C)C)[C@H](C)Oc2ccc(F)cc2C)c1O] | Example 13A, Step 2. | Clear, Colorless Oil |
| 336 | 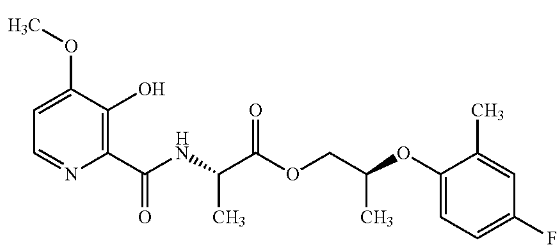 [SMILES: COc1ccnc(C(=O)N[C@@H](C)C(=O)OC[C@H](C)Oc2ccc(F)cc2C)c1O] | Example 13A, Step 2. | Clear, Colorless Oil |
| 337 | 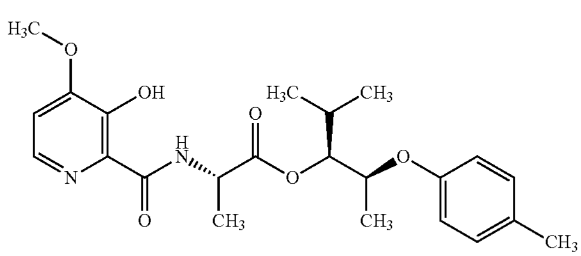 [SMILES: COc1ccnc(C(=O)N[C@@H](C)C(=O)O[C@@H](C(C)C)[C@H](C)Oc2ccc(C)cc2)c1O] | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 338 | 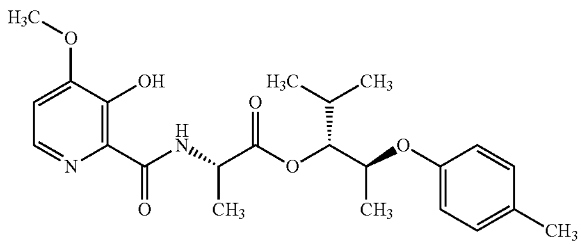 [SMILES: COc1ccnc(C(=O)N[C@@H](C)C(=O)O[C@H](C(C)C)[C@H](C)Oc2ccc(C)cc2)c1O] | Example 13A, Step 2. | Clear, Colorless Oil |
| 339 | 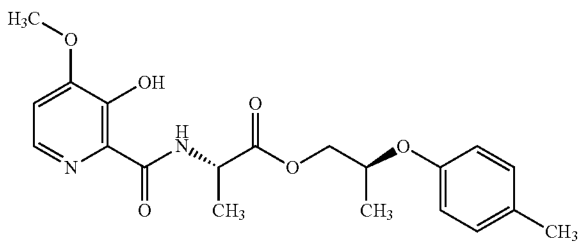 [SMILES: COc1ccnc(C(=O)N[C@@H](C)C(=O)OC[C@H](C)Oc2ccc(C)cc2)c1O] | Example 13A, Step 2. | Clear, Colorless Oil |
| 340 | 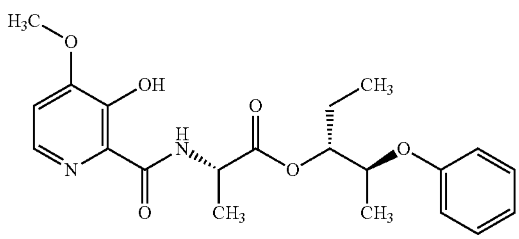 [SMILES: CC[C@@H](OC(=O)[C@H](C)NC(=O)c1nccc(OC)c1O)[C@H](C)Oc1ccccc1] | Example 13A, Step 2. | Clear, Colorless Oil |
| 341 | 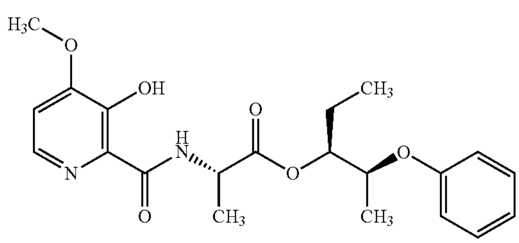 [SMILES: CC[C@H](OC(=O)[C@H](C)NC(=O)c1nccc(OC)c1O)[C@H](C)Oc1ccccc1] | Example 13A, Step 2. | Clear, Colorless Oil |
| 342 | 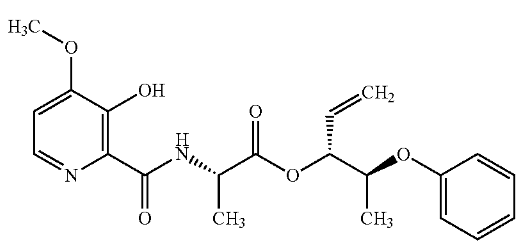 [SMILES: C=C[C@@H](OC(=O)[C@H](C)NC(=O)c1nccc(OC)c1O)[C@H](C)Oc1ccccc1] | Example 13B, Step 2. | Clear, Colorless Oil |
| 343 | 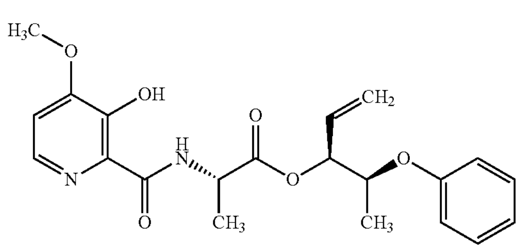 [SMILES: C=C[C@H](OC(=O)[C@H](C)NC(=O)c1nccc(OC)c1O)[C@H](C)Oc1ccccc1] | Example 13B, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 344 | 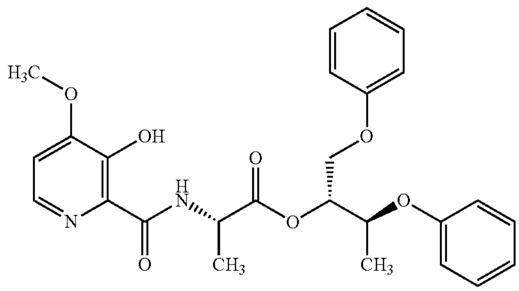 [SMILES: COc1ccnc(C(=O)N[C@@H](C)C(=O)O[C@H](COc2ccccc2)[C@H](C)Oc2ccccc2)c1O] | Example 13A, Step 2. | Clear, Colorless Oil |
| 345 | 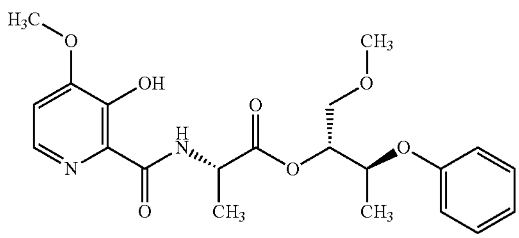 [SMILES: COC[C@@H](OC(=O)[C@H](C)NC(=O)c1nccc(OC)c1O)[C@H](C)Oc1ccccc1] | Example 13A, Step 2. | Clear, Colorless Oil |
| 346 | 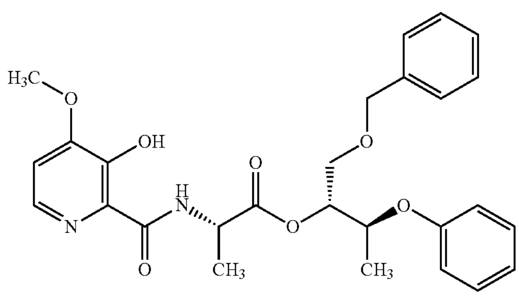 [SMILES: COc1ccnc(C(=O)N[C@@H](C)C(=O)O[C@H](COCc2ccccc2)[C@H](C)Oc2ccccc2)c1O] | Example 13A, Step 2. | Clear, Colorless Oil |
| 347 | 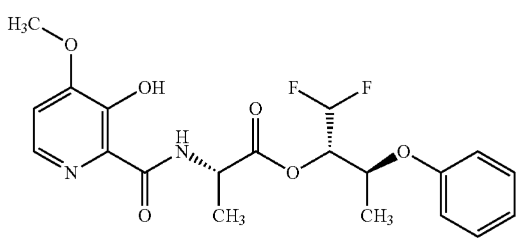 [SMILES: COc1ccnc(C(=O)N[C@@H](C)C(=O)O[C@H](C(F)F)[C@H](C)Oc2ccccc2)c1O] | Example 13A, Step 2. | White Semisolid |
| 348 | 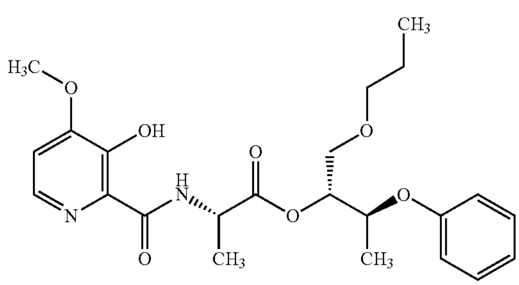 [SMILES: CCCOC[C@@H](OC(=O)[C@H](C)NC(=O)c1nccc(OC)c1O)[C@H](C)Oc1ccccc1] | Example 13A, Step 2. | Clear, Colorless Oil |

TABLE 1-continued

Compound Structure, Preparation Method, and Appearance

| *Cmpd. No. | Structure | As Prepared According To | Appearance |
|---|---|---|---|
| 349 | 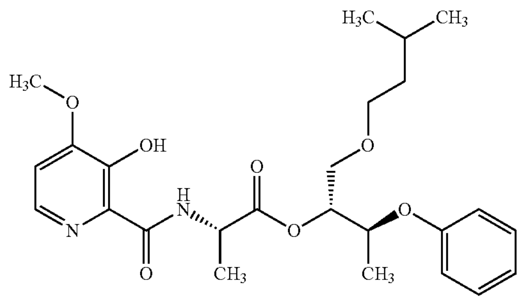 [SMILES: COc1ccnc(C(=O)N[C@@H](C)C(=O)O[C@H](COCCC(C)C)[C@H](C)Oc2ccccc2)c1O] | Example 13A, Step 2. | Clear, Colorless Oil |
| 350 | 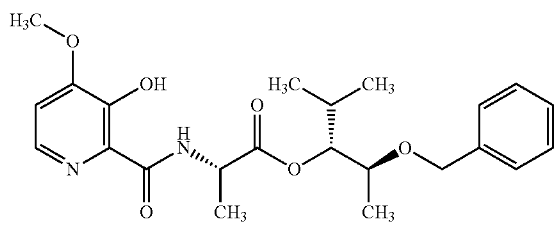 [SMILES: COc1ccnc(C(=O)N[C@@H](C)C(=O)O[C@H](C(C)C)[C@H](C)OCc2ccccc2)c1O] | Example 13A, Step 2. | Thick Oil |
| 351 | 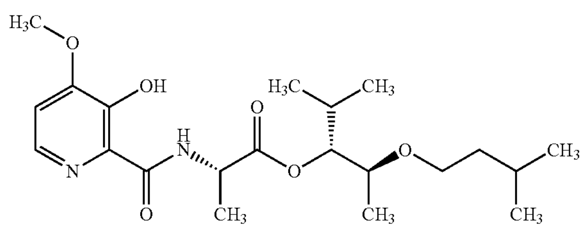 [SMILES: COc1ccnc(C(=O)N[C@@H](C)C(=O)O[C@H](C(C)C)[C@H](C)OCCC(C)C)c1O] | Example 13A, Step 2. | Thick Oil |
| 352 | 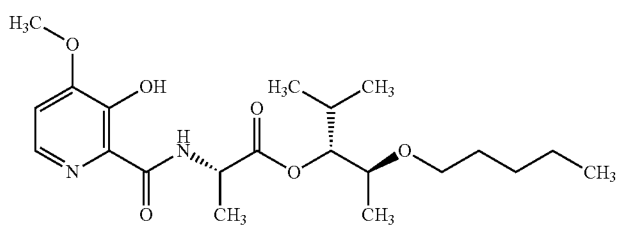 [SMILES: CCCCCO[C@@H](C)[C@H](OC(=O)[C@H](C)NC(=O)c1nccc(OC)c1O)C(C)C] | Example 13A, Step 2. | Thick Oil |
| 353 | 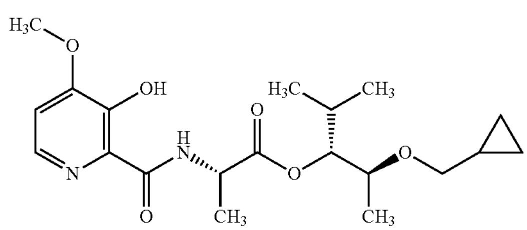 [SMILES: COc1ccnc(C(=O)N[C@@H](C)C(=O)O[C@H](C(C)C)[C@H](C)OCC2CC2)c1O] | Example 13A, Step 2. | Thick Oil |
| 354 | 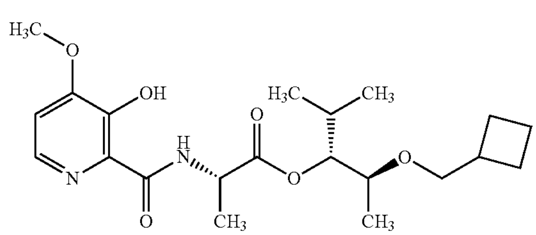 [SMILES: COc1ccnc(C(=O)N[C@@H](C)C(=O)O[C@H](C(C)C)[C@H](C)OCC2CCC2)c1O] | Example 13A, Step 2. | Thick Oil |

TABLE 1-continued

Compound Structure, Preparation Method, and Appearance

| *Cmpd. No. | Structure | As Prepared According To | Appearance |
|---|---|---|---|
| 355 | 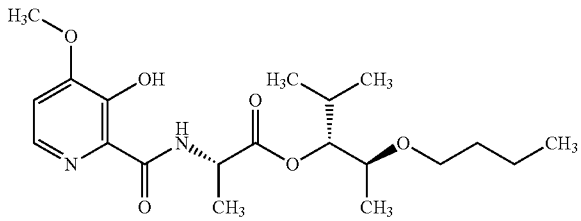 [SMILES: CCCCO[C@@H](C)[C@H](OC(=O)[C@H](C)NC(=O)c1nccc(OC)c1O)C(C)C] | Example 13A, Step 2. | Thick Oil |
| 356 | 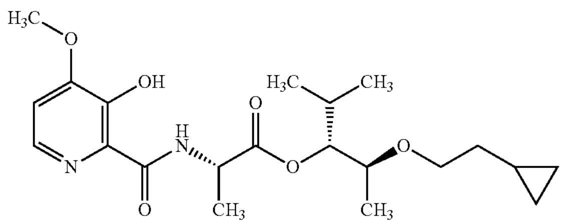 [SMILES: COc1ccnc(C(=O)N[C@@H](C)C(=O)O[C@H](C(C)C)[C@H](C)OCCC2CC2)c1O] | Example 13A, Step 2. | Thick Oil |
| 357 | 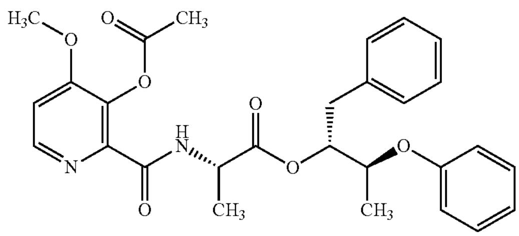 [SMILES: COc1ccnc(C(=O)N[C@@H](C)C(=O)O[C@H](Cc2ccccc2)[C@H](C)Oc2ccccc2)c1OC(C)=O] | Example 14A. | Clear, Colorless Oil |
| 358 | 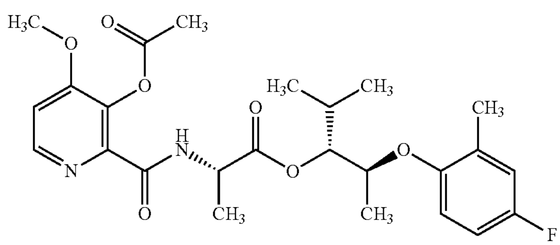 [SMILES: COc1ccnc(C(=O)N[C@@H](C)C(=O)O[C@H](C(C)C)[C@H](C)Oc2ccc(F)cc2C)c1OC(C)=O] | Example 14A. | Clear, Colorless Oil |
| 359 | 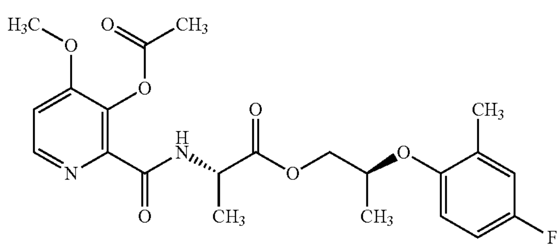 [SMILES: COc1ccnc(C(=O)N[C@@H](C)C(=O)OC[C@H](C)Oc2ccc(F)cc2C)c1OC(C)=O] | Example 14A. | Clear, Colorless Oil |
| 360 | 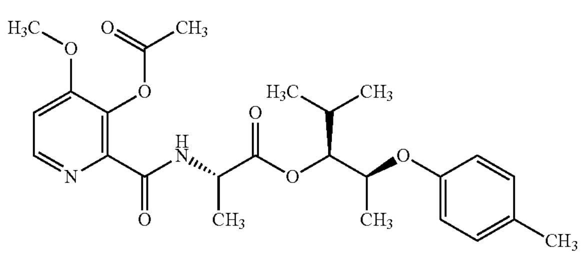 [SMILES: COc1ccnc(C(=O)N[C@@H](C)C(=O)O[C@@H](C(C)C)[C@H](C)Oc2ccc(C)cc2)c1OC(C)=O] | Example 14A. | Clear, Colorless Oil |

TABLE 1-continued

Compound Structure, Preparation Method, and Appearance

| *Cmpd. No. | Structure | As Prepared According To | Appearance |
|---|---|---|---|
| 361 | 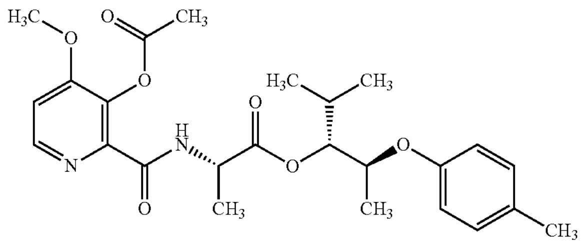 [SMILES: COc1ccnc(C(=O)N[C@@H](C)C(=O)O[C@H](C(C)C)[C@H](C)Oc2ccc(C)cc2)c1OC(C)=O] | Example 14A. | Pale Yellow Oil |
| 362 | 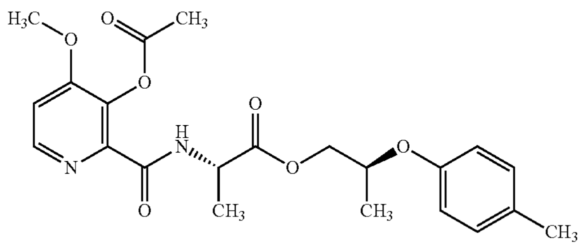 [SMILES: COc1ccnc(C(=O)N[C@@H](C)C(=O)OC[C@H](C)Oc2ccc(C)cc2)c1OC(C)=O] | Example 14A. | Pale Yellow Oil |
| 363 | 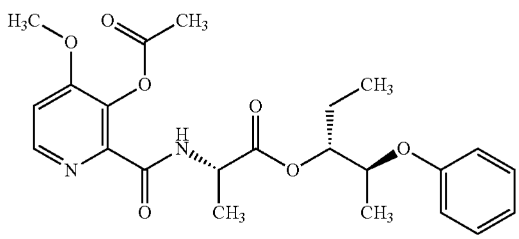 [SMILES: CC[C@@H](OC(=O)[C@H](C)NC(=O)c1nccc(OC)c1OC(C)=O)[C@H](C)Oc1ccccc1] | Example 14A. | Clear, Colorless Oil |
| 364 | 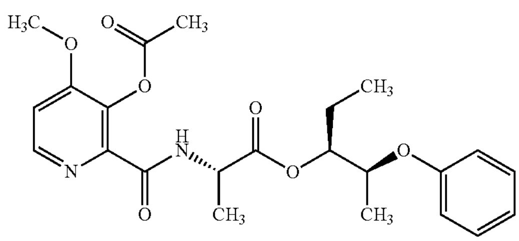 [SMILES: CC[C@H](OC(=O)[C@H](C)NC(=O)c1nccc(OC)c1OC(C)=O)[C@H](C)Oc1ccccc1] | Example 14A. | Clear, Colorless Oil |
| 365 | 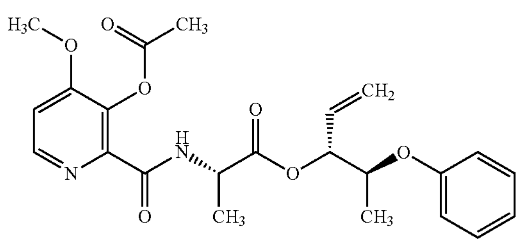 [SMILES: C=C[C@@H](OC(=O)[C@H](C)NC(=O)c1nccc(OC)c1OC(C)=O)[C@H](C)Oc1ccccc1] | Example 14A. | Clear, Colorless Oil |
| 366 | 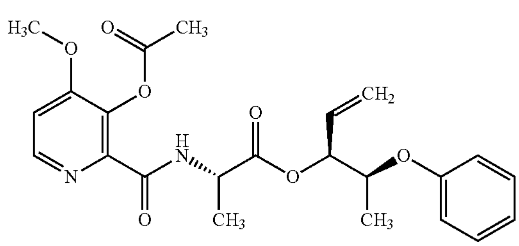 [SMILES: C=C[C@H](OC(=O)[C@H](C)NC(=O)c1nccc(OC)c1OC(C)=O)[C@H](C)Oc1ccccc1] | Example 14A. | Clear, Colorless Oil |

TABLE 1-continued

Compound Structure, Preparation Method, and Appearance

| *Cmpd. No. | Structure | As Prepared According To | Appearance |
|---|---|---|---|
| 367 | 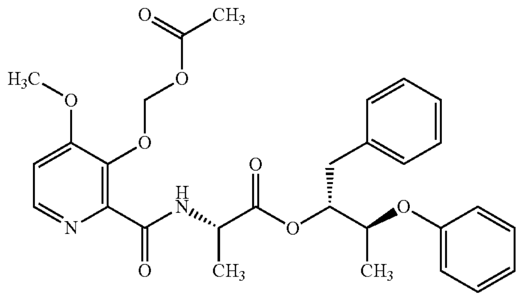 [SMILES: COc1ccnc(C(=O)N[C@@H](C)C(=O)O[C@H](Cc2ccccc2)[C@H](C)Oc2ccccc2)c1OCOC(C)=O] | Example 14B. | Pale Yellow Oil |
| 368 | 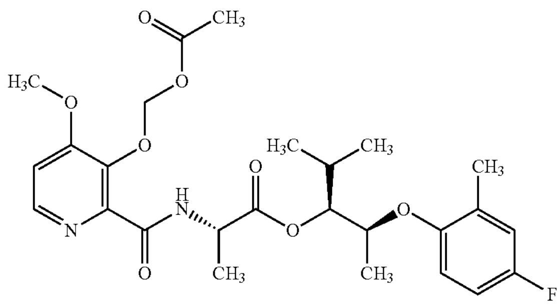 [SMILES: COc1ccnc(C(=O)N[C@@H](C)C(=O)O[C@@H](C(C)C)[C@H](C)Oc2ccc(F)cc2C)c1OCOC(C)=O] | Example 14B. | Clear, Colorless Oil |
| 369 | 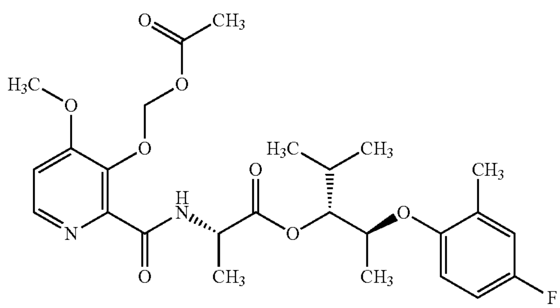 [SMILES: COc1ccnc(C(=O)N[C@@H](C)C(=O)O[C@H](C(C)C)[C@H](C)Oc2ccc(F)cc2C)c1OCOC(C)=O] | Example 14B. | Clear, Colorless Oil |
| 370 | 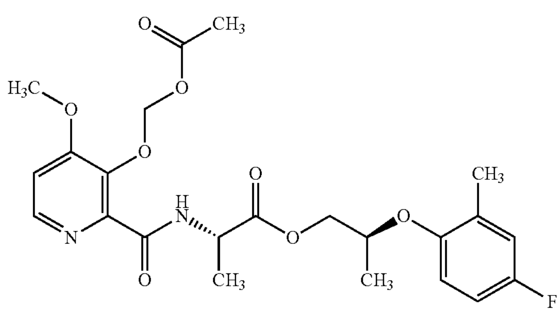 [SMILES: COc1ccnc(C(=O)N[C@@H](C)C(=O)OC[C@H](C)Oc2ccc(F)cc2C)c1OCOC(C)=O] | Example 14B. | Pale Yellow Oil |
| 371 | 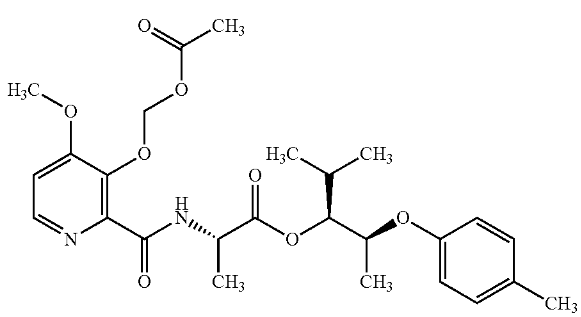 [SMILES: COc1ccnc(C(=O)N[C@@H](C)C(=O)O[C@@H](C(C)C)[C@H](C)Oc2ccc(C)cc2)c1OCOC(C)=O] | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 372 | 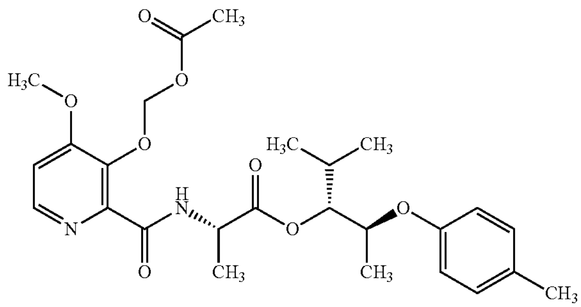 | Example 14B. | Pale Yellow Oil |
| 373 | 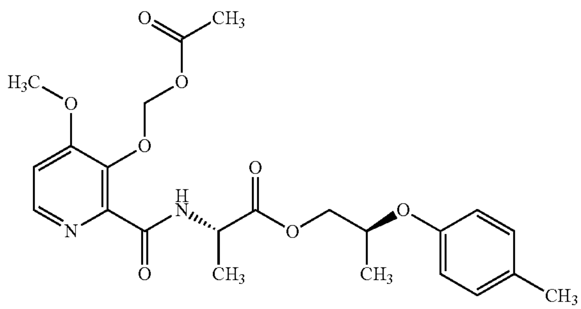 [SMILES: COc1ccnc(C(=O)N[C@@H](C)C(=O)OC[C@H](C)Oc2ccc(C)cc2)c1OCOC(C)=O] | Example 14B. | Pale Yellow Oil |
| 374 | 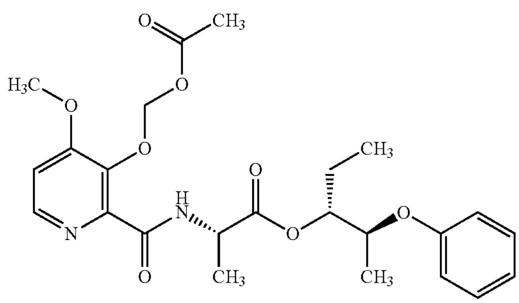 [SMILES: CC[C@@H](OC(=O)[C@H](C)NC(=O)c1nccc(OC)c1OCOC(C)=O)[C@H](C)Oc1ccccc1] | Example 14B. | Pale Yellow Oil |
| 375 | 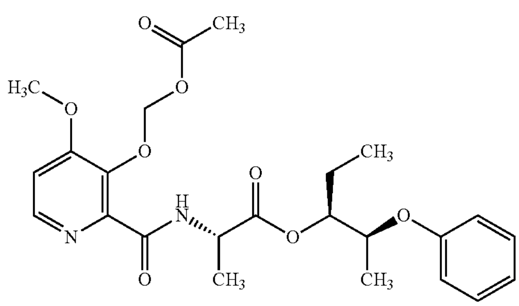 [SMILES: CC[C@H](OC(=O)[C@H](C)NC(=O)c1nccc(OC)c1OCOC(C)=O)[C@H](C)Oc1ccccc1] | Example 14B. | Clear, Colorless Oil |
| 376 | 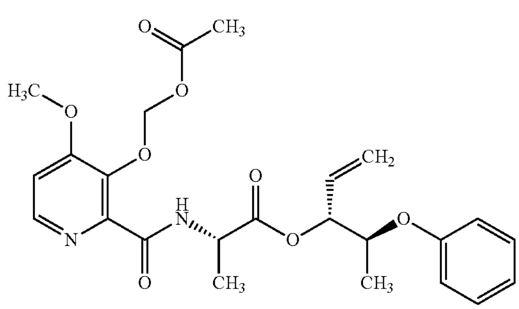 [SMILES: C=C[C@@H](OC(=O)[C@H](C)NC(=O)c1nccc(OC)c1OCOC(C)=O)[C@H](C)Oc1ccccc1] | Example 14B. | Pale Yellow Oil |

TABLE 1-continued

Compound Structure, Preparation Method, and Appearance

| *Cmpd. No. | Structure | As Prepared According To | Appearance |
| --- | --- | --- | --- |
| 377 | 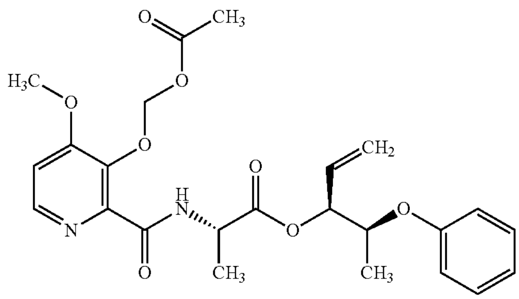 [SMILES: C=C[C@H](OC(=O)[C@H](C)NC(=O)c1nccc(OC)c1OCOC(C)=O)[C@H](C)Oc1ccccc1] | Example 14B. | Clear, Colorless Oil |
| 378 | 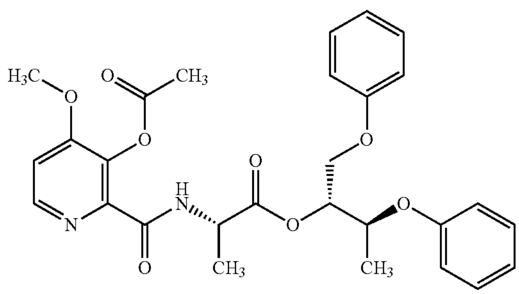 [SMILES: COc1ccnc(C(=O)N[C@@H](C)C(=O)O[C@H](COc2ccccc2)[C@H](C)Oc2ccccc2)c1OC(C)=O] | Example 14A. | Pale Yellow Oil |
| 379 | 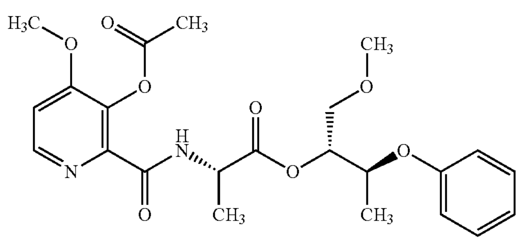 [SMILES: COC[C@@H](OC(=O)[C@H](C)NC(=O)c1nccc(OC)c1OC(C)=O)[C@H](C)Oc1ccccc1] | Example 14A. | Pale Yellow Oil |
| 380 | 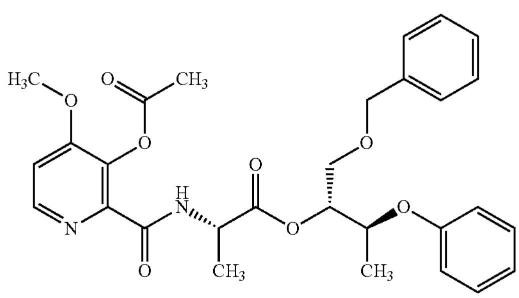 [SMILES: COc1ccnc(C(=O)N[C@@H](C)C(=O)O[C@H](COCc2ccccc2)[C@H](C)Oc2ccccc2)c1OC(C)=O] | Example 14A. | Clear, Colorless Oil |
| 381 | 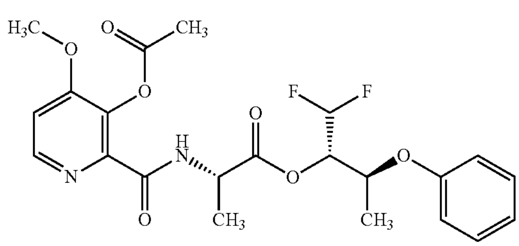 [SMILES: COc1ccnc(C(=O)N[C@@H](C)C(=O)O[C@H](C(F)F)[C@H](C)Oc2ccccc2)c1OC(C)=O] | Example 14A. | Clear, Colorless Oil |

TABLE 1-continued
Compound Structure, Preparation Method, and Appearance
| *Cmpd. No. | Structure | As Prepared According To | Appearance |
|---|---|---|---|
| 382 | 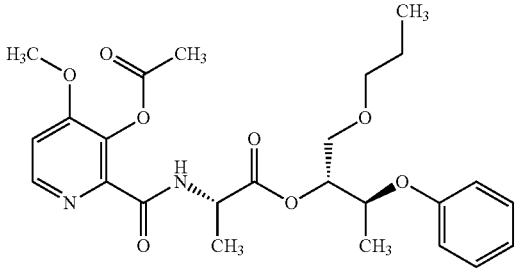 [SMILES: CCCOC[C@@H](OC(=O)[C@H](C)NC(=O)c1nccc(OC)c1OC(C)=O)[C@H](C)Oc1ccccc1] | Example 14A. | Clear, Colorless Oil |
| 383 | 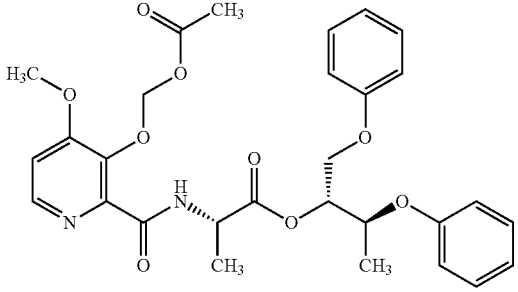 [SMILES: COc1ccnc(C(=O)N[C@@H](C)C(=O)O[C@H](COc2ccccc2)[C@H](C)Oc2ccccc2)c1OCOC(C)=O] | Example 14B. | Pale Yellow Oil |
| 384 | 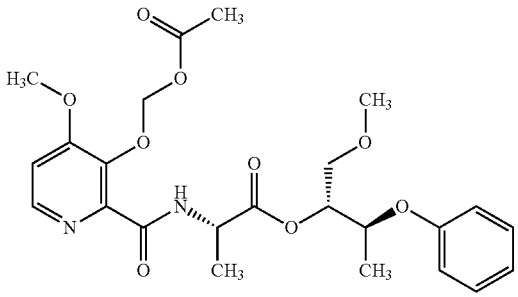 [SMILES: COC[C@@H](OC(=O)[C@H](C)NC(=O)c1nccc(OC)c1OCOC(C)=O)[C@H](C)Oc1ccccc1] | Example 14B. | Clear, Colorless Oil |
| 385 | 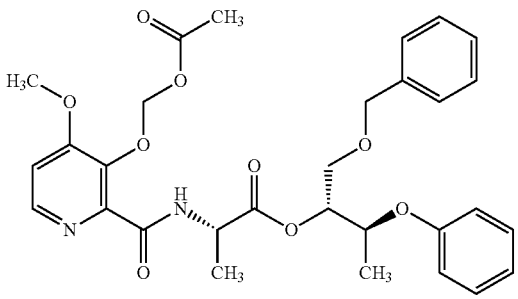 [SMILES: COc1ccnc(C(=O)N[C@@H](C)C(=O)O[C@H](COCc2ccccc2)[C@H](C)Oc2ccccc2)c1OCOC(C)=O] | Example 14B. | Clear, Colorless Oil |
| 386 | 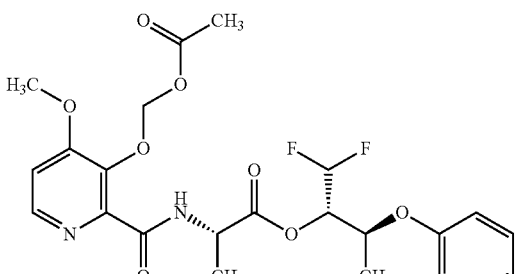 | Example 14B. | Clear, Colorless Oil |

TABLE 1-continued

Compound Structure, Preparation Method, and Appearance

| *Cmpd. No. | Structure | As Prepared According To | Appearance |
|---|---|---|---|
| 387 | 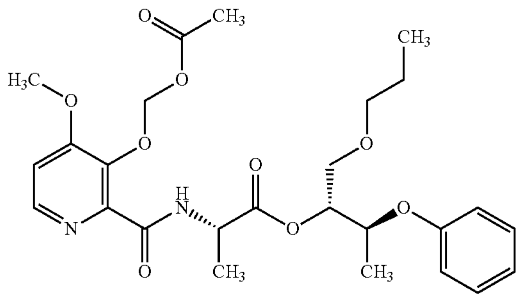 [SMILES: CCCOC[C@@H](OC(=O)[C@H](C)NC(=O)c1nccc(OC)c1OCOC(C)=O)[C@H](C)Oc1ccccc1] | Example 14B. | Clear, Colorless Oil |
| 388 | 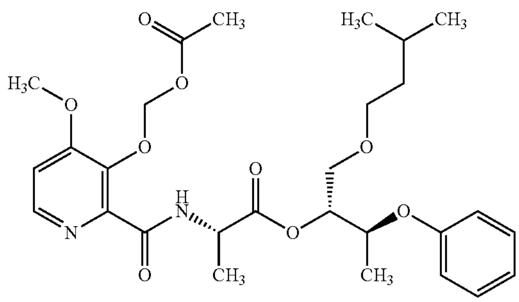 [SMILES: COc1ccnc(C(=O)N[C@@H](C)C(=O)O[C@H](COCCC(C)C)[C@H](C)Oc2ccccc2)c1OCOC(C)=O] | Example 14B. | Clear, Colorless Oil |
| 389 | 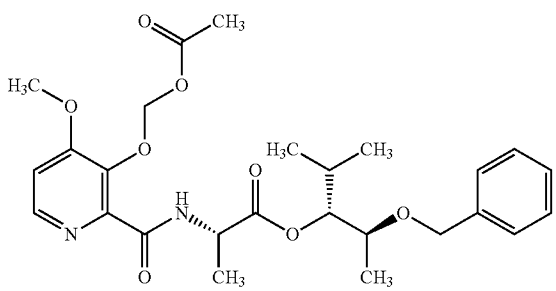 [SMILES: COc1ccnc(C(=O)N[C@@H](C)C(=O)O[C@H](C(C)C)[C@H](C)OCc2ccccc2)c1OCOC(C)=O] | Example 14B. | Thick Oil |
| 390 | 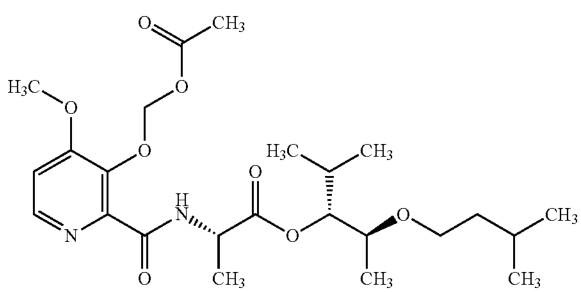 [SMILES: COc1ccnc(C(=O)N[C@@H](C)C(=O)O[C@H](C(C)C)[C@H](C)OCCC(C)C)c1OCOC(C)=O] | Example 14B. | Thick Oil |
| 391 | 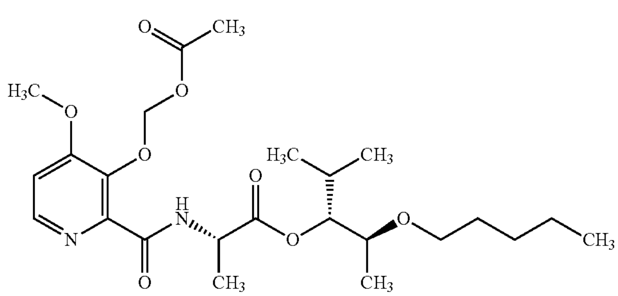 [SMILES: CCCCCO[C@@H](C)[C@H](OC(=O)[C@H](C)NC(=O)c1nccc(OC)c1OCOC(C)=O)C(C)C] | Example 14B. | Thick Oil |

TABLE 1-continued

Compound Structure, Preparation Method, and Appearance

| *Cmpd. No. | Structure | As Prepared According To | Appearance |
|---|---|---|---|
| 392 | 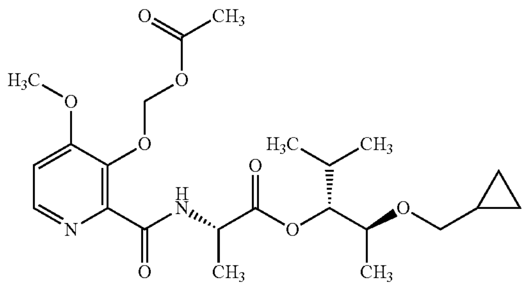 [SMILES: COc1ccnc(C(=O)N[C@@H](C)C(=O)O[C@H](C(C)C)[C@H](C)OCC2CC2)c1OCOC(C)=O] | Example 14B. | Thick Oil |
| 393 | 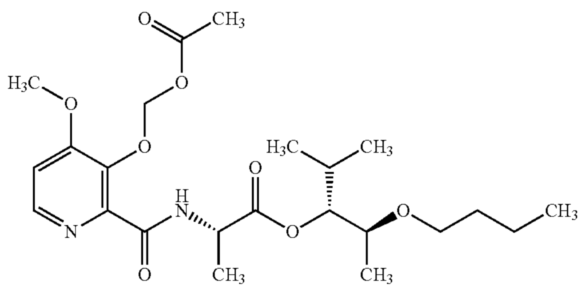 [SMILES: CCCCO[C@@H](C)[C@H](OC(=O)[C@H](C)NC(=O)c1nccc(OC)c1OCOC(C)=O)C(C)C] | Example 14B. | Thick Oil |
| 394 | 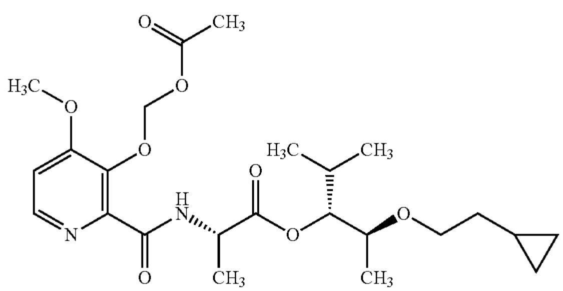 [SMILES: COc1ccnc(C(=O)N[C@@H](C)C(=O)O[C@H](C(C)C)[C@H](C)OCCC2CC2)c1OCOC(C)=O] | Example 14B. | Thick Oil |
| 395 | 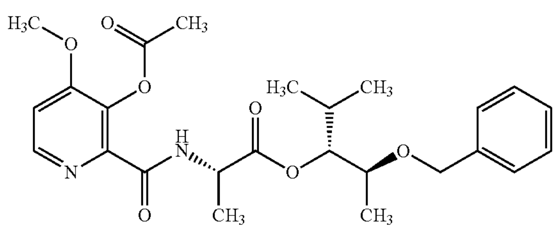 [SMILES: COc1ccnc(C(=O)N[C@@H](C)C(=O)O[C@H](C(C)C)[C@H](C)OCc2ccccc2)c1OC(C)=O] | Example 14A. | Thick Oil |
| 396 | 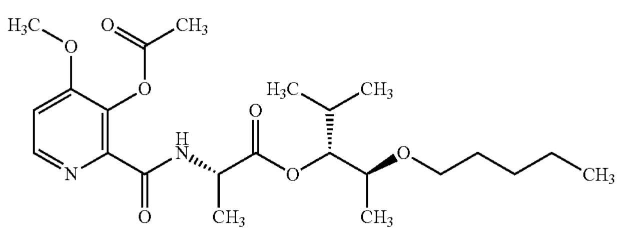 [SMILES: CCCCCO[C@@H](C)[C@H](OC(=O)[C@H](C)NC(=O)c1nccc(OC)c1OC(C)=O)C(C)C] | Example 14A. | Thick Oil |
| 397 | 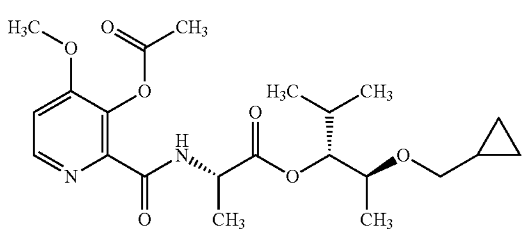 [SMILES: COc1ccnc(C(=O)N[C@@H](C)C(=O)O[C@H](C(C)C)[C@H](C)OCC2CC2)c1OC(C)=O] | Example 14A. | Thick Oil |

TABLE 1-continued

Compound Structure, Preparation Method, and Appearance

| *Cmpd. No. | Structure | As Prepared According To | Appearance |
|---|---|---|---|
| 398 | 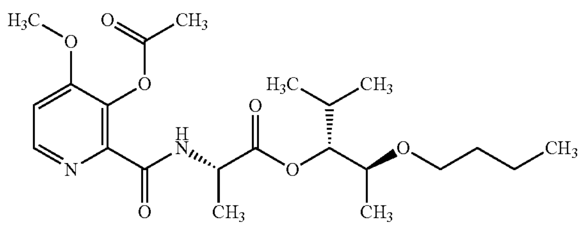 [SMILES: CCCCO[C@@H](C)[C@H](OC(=O)[C@H](C)NC(=O)c1nccc(OC)c1OC(C)=O)C(C)C] | Example 14A. | Thick Oil |
| 399 | 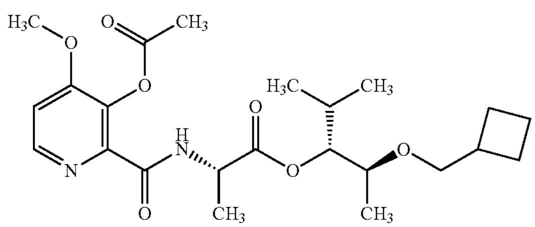 [SMILES: COc1ccnc(C(=O)N[C@@H](C)C(=O)O[C@H](C(C)C)[C@H](C)OCC2CCC2)c1OC(C)=O] | Example 14A. | Thick Oil |

*Cmpd. No. - Compound Number

Lengthy table referenced here
US10188109-20190129-T00001
Please refer to the end of the specification for access instructions.

Lengthy table referenced here
US10188109-20190129-T00004
Please refer to the end of the specification for access instructions.

Lengthy table referenced here
US10188109-20190129-T00002
Please refer to the end of the specification for access instructions.

Lengthy table referenced here
US10188109-20190129-T00005
Please refer to the end of the specification for access instructions.

Lengthy table referenced here
US10188109-20190129-T00003
Please refer to the end of the specification for access instructions.

Lengthy table referenced here
US10188109-20190129-T00006
Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US10188109B2). An electronic copy of the table will also be available from the USPTO upon request and payment of the fee set forth in 37 CFR 1.19(b)(3).

What is claimed is:

1. A compound of Formula I

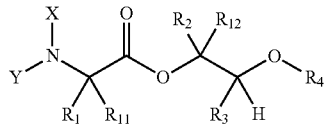

wherein
X is hydrogen or C(O)R$_5$;
Y is hydrogen, C(O)R$_5$, or Q;
Q is

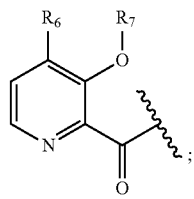

R$_1$ and R$_{11}$ are independently chosen from hydrogen or alkyl, optionally substituted with 0, 1 or multiple R$_8$;
alternatively, R$_1$ and R$_{11}$ may be taken together to form a 3-6 membered saturated or partially saturated carbocyclic or heterocyclic ring, optionally substituted with 0, 1 or multiple R$_8$;
R$_2$ and R$_{12}$ are independently chosen from hydrogen, alkyl, aryl, or alkenyl, each optionally substituted with 0, 1 or multiple R$_8$;
R$_3$ is methyl;
R$_4$ is chosen from alkyl, aryl, or acyl, each optionally substituted with 0, 1 or multiple R$_8$;
R$_5$ is chosen from alkoxy or benzyloxy, each optionally substituted with 0, 1, or multiple R$_8$;
R$_6$ is chosen from hydrogen, alkoxy, or halo, each optionally substituted with 0, 1, or multiple R$_8$;
R$_7$ is chosen from hydrogen, —C(O)R$_9$, or —CH$_2$OC(O)R$_9$;
R$_8$ is chosen from hydrogen, alkyl, aryl, acyl, halo, alkenyl, or alkoxy, each optionally substituted with 0, 1, or multiple R$_{10}$;
R$_9$ is chosen from alkyl, alkoxy, or aryl, each optionally substituted with 0, 1, or multiple R$_8$; and
R$_{10}$ is chosen from hydrogen, alkyl, aryl, acyl, halo, alkenyl, alkoxy, or heterocyclyl.

2. A compound according to claim 1, wherein X and Y are hydrogen.

3. A compound according to claim 2, wherein R$_1$ and R$_{11}$ are independently chosen from hydrogen or alkyl.

4. A compound according to claim 2, wherein R$_2$ and R$_{12}$ are independently chosen from hydrogen or alkyl, each optionally substituted with 0, 1 or multiple R$_8$.

5. A compound according to claim 2, wherein R$_4$ is aryl, optionally substituted with 0, 1 or multiple R$_8$.

6. A compound according to claim 2, wherein R$_1$ and R$_{11}$ are independently chosen from hydrogen or alkyl, R$_2$ and R$_{12}$ are independently hydrogen or alkyl, each optionally substituted with 0, 1 or multiple R$_8$, and R$_4$ is aryl, optionally substituted with 0, 1 or multiple R$_8$.

7. A compound according to claim 1, wherein X is C(O)R$_5$ and Y is hydrogen.

8. A compound according to claim 7, wherein R$_1$ and R$_{11}$ are independently chosen from hydrogen or alkyl.

9. A compound according to claim 7, wherein R$_2$ and R$_{12}$ are independently chosen from hydrogen or alkyl, each optionally substituted with 0, 1 or multiple R$_8$.

10. A compound according to claim 7, wherein R$_4$ is aryl, optionally substituted with 0, 1 or multiple R$_8$.

11. A compound according to claim 7, wherein R$_1$ and R$_{11}$ are independently chosen from hydrogen or alkyl, R$_2$ and R$_{12}$ are independently hydrogen or alkyl, each optionally substituted with 0, 1 or multiple R$_8$, and R$_4$ is aryl, optionally substituted with 0, 1 or multiple R$_8$.

12. A compound according to claim 1, wherein X is hydrogen and Y is Q.

13. A compound according to claim 12, wherein R$_6$ is alkoxy.

14. A compound according to claim 13, wherein R$_7$ is hydrogen.

15. A compound according to claim 14, wherein R$_1$ and R$_{11}$ are independently chosen from hydrogen or alkyl.

16. A compound according to claim 14, wherein R$_2$ and R$_{12}$ are independently chosen from hydrogen or alkyl, each optionally substituted with 0, 1 or multiple R$_8$.

17. A compound according to claim 14, wherein R$_4$ is aryl, optionally substituted with 0, 1 or multiple R$_8$.

18. A compound according to claim 14, wherein R$_1$ and R$_{11}$ are independently chosen from hydrogen or alkyl, R$_2$ and R$_{12}$ are independently hydrogen or alkyl, each optionally substituted with 0, 1 or multiple R$_8$, and R$_4$ is aryl, optionally substituted with 0, 1 or multiple R$_8$.

19. A compound according to claim 13, wherein R$_7$ is chosen from —C(O)R$_9$, or —CH$_2$OC(O)R$_9$.

20. A compound according to claim 19, wherein R$_1$ and R$_{11}$ are independently chosen from hydrogen or alkyl.

21. A compound according to claim 19, wherein R$_2$ and R$_{12}$ are independently chosen from hydrogen or alkyl, each optionally substituted with 0, 1 or multiple R$_8$.

22. A compound according to claim 19, wherein R$_4$ is aryl, optionally substituted with 0, 1 or multiple R$_8$.

23. A compound according to claim 19, wherein R$_1$ and R$_{11}$ are independently chosen from hydrogen or alkyl, R$_2$ and R$_{12}$ are independently hydrogen or alkyl, each optionally substituted with 0, 1 or multiple R$_8$, and R$_4$ is aryl, optionally substituted with 0, 1 or multiple R$_8$.

24. A compound according to claim 23, wherein R$_9$ is chosen from —CH$_3$, —CH$_2$OCH$_2$CH$_3$, —CH$_2$CH$_2$OCH$_3$, —CH(CH$_3$)$_2$, —CH$_2$CH$_2$CH$_2$CH$_3$, or -cyclopropyl.

25. A composition for the control of a fungal pathogen including mixtures of at least one of the compounds of claim 12 and another pesticide including fungicides, insecticides, nematocides, miticides, arthropodicides, bactericides and combinations thereof.

26. A composition for the control of a fungal pathogen including mixtures of at least one of the compounds of claim 14 and another pesticide including fungicides, insecticides, nematocides, miticides, arthropodicides, bactericides and combinations thereof.

27. A composition for the control of a fungal pathogen including mixtures of at least one of the compounds of claim 19 and another pesticide including fungicides, insecticides, nematocides, miticides, arthropodicides, bactericides and combinations thereof.

* * * * *